United States Patent
Andreason et al.

(10) Patent No.: US 11,022,421 B2
(45) Date of Patent: Jun. 1, 2021

(54) LOW-FREQUENCY ELECTROMAGNETIC TRACKING

(71) Applicant: Lucent Medical Systems, Inc., Kirkland, WA (US)

(72) Inventors: Samuel Peter Andreason, Kirkland, WA (US); Gary Brian Sanders, Kirkland, WA (US)

(73) Assignee: LUCENT MEDICAL SYSTEMS, INC., Kirkland, WA (US)

( * ) Notice: Subject to any disclaimer, the term of this patent is extended or adjusted under 35 U.S.C. 154(b) by 343 days.

(21) Appl. No.: 16/071,891

(22) PCT Filed: Jan. 20, 2017

(86) PCT No.: PCT/US2017/014395
§ 371 (c)(1),
(2) Date: Jul. 20, 2018

(87) PCT Pub. No.: WO2017/127722
PCT Pub. Date: Jul. 27, 2017

(65) Prior Publication Data
US 2019/0025040 A1     Jan. 24, 2019

Related U.S. Application Data

(60) Provisional application No. 62/344,319, filed on Jun. 1, 2016, provisional application No. 62/281,155, filed on Jan. 20, 2016.

(51) Int. Cl.
*G01B 7/004* (2006.01)
*A61M 31/00* (2006.01)
(Continued)

(52) U.S. Cl.
CPC .............. *G01B 7/004* (2013.01); *A61B 5/062* (2013.01); *A61B 5/4836* (2013.01); *A61B 34/20* (2016.02);
(Continued)

(58) Field of Classification Search
CPC ..... H02J 1/00; H01F 1/00; A61B 1/00; A61B 17/00; A61B 2217/00
See application file for complete search history.

(56) References Cited

U.S. PATENT DOCUMENTS

| 3,870,137 A | 3/1975 | Fougere |
| 4,315,509 A | 2/1982 | Smit |

(Continued)

FOREIGN PATENT DOCUMENTS

| AU | 2009202733 B2 | 7/2013 |
| AU | 2011258874 B2 | 4/2015 |

(Continued)

OTHER PUBLICATIONS

Amphenol® RF, "Frequency Range Chart," archived Nov. 9, 2015, URL=https://web.archive.org/web/20151109154937/http://www.amphenolrf.com/frequency-range-chart/, download date Mar. 15, 2017, 3 pages.

(Continued)

*Primary Examiner* — Jermele M Hollington
*Assistant Examiner* — Temilade S Rhodes-Vivour
(74) *Attorney, Agent, or Firm* — Seed IP Law Group LLP

(57) ABSTRACT

A medical system tracks the position of a medical instrument within a body of a patient. The medical instrument includes an electromagnet structure having an inductor coil wound around a core. A control circuit applies a low frequency excitation signal across the inductor coil. The inductor coil and the core generate a magnetic field. A plurality of sensors sense parameters of the generated magnetic field and pro- (Continued)

duce sensor signals. The control circuit calculates the position of the medical instrument based on the produced sensor signals.

19 Claims, 18 Drawing Sheets

(51) Int. Cl.
    *A61B 34/20*     (2016.01)
    *A61B 5/06*     (2006.01)
    *A61B 5/00*     (2006.01)
    *A61M 25/01*     (2006.01)
    *A61B 90/00*     (2016.01)

(52) U.S. Cl.
    CPC ..... *A61M 31/00* (2013.01); *A61B 2034/2051* (2016.02); *A61B 2090/378* (2016.02); *A61B 2090/3954* (2016.02); *A61M 2025/0166* (2013.01)

(56) References Cited

U.S. PATENT DOCUMENTS

| | | |
|---|---|---|
| 4,686,332 A | 8/1987 | Greanias et al. |
| 4,710,708 A | 12/1987 | Rorden et al. |
| 4,937,743 A | 6/1990 | Rassman et al. |
| 5,098,426 A | 3/1992 | Sklar et al. |
| 5,119,104 A | 6/1992 | Heller |
| 5,144,120 A | 9/1992 | Krichever et al. |
| 5,211,165 A | 5/1993 | Dumoulin et al. |
| 5,377,678 A | 1/1995 | Dumoulin et al. |
| 5,424,524 A | 6/1995 | Ruppert et al. |
| 5,425,367 A | 6/1995 | Shapiro et al. |
| 5,425,382 A | 6/1995 | Golden et al. |
| 5,622,169 A | 4/1997 | Golden et al. |
| 5,645,065 A | 7/1997 | Shapiro et al. |
| 5,767,669 A | 6/1998 | Hansen et al. |
| 5,775,322 A | 7/1998 | Silverstein et al. |
| 5,840,024 A | 11/1998 | Taniguchi et al. |
| 5,879,297 A | 3/1999 | Haynor et al. |
| 5,902,238 A | 5/1999 | Golden et al. |
| 6,078,854 A | 6/2000 | Breed et al. |
| RE36,791 E | 7/2000 | Heller |
| 6,104,712 A | 8/2000 | Robert et al. |
| 6,129,668 A | 10/2000 | Haynor et al. |
| 6,173,715 B1 | 1/2001 | Sinanan et al. |
| 6,205,411 B1 | 3/2001 | DiGioia, III et al. |
| 6,216,028 B1 | 4/2001 | Haynor et al. |
| 6,263,230 B1 | 7/2001 | Haynor et al. |
| 6,292,680 B1 | 9/2001 | Somogyi et al. |
| 6,420,992 B1 | 7/2002 | Richmond |
| 6,429,800 B1 | 8/2002 | Richmond |
| 6,468,265 B1 | 10/2002 | Evans et al. |
| 6,926,227 B1 | 8/2005 | Young et al. |
| 6,933,849 B2 | 8/2005 | Sawyer |
| 7,154,430 B1 | 12/2006 | Buehler et al. |
| 7,158,754 B2 | 1/2007 | Anderson |
| RE40,927 E | 10/2009 | Wild et al. |
| 7,647,070 B2 | 1/2010 | Shah |
| 7,798,404 B2 | 9/2010 | Gelbman |
| 7,976,518 B2 | 7/2011 | Shaughnessy et al. |
| RE42,913 E | 11/2011 | Wild et al. |
| 8,197,494 B2 | 6/2012 | Jaggi et al. |
| RE43,681 E | 9/2012 | Wild et al. |
| 8,265,732 B2 | 9/2012 | Besz et al. |
| RE43,952 E | 1/2013 | Uhl et al. |
| 8,478,382 B2 | 7/2013 | Burnside et al. |
| 8,606,347 B2 | 12/2013 | Besz et al. |
| 8,644,907 B2 | 2/2014 | Hartmann et al. |
| 8,781,555 B2 | 7/2014 | Burnside et al. |
| 8,830,112 B1 | 9/2014 | Buehler et al. |
| 8,934,960 B2 | 1/2015 | Besz et al. |
| 9,028,441 B2 | 5/2015 | Kuhn |
| 9,061,139 B2 * | 6/2015 | Stevenson ............... H01G 4/40 |
| 9,131,956 B2 | 9/2015 | Shaughnessy et al. |
| 9,579,488 B2 | 2/2017 | Shaughnessy et al. |
| 9,585,599 B2 | 3/2017 | Besz et al. |
| 9,687,174 B2 | 6/2017 | Jaggi et al. |
| 2002/0043561 A1 | 4/2002 | Tsikos et al. |
| 2002/0165448 A1 | 11/2002 | Ben-Haim et al. |
| 2003/0006759 A1 | 1/2003 | Govari |
| 2003/0173072 A1 | 9/2003 | Vinegar et al. |
| 2003/0183390 A1 | 10/2003 | Veenstra et al. |
| 2003/0192691 A1 | 10/2003 | Vinegar et al. |
| 2003/0192693 A1 | 10/2003 | Wellington |
| 2003/0196801 A1 | 10/2003 | Vinegar et al. |
| 2003/0196810 A1 | 10/2003 | Vinegar et al. |
| 2003/0201098 A1 | 10/2003 | Karanikas et al. |
| 2003/0205378 A1 | 11/2003 | Wellington et al. |
| 2004/0040715 A1 | 3/2004 | Wellington et al. |
| 2004/0087877 A1 | 5/2004 | Besz et al. |
| 2004/0106449 A1 | 6/2004 | Walker et al. |
| 2006/0084867 A1 * | 4/2006 | Tremblay ............... A61B 34/20 600/434 |
| 2007/0085681 A1 | 4/2007 | Sawyer |
| 2007/0096852 A1 | 5/2007 | Lawrence et al. |
| 2008/0004663 A1 | 1/2008 | Jorgenson |
| 2009/0171190 A1 | 7/2009 | Uchiyama et al. |
| 2011/0098559 A1 | 4/2011 | Besz et al. |
| 2012/0130228 A1 | 5/2012 | Zellers et al. |
| 2012/0130229 A1 | 5/2012 | Zellers et al. |
| 2012/0226148 A1 | 9/2012 | Jaggi et al. |
| 2012/0245457 A1 * | 9/2012 | Crowley ............... A61B 8/445 600/424 |
| 2012/0253340 A1 * | 10/2012 | Stevenson ............... A61N 1/05 606/33 |
| 2013/0169272 A1 * | 7/2013 | Eichler ............... A61B 5/062 324/253 |
| 2014/0051983 A1 | 2/2014 | Schroeder et al. |
| 2014/0188422 A1 * | 7/2014 | Huber ............... A61B 5/062 702/104 |
| 2014/0196723 A1 | 7/2014 | Kirkpatrick et al. |
| 2014/0310594 A1 | 10/2014 | Ricci et al. |
| 2015/0238388 A1 | 8/2015 | Kuhn |
| 2016/0067148 A1 | 3/2016 | Nordquist et al. |
| 2017/0128701 A1 | 5/2017 | Shaughnessy et al. |
| 2017/0143235 A1 | 5/2017 | Besz et al. |

FOREIGN PATENT DOCUMENTS

| | | | |
|---|---|---|---|
| CA | 2 649 802 | A1 | 5/2008 |
| CA | 2 684 471 | A1 | 10/2008 |
| CA | 2 701 169 | A1 | 4/2009 |
| DE | 27 49 677 | C1 | 11/1998 |
| EP | 0 555 131 | A2 | 8/1993 |
| EP | 1 744 184 | A2 | 1/2007 |
| EP | 2 249 273 | B1 | 7/2012 |
| FR | 1459499 | A | 11/1966 |
| GB | 1 605 299 | A | 7/1988 |
| GB | 2 379 469 | B | 9/2004 |
| GB | 1 605 446 | A | 8/2005 |
| KR | 10-1499975 | B1 | 3/2015 |
| SG | 184736 | A1 | 10/2012 |
| WO | 01/61917 | A1 | 8/2001 |
| WO | 03/040513 | A2 | 5/2003 |
| WO | 2006/116122 | A2 | 11/2006 |

OTHER PUBLICATIONS

Carpenter Technical Articles, "Magnetic Properties of Stainless Steels," Jun. 2006, URL=https://www.cartech.com/techarticles.aspx?id=1476, download date Dec. 10, 2015, 3 pages.
Cheney, "Preparation and Properties of Pure Iron Alloys: II. Magnetic Properties of Iron-Carbon Alloys as Affected by Heat Treatment and Carbon Content," *Scientific Papers of the Bureau of Standards 18*:609-635, 1922. (30 pages).
Cobalt Development Institute, *Cobalt Facts*, 2006, Chap. 5, "Magnetic Alloys," pp. 23-28.
"Demagnetizing field," Wikipedia, archived Oct. 1, 2015, URL= https://en.wikipedia.org/w/index.php?title=Demagnetizing_field &oldid=683601792, download date Dec. 11, 2015, 6 pages.

(56) References Cited

OTHER PUBLICATIONS

CWS ByteMark & ByteMark, "Ferrite Rods, Bars, Slugs, Plates and Tubes," Aug. 30, 2012, URL=http://www.bytemark.com/products/rod_new.html, download date Nov. 24, 2015, 6 pages.
HSM Wire International Inc., "Insulation Film Enameled Guide," Rev. 2.6.20.13, 2013, 7 pages.
International Search Report, dated Apr. 7, 2017, for International Application No. PCT/US2017/014395, 2 pages.
Jiles et al., "Investigation of the Microstructural Dependence of the Magnetic Properties of 4130 Alloy Steels and Carbon Steels for NDE," in Thompson et al. (eds.), *Review of Progress in Quantitative Nondestructive Evaluation 6A*, Springer, Boston, Massachusetts, USA, 1987, pp. 1681-1690.
Landgraf et al., "Magnetic Properties of Silicon Steel Wires," *Proceedings of the Soft Magnetic Materials* 16:439-443, 2003.
Medvedeva et al., "Magnetism in bcc and fcc Fe with carbon and manganese," *J. Phys.: Condens. Matter* 22:316002, 2010. (8 pages).
Sacolick et al., "Electromagnetically tracked placement of a peripherally inserted central catheter,"*SPIE Medical Imaging Proceedings*, 2004, 5 pages.
Virjoghe et al., "Finite Element Analysis of Stationary Magnetic Field," in Ebrahimi (ed.), *Finite Element Analysis—New Trends and Developments*, IntechOpen, Online, 2012, pp. 101-130.
Bulk Wire, "Wire Gauge Reference Table," 2013, URL=http://www.bulkwire.com/wiregauge.asp, download date Dec. 11, 2015, 6 pages.

\* cited by examiner

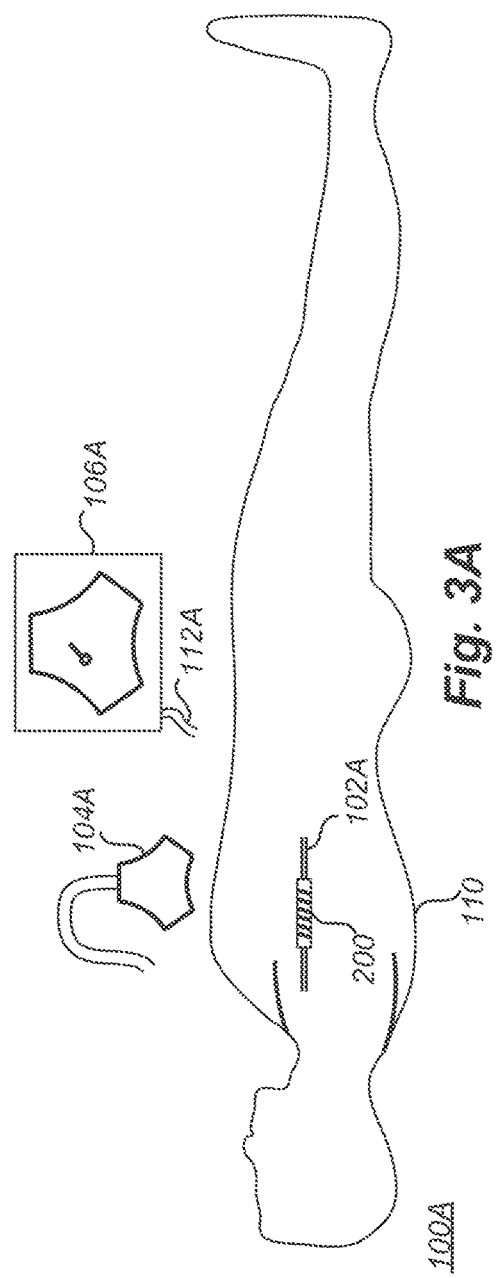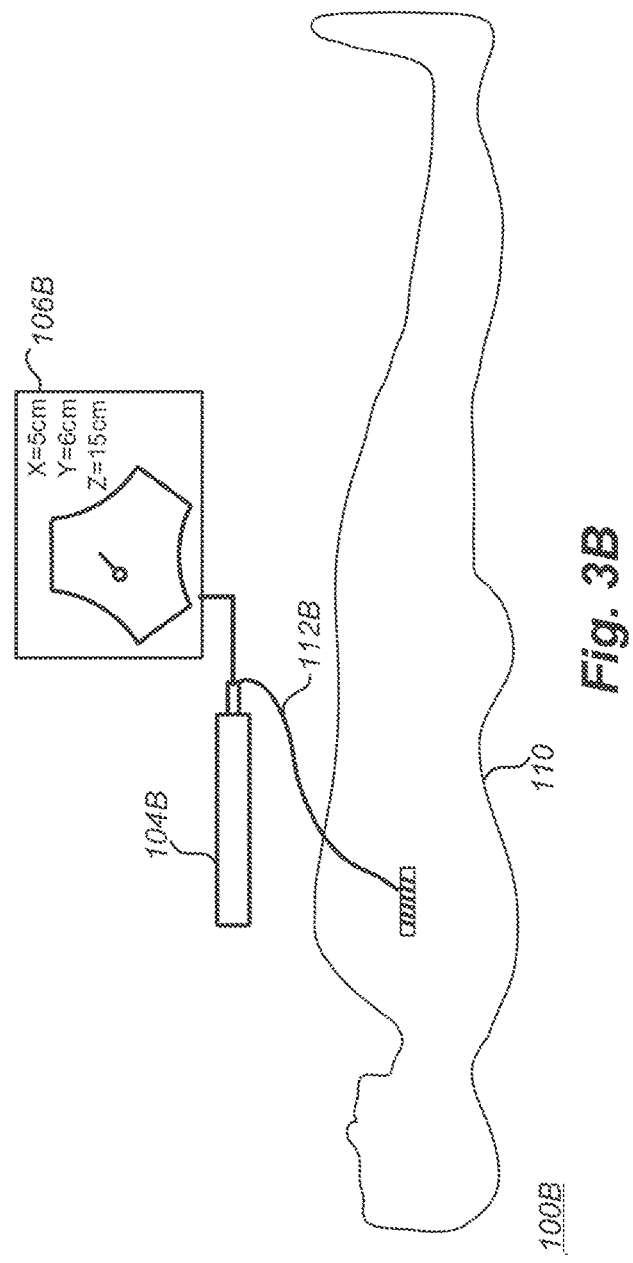

LOW-FREQUENCY ELECTROMAGNETIC TRACKING

CROSS-REFERENCE(S) TO RELATED APPLICATION(S)

This application claims the benefit of U.S. Provisional Patent Application No. 62/281,155, filed Jan. 20, 2016, and U.S. Provisional Patent Application No. 62/344,319, filed Jun. 1, 2016, both of which are hereby incorporated by reference in their entirety.

BACKGROUND

Technical Field

The present disclosure generally relates to tracking an electromagnetic device within a body. More particularly, but not exclusively, the present disclosure relates to tracking, in real time, an electromagnetic device stimulated with a low-frequency when the electromagnetic device is within a body.

Description of the Related Art

In many medical procedures, a medical practitioner accesses an internal cavity of a patient using a medical instrument. In some cases, the medical practitioner accesses the internal cavity for diagnostic purposes. In other cases, the practitioner accesses the cavity to provide treatment. In still other cases different therapy is provided.

Due to the sensitivity of internal tissues of a patient's body, incorrectly positioning the medical instrument within the body can cause great harm. Accordingly, it is beneficial to be able to precisely track the position of the medical instrument within the patient's body. However, accurately tracking the position of the medical instrument within the body can be quite difficult. The difficulties are amplified when the medical instrument is placed deep within the body of a large patient.

It is known that the medical instrument may be tracked as it travels or remains stationary within the patient's body. For example, U.S. Pat. No. 5,425,382 to Golden et al. is entitled, APPARATUS AND METHOD FOR LOCATING A MEDICAL TUBE IN THE BODY OF A PATIENT. The patent describes an apparatus and method for locating a medical tube within the body of a patient. The medical tube is located by a detection apparatus, which senses the static magnetic field strength gradient generated by a magnet associated with the medical tube. The detection apparatus indicates the value of the field strength gradient to the medical practitioner. To use the device, the detection apparatus is moved about the body of the patient until the greatest gradient magnitude is indicated. The detection apparatus distinguishes the field strength of the magnet associated with the medical tube from the earth's field strength by sensing the magnet's field strength at two different distances from the magnet. U.S. Pat. No. 5,425,382 to Golden et al. is incorporated herein by reference to the fullest extent allowed by law. Other examples are also provided. U.S. Pat. No. 5,622,169 to Golden et al. is entitled, APPARATUS AND METHOD FOR LOCATING A MEDICAL TUBE IN THE BODY OF A PATIENT. The patent describes a method of detecting the location of a magnet associated with a medical tube within the body of a patient. A first static magnetic field strength is sensed at a first distance from the magnet, and a second static magnetic field strength is sensed at a second distance from the magnet. The second distance is greater than the first distance. A first sensor signal is provided as a vector, which is a function of the first static magnetic field strength, and a second sensor signal is provided as a vector, which is a function of the second static magnetic field strength. The difference between the first static magnetic field strength and the second static magnetic field strength is provided as a differential signal vector value. The location of the medical tube can be determined by varying the first and second distances until the greatest value for the differential signal is indicated. U.S. Pat. No. 5,622,169 to Golden et al. is incorporated herein by reference to the fullest extent allowed by law.

U.S. Pat. No. 5,775,322 to Silverstein et al. is entitled, TRACHEAL TUBE AND METHODS RELATED THERETO. The patent describes a tracheal tube for insertion into the trachea of a patient. The tracheal tube includes a tube portion having a distal end, and a signal source such as a permanent magnet associated with the tube portion at a predefined distance from its distal end. The tracheal tube is inserted into the trachea of the patient such that the signal source is immediately posterior to the patient's cricothyroid ligament. Methods related to confirming proper placement of the tracheal tube by detecting the signal source immediately posterior to the patient's cricothyroid ligament are also disclosed. U.S. Pat. No. 5,775,322 to Silverstein et al. is incorporated herein by reference to the fullest extent allowed by law.

U.S. Pat. No. 5,879,297 to Haynor et al. is entitled, SYSTEM AND METHOD TO DETERMINE THE LOCATION AND ORIENTATION OF AN INDWELLING MEDICAL DEVICE. The patent describes a device to detect the location of a magnet coupled to an indwelling medical device within a patient. The device uses three or more sets of magnetic sensors each having sensor elements arranged in a known fashion. Each sensor element senses the magnetic field strength generated by the magnet, and each sensor element provides data indicative of the direction of the magnet in a three-dimensional space. The device uses fundamental equations for electricity and magnetism that relate measured magnetic field strength and magnetic field gradient to the location and strength of a magnetic dipole. The device uses an iterative process to determine the actual location and orientation of the magnet. An initial estimate of the location and orientation of the magnet results in the generation of predicted magnetic field values. The predicted magnetic field values are compared with the actual measured values provided by the magnetic sensors. Based on the difference between the predicted values and the measured values, the device estimates a new location of the magnet and calculates new predicted magnetic field strength values. This iteration process continues until the predicted values match the measured values within a desired degree of tolerance. At that point, the estimated location matches the actual location within a predetermined degree of tolerance. A two-dimensional display provides an indication of the location of the magnet with respect to the housing of the detector. A depth indicator portion of the display can be used to provide a relative or absolute indication of the depth of the magnet within the patient. U.S. Pat. No. 5,879,297 to Haynor et al. is incorporated herein by reference to the fullest extent allowed by law.

U.S. Pat. No. 5,902,238 to Golden et al. is entitled, MEDICAL TUBE AND APPARATUS FOR LOCATING THE SAME IN THE BODY OF A PATIENT. The patent describes a medical tube, an apparatus, and a method for locating the medical tube within the body of a patient. The medical tube has a permanent magnet associated therewith, which is capable of being located by a detection apparatus that senses the static magnetic field strength gradient generated by the permanent magnet. The detection apparatus indicates the value of the gradient to the user. In one embodiment, the magnet is associated with the distal end of the medical tube in a fixed orientation with a magnetic dipole pointing to the proximal end and parallel to a longitudinal axis of the medical tube. In this way, the polarity of the magnet's static magnetic field, as sensed by the detection apparatus, indicates the orientation of the distal end of the medical tube within the body of a patient. U.S. Pat. No. 5,902,238 to Golden et al. is incorporated herein by reference to the fullest extent allowed by law.

U.S. Pat. No. 6,129,668 to Haynor et al. is entitled, SYSTEM AND METHOD TO DETERMINE THE LOCATION AND ORIENTATION OF AN INDWELLING MEDICAL DEVICE. The patent describes a system to detect the position of a magnet associated with an indwelling medical device from a measurement location on the surface of a patient. The system includes a housing and first, second, and third magnetic sensors supported by the housing. Each of the magnetic sensors includes sensor elements to detect magnetic field strength in three orthogonal directions. The first, second, and third magnetic sensors generate first, second, and third sets of signals, respectively, as a function of static magnetic field strength and direction due to the magnet. A processor calculates an estimated position of the magnet in a three-dimensional space and calculates a predicted magnetic field strength for the first, second and third sensors based on the estimated position. The processor also calculates an actual magnetic field strength using the first, second, and third sets of signals and generates an error function based on a difference between the predicted magnetic field strength and the actual magnetic field strength. A display provides a visual display of data related to the position of the magnet in the three-dimensional space using the error function. U.S. Pat. No. 6,129,668 to Haynor et al. is incorporated herein by reference to the fullest extent allowed by law.

U.S. Pat. No. 6,173,715 to Sinanan et al. is entitled, MAGNETIC ANATOMICAL MARKER AND METHOD OF USE. The patent describes an anatomical marker that uses a permanent magnet to indicate a selected location within a patient. The magnet is enclosed within a non-degradable envelope and coupled to a retention member that is preferably manufactured from a biodegradable material, such as a polyglucuronic acid based material. The retention member may include one or more barbs to retain the anatomical marker in the selected location. An insertion tool, usable with an endoscope, can insert the anatomical marker. A retention magnet is fixedly attached to the insertion tool and holds the anatomical marker in place due to the attractive magnetic forces between the retention magnet and the marker magnet in the non-biodegradable envelope. When the anatomical marker is securely fastened at the selected location in the patient, the forces exerted by the patient's body on the retention member exceed the attractive magnetic forces between the retention magnet and the magnet in the envelope, thus causing the anatomical marker to be released from the insertion tool. The location of the magnet may be subsequently detected using a magnetic detector system. U.S. Pat. No. 6,173,715 to Sinanan et al. is incorporated herein by reference to the fullest extent allowed by law.

U.S. Pat. No. 6,216,028 to Haynor et al. is entitled, METHOD TO DETERMINE THE LOCATION AND ORIENTATION OF AN INDWELLING MEDICAL DEVICE. The patent describes a method to detect a position of a magnet associated with an indwelling medical device from a measurement location on the surface of a patient and in the presence of a magnetic field of the earth. In the method, first, second, and third magnetic sensors, having a known spatial relationship with respect to each other, are positioned at the measurement location. At the first sensor positioned at a first distance from the magnet, a first set of electrical signals are generated as a function of a first magnetic field strength and direction due to the magnet; at the second sensor positioned at a second distance from the magnet, a second set of electrical signals are generated as a function of a second magnetic field strength and direction due to the magnet; and at the third sensor positioned at a third distance from the magnet, a third set of electrical signals are generated as a function of a third magnetic field strength and direction due to the magnet. An estimated position of the magnet in a three-dimensional space is calculated, and a predicted magnetic field strength for the first, second and third sensors based on the estimated position is also calculated. The effects of the earth's magnetic field are canceled by subtracting a first selected one of the first, second, and third sets of electrical signals from a second selected one of the first, second, and third sets of electrical signals different from the first selected one of the first, second, and third sets of electrical signals to thereby generate a measured magnetic field strength using the first, second, and third sets of electrical signals. An error function is generated based on a difference between the predicted magnetic field strength and the measured magnetic field strength, and the three-dimensional position of the indwelling device is indicated by providing a visual display of the three-dimensional position of the associated magnet using the error function. U.S. Pat. No. 6,216,028 to Haynor et al. is incorporated herein by reference to the fullest extent allowed by law.

U.S. Pat. No. 6,263,230 to Haynor et al. is entitled, SYSTEM AND METHOD TO DETERMINE THE LOCATION AND ORIENTATION OF AN INDWELLING MEDICAL DEVICE. The patent describes a system to detect a position of a plurality of magnets within a patient from a measurement location outside the patient. The system includes a housing and a plurality of magnetic sensors supported by the housing. Each of the plurality of sensors is oriented in a known direction and generates a set of signals as a function of static magnetic field strength and direction due to the plurality of magnets within the patient. A processor calculates an estimated position of each of the plurality of magnets in a three-dimensional space and calculates values of a predicted magnetic field strength for at least a portion of the plurality of sensors based on the estimated positions of each of the plurality of magnets. The processor also calculates values of an actual magnetic field strength using the set of signals and determines values of the location of each of the plurality of magnets based on the difference between the values of the predicted magnetic field strength and the values of the actual magnetic field strength. A display provides a visual display of the position of each of the plurality of magnets in the three-dimensional space. U.S. Pat. No. 6,263,230 to Haynor et al. is incorporated herein by reference to the fullest extent allowed by law.

U.S. Pat. No. 6,292,680 to Somogyi et al. is entitled, NON-INVASIVE SENSING OF A PHYSICAL PARAMETER. The patent describes a method and device for non-invasively sensing a physical parameter within the body of a patient by employing a magnetically-based sensing device and a monitoring device. The magnetically-based sensing device has a first magnet and a second magnet, which generate a combined magnet field. The first and second magnets are positioned such that a change in a physical parameter causes a change in the combined magnet field, and the change is monitored by the monitoring device. U.S. Pat. No. 6,292,680 to Somogyi et al. is incorporated herein by reference to the fullest extent allowed by law.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which in and of itself may also be inventive.

BRIEF SUMMARY

Systems, devices, and methods to track one or more low-frequency electromagnetic trackable structures are described. Embodiments of such methods include advancing a medical instrument into the body of a patient, wherein the medical instrument has at least one low-frequency electromagnetic apparatus affixed thereto. Each low-frequency electromagnetic apparatus includes at least one ferromagnetic core and at least one conductor, each of which may be dedicated or shared. The at least one conductor has a first portion arranged as a plurality of coils wound around a ferromagnetic core and a second portion arranged as a set of conductive leads. Embodiments of the method further include applying a low-frequency excitation signal to the set of conductive leads and detecting in real time, from outside the patient's body, at least one magnetic field produced by the low-frequency electromagnetic apparatus. In some embodiments, visual information is presented to track the motion or stationary position of the medical instrument inside the body of the patient based on the detected magnetic field.

One embodiment is a system including a medical instrument configured to be inserted in a body of a patient, a control circuit, and a sensor. The medical instrument includes a first core and a first inductor coil wound around the first core. The control circuit is configured to pass a current through the first inductor coil by applying an excitation signal to the first inductor coil. The excitation signal has a frequency below 10,000 Hz, and the first inductor coil and the core are configured to generate a magnetic field based in part on the current. The sensor is configured to sense the magnetic field and the sensor is configured to output to the control circuit a sensor signal based on the magnetic field. The control circuit is further configured to calculate position information associated with the medical instrument within the body of the patient based on the sensor signal. In some cases, the frequency is less than 500 Hz. In some cases, the frequency is about 330 Hz. In some cases, medical instrument includes a tube, and in some of these cases, the tube is a catheter. In some cases, the medical instrument includes a medical implant configured to be permanently implanted within the patient. In some cases, the position information includes information representing a three-dimensional position of the medical instrument, an orientation of the medical instrument, and motion of the medical instrument, and in some of these cases, the control circuit is further configured to generate a video signal and the control circuit is further configured to output the video signal to a display, wherein the video signal includes a representation of the position information. In some cases, the first inductor coil includes a wire coated in a first insulator material. In some cases, the first core has a thickness less than 0.020 inches.

One embodiment is a low-frequency electromagnetic trackable structure that includes a medical instrument having a core formed on a distal end of the medical instrument, wherein at least the distal end of the medical instrument is arranged for insertion into the body of a patient, and an inductor coil wound around the core, wherein the inductor coil is arranged to receive an excitation signal having a frequency below 10,000 Hz, the low-frequency electromagnetic trackable structure arranged to generate a trackable magnetic field when the excitation signal is received. In some cases, the frequency of the excitation signal is about 330 Hz. In some cases, the medical instrument is a peripherally inserted central catheter (PICC). In some cases, the low-frequency electromagnetic trackable structure further includes a surface coating arranged on at least part of the low-frequency electromagnetic trackable structure, the surface coating including a bio-compatible material. In some cases, the medical instrument is arranged as a needle having a first portion of a first material and a second portion of a second material, the first material and the second material having different elemental compositions, wherein the core is integrated in the first portion of the needle. In some of these cases, the first material is a ferromagnetic material.

One embodiment is a method to track a low-frequency electromagnetic trackable structure. The method includes advancing a medical device into the body of a patient, and the medical device has a low-frequency electromagnetic apparatus affixed thereto. The low-frequency electromagnetic apparatus includes at least one ferromagnetic core and at least one conductor having a first portion and a second portion, the first portion arranged as a plurality of coils wound around the at least one ferromagnetic core and the second portion arranged as a set of first and second conductive leads. The method also includes applying a low-frequency excitation signal to the set of first and second conductive leads, detecting in real time, from outside the patient's body, at least one magnetic field produced by the low-frequency electromagnetic apparatus, and presenting visual information that tracks motion of the medical device inside the body of the patient based on the detection of the at least one magnetic field. In some cases, the low-frequency excitation signal is below 500 Hz. In some cases, the at least one ferromagnetic core has a cross-section diameter of between about 0.005 inches and 0.250 inches. In some cases, the at least one ferromagnetic core has a cross-section diameter of between about 0.00025 inches and 0.05 inches.

One embodiment is a system for detecting the position of a medical instrument within the body of a patient. The medical instrument includes an electromagnet that facilitates tracking the position of the medical instrument within the body of the patient. The electromagnet includes a core and an inductor coil wrapped around the core. The system further includes a control circuit configured to pass a current through the inductor coil by applying a low-frequency excitation signal to the inductor coil. The inductor coil is configured to generate a magnetic field based on the current. The system further includes a sensor configured to sense the magnetic field and to output to the control circuit a sensor signal based on the magnetic field, the control circuit being configured to determine one or more of a position, an orientation, and a motion of the medical instrument within the body of the patient based on the sensor signal.

One embodiment is a method for tracking a medical instrument within a body of a patient. The method includes generating a magnetic field by passing a current through an inductor coil wound around a core. Passing a current through the inductor coil includes applying a low-frequency excitation signal to the inductor coil. The low-frequency excitation signal has a frequency less than 10,000 Hz, preferably less than 500 Hz. The inductor coil and the core are disposed on a medical instrument positioned in a body of a patient. The method also includes generating a magnetic field in the first core based on the first current and sensing the magnetic field with a sensor. The method further includes generating a sensor signal based on the magnetic field and a determination of one or more of a position, an orientation, and a motion of the medical instrument within the body of the patient based on the sensor signal.

This Brief Summary has been provided to introduce certain concepts in a simplified form that are further described in detail below in the Detailed Description. Except where otherwise expressly stated, the summary is not intended to identify key or essential features of the claimed subject matter, nor is it intended to limit the scope of the claimed subject matter.

BRIEF DESCRIPTION OF THE SEVERAL VIEWS OF THE DRAWINGS

Non-limiting and non-exhaustive embodiments are described with reference to the following drawings, wherein like labels refer to like parts throughout the various views unless otherwise specified. The sizes and relative positions of elements in the drawings are not necessarily drawn to scale. The shapes of various elements and angles are not necessarily drawn to scale either, and some of these elements are enlarged and positioned to improve drawing legibility. One or more embodiments are described hereinafter with reference to the accompanying drawings in which:

FIG. 3A illustrates a low-frequency electromagnetic tracking system embodiment;

FIG. 3B is illustrates a medical environment including a system for detecting the position of a medical instrument within the body of a patient, according to one embodiment;

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with computing systems including client and server computing systems, as well as networks have not been shown or described in detail to avoid unnecessarily obscuring descriptions of the embodiments.

A medical instrument having a new trackable structure is contemplated. The trackable structure includes a low-frequency electromagnetic apparatus that is trackable with a magnetic field sensing device. The magnetic field sensing device includes particular algorithms to identify and track the position of the low-frequency electromagnetic apparatus in three dimensions and the orientation of low-frequency electromagnetic apparatus relative to a reference point. A display associated with the magnetic field sensing device presents output information to a medical practitioner representing the position and orientation of at least one of the trackable structure and the low-frequency electromagnetic apparatus.

Figure 1:
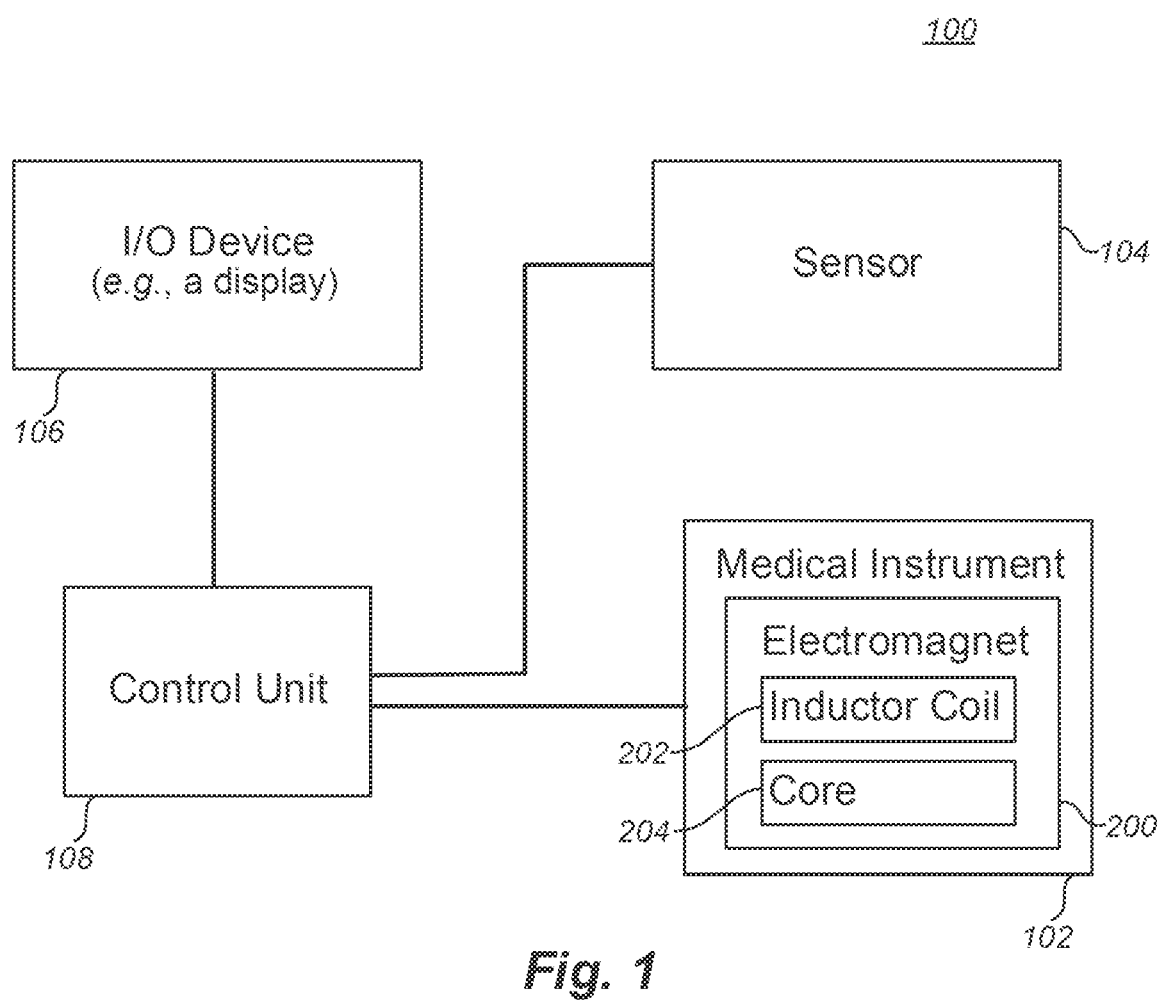
FIG. 1 is a block diagram of a system for detecting the position of a medical instrument within a body of a patient, according to one embodiment.

FIG. 1 is a block diagram of a system 100 for detecting the position of a medical instrument 102 within the body of a patient, according to one embodiment. The system 100 includes one or more medical instruments 102, a sensor 104, an input/output device 106, and a control circuit 108. The control circuit 108 is coupled to the medical instrument 102, the sensor 104, and the input/output device 106. The medical instrument 102 includes at least one electromagnet structure 200. The at least one electromagnet structure 200 includes at least one inductor coil 202 wound about a core 204.

In some cases, one or more components of the system 100 are integrated. In other cases, two or more components of the system 100 are separate and distinct. For example, in at least one embodiment, the sensor 104, input/output device 106, and control circuit 108 are arranged in a single package (e.g., a single housing). In other embodiments, individual circuits of the components are separate and distinct while also cooperatively coupled. For example, in at least one embodiment, the control circuit 108 includes one or more circuits integrated with the input/output device 106 and one or more circuits integrated with the sensor 104.

In some cases, the at least one electromagnet structure 200 includes a plurality of electromagnets. In some of these cases, each one of the plurality of electromagnets may have a separate and distinct core 204. In some of these cases, two or more electromagnets share a common core 204. In some of these cases, each electromagnet includes an inductor coil 202 formed from one or more separate and distinct conductors. In some of these cases, each electromagnet includes an inductor coil 202 formed from one or more shared conductors.

In one embodiment, the medical instrument 102 is a medical device configured to be introduced, either partially or wholly, into the body of a patient in conjunction with a medical procedure. Representative but not exhaustive examples of medical instruments include complete, or portions of, cardiovascular devices and implants such as implantable cardioverter defibrillators, pacemakers, pacemaker leads, stents, stent grafts, bypass grafts, catheters and heart valves; orthopedic implants such as hip and knee prosthesis; spinal implants and hardware (spinal cages, screws, plates, pins, rods and artificial discs); a wide variety of medical tubes, cosmetic and/or aesthetic implants (e.g., breast implants, fillers); a wide variety of polymers, bone cements, bone fillers, scaffolds, and naturally occurring materials (e.g., heart valves, and grafts from other naturally occurring sources); intrauterine devices; orthopedic hardware (e.g., casts, braces, tensor bandages, external fixation devices, tensors, slings and supports) and internal hardware (e.g., K-wires, pins, screws, plates, and intramedullary devices (e.g., rods and nails)); cochlear implants; dental implants; medical polymers, a wide variety of neurological devices; fiducial markers; intravascular stylets (e.g., ECG stylets); stylets pre-loaded into respective catheters; central venous catheters; peripherally inserted central venous catheters; guidewires; thermal energy delivery devices; cryonic therapy delivery devices; photonic therapy delivery devices; cautery delivering catheters; balloon catheters; and other such devices. The medical instrument 102 can also include many other kinds of medical devices that can be introduced into the body of a patient as part of a medical procedure. The patient may be a human patient or a non-human patient.

In some cases, the input/output device 106 is an input device only. In some cases, the input/output device 106 is an output device only. For example, the input/output device may include in total or in part any one or more of a display, a keyboard, a mouse, a tactile apparatus (e.g., touchscreen, vibrator), a programmatic communication port (e.g., serial port such as a universal serial bus (USB) port, wireless transceiver such as a cellular-based radio, an IEEE 802.11 radio), an audio apparatus (e.g., microphone, speaker, piezo circuit device), or any other such input/output device. The input/output device 106 may be contained in a single circuit or a plurality of distributed circuits, which may all be local, remote, or a combination of local and remote to each other. For example, in some cases, the input/output device 106 includes a local display and a remote display communicatively coupled to the system 100 via a network such as the Internet.

In some cases, the electromagnet structure 200 is integrated with the medical instrument 102. For example, when the medical instrument 102 includes or is a stylet, the electromagnet structure 200 may be formed as part of the stylet. In other cases, the electromagnet structure 200 is fixedly or removably coupled to the medical instrument 102. The range of cooperative combinations of medical instruments 102 and electromagnet structures 200 is not limited merely to the combinations described herein, which are limited for brevity. Rather, the range of cooperative combinations of medical instruments 102 and electromagnet structures 200 is broadly inclusive of those contemplated by one of ordinary skill in the art.

In many medical procedures, it is advantageous to track the position of the medical instrument 102 within the body of the patient with acceptable accuracy. For example, if the medical instrument 102 is delivering fluid to a particular part of the patient's body, then it can be advantageous to accurately track the position of medical instrument 102 to ensure that the medical instrument 102 is in the correct position for fluid delivery. In some particularly sensitive medical procedures, knowing the exact position of the medical instrument 102 with an acceptable level of accuracy can help ensure the well-being of the patient during a medical procedure.

The electromagnet structure 200 enables tracking of the position of the medical instrument 102. When a current is passed through an inductor coil 202, a magnetic field is generated. Depending at least in part on the material of the core 204, the core 204 can supplement or strengthen the generated magnetic field. The generated magnetic field can enable tracking of the medical instrument 102.

The sensor 104 includes one or more magnetic sensors arranged to detect one or more magnetic fields generated by an inductor coil 202 and core 204 of an electromagnet structure 200. The sensor 104 can detect certain parameters of the generated magnetic field such as field strength and polarity (i.e., direction). The sensor 104 generates one or more sensor signals indicative of the parameters of a generated magnetic field. The position of the medical instrument 102, and in some cases the position of two or more medical instruments 102, along with orientation, motion, and other location-based information can be determined based on the parameters of a magnetic field generated by the electromagnet structure 200. Operations of the sensor 104 are in some cases coordinated by the control circuit 108 such that parameters to direct certain sensor functions are applied in cooperation with parameters to direct excitation of the electromagnet structure 200.

In one embodiment, the control circuit 108 both drives electric current through an inductor coil 202 and calculates location-based information (e.g., position, orientation, motion, timing, and the like) of a particular medical instrument 102. The control circuit 108 receives one or more sensor signals from the sensor 104 and analyzes the one or more sensor signals. The control circuit 108 generates the location-based information, such as the position of the medical instrument 102, based on the one or more sensor signals.

In one embodiment, control circuit 108 executes particular algorithms to identify and track the position of medical instruments 102 in three dimensions and the orientation of medical instruments 102 relative to a reference point. The identification and tracking of one or more medical instruments 102 by a control circuit 108 is based, at least in part, on the position of the electromagnet structure 200. In these and other cases, tracking the position of a medical instrument 102 includes integrating current and historical position data in order to predict one or more future positions of the respective medical instrument 102.

It can be difficult to accurately track the position of a medical instrument 102 within the body of a patient as the medical instrument 102 is positioned deeper within the body of the patient. In larger patients, for example, the problem can be exacerbated because the medical instrument 102 may need to travel deeper below the skin and deeply into the body of the patient in order to reach particular areas inside the body in accordance with various medical procedures. It can be difficult to generate a magnetic field with sufficient strength and stability to allow reliable tracking of the medical instrument 102. This problem can be compounded by the fact that in many circumstances it is more desirable to have an inductor coil 202 and a core 204 that are relatively small in order to minimize disruption of body tissues as the medical instrument 102 is introduced into the body of the patient. This problem can also be compounded by naturally occurring magnetic fields (e.g., the earth's magnetic field) and man-made magnetically disruptive structures such as bed frames and other ferrous medical devices. As the dimensions of the inductor coil 202 are reduced, it can be difficult to generate sufficiently strong and acceptably stable magnetic fields to enable detection. Furthermore, interference as described herein (e.g., from the earth's magnetic field, from other medical and non-medical equipment positioned in or near the patient's body), and even interference from the medical instrument 102 itself can make it difficult to calculate the position of the medical instrument 102 within the body of the patient with acceptable accuracy.

In one embodiment, in order to enable more accurate tracking of the medical instrument 102 deep within the body of a patient, the control circuit 108 drives the inductor coil 202 with a low-frequency alternating current (AC) excitation signal instead of a direct current (DC) signal or a high-frequency excitation signal. The low-frequency excitation signal causes a current to be passed through the inductor coil 202. As the direction and magnitude of the excitation current change, the parameters of the magnetic field generated by the inductor coil 202 also change.

The magnetic field generated by the electromagnet structure 200 has particular characteristics based in part on a waveform of the excitation signal. These particular oscillating characteristics can enable the control circuit 108 to distinguish the generated magnetic field from noise, interference, and/or magnetic fields produced by devices or circumstances different from the electromagnet structure 200. In this way, the control circuit 108 can track the position of the medical instrument 102 with acceptable accuracy even when the medical instrument 102 is deep within the body of a patient.

In at least one embodiment, the control circuit 108 drives the inductor coil 202 with an excitation signal having a frequency less than 10,000 Hz. In at least one of these embodiments, the control circuit 108 can drive the inductor coil 202 with an excitation signal having a frequency less than 500 Hz. In some embodiments, the control circuit 108 drives the inductor coil 202 with an excitation signal having a frequency of about 330 Hz. The selection of a 330 Hz excitation signal, for example, helps to avoid AC line related components, which might occur at a multiple of a line frequency. For example, 300 Hz, which is a multiple of both 50 Hz and 60 Hz, which are two common line frequencies conventionally used in Europe and the U.S., respectively, may provide strong magnetic returns, but the strong magnetic returns may also have measurable harmonic components associated with the AC line frequency. For at least these reasons, some embodiments select an excitation signal having a frequency below 500 Hz, near 330 Hz, and in avoidance of integer multiples of a common line frequency.

Control circuit 108 has been described as driving an inductor coil 202 with an excitation signal or applying an excitation signal to an inductor coil 202. The control circuit 108 can accomplish this by directly applying the excitation signal to the inductor coil 202. Alternatively, the control circuit 108 can accomplish this indirectly by controlling a voltage source that applies a voltage to the inductor coil 202 or by controlling a current source that supplies a current to the inductor coil 202. Those of skill in the art will recognize, in light of the present disclosure, that the control circuit 108 can generate, pass, or otherwise apply an excitation signal to the inductor coil 202 in many other ways. All such other ways are within the scope of the present disclosure.

In at least one embodiment, the input/output device 106 includes a display that presents a visual representation of the position of one or more medical instruments 102 within the body of the patient. The visual representation of the position of a medical instrument 102 enables a medical practitioner to know the position of the medical instrument 102 within the body of the patient with acceptable accuracy. This in turn can enable the medical practitioner to correctly perform medical procedures on the patient.

In some embodiments, the control circuit 108 generates a video signal and outputs the video signal to the input/output device 106 (e.g., a display). The video signal includes a representation of the position of one or more medical instruments 102 within the body of the patient. The video signal can also include position data that can be displayed or otherwise presented via the input/output device 106. The position data can include text that indicates numerical coordinates representing the position, orientation, and motion of the medical instrument 102. The video signal displayed or otherwise presented via the input/output device 106 can present in real time both a visual representation of the position of the medical instrument 102 within the body of the patient and certain position data that indicates the position of the medical instrument 102 within the body of the patient.

The control circuit 108 may include multiple discrete control circuit portions. Control circuit 108 can include one or more microcontrollers, one or more microprocessors, one or more memory devices, one or more voltage sources, one or more current sources, one or more analog-to-digital converters, one or more digital-to-analog converters, and/or one or more wireless transceivers. One or more of these components can collectively make up the control circuit 108.

Figure 2A:
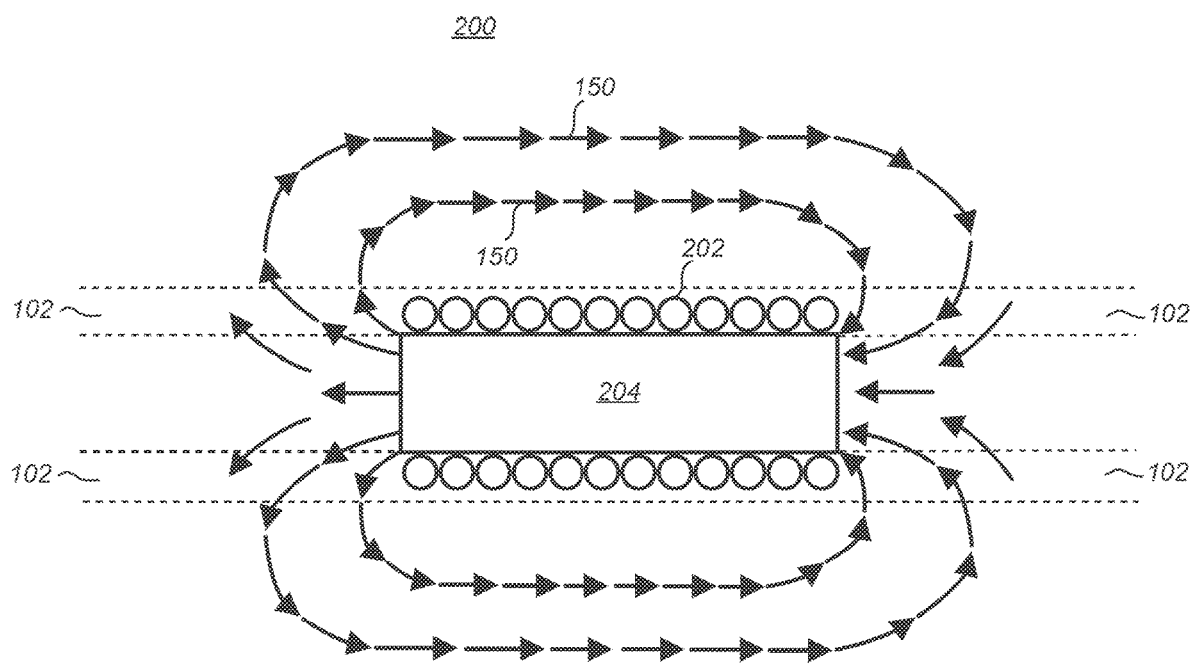
FIG. 2A is a cross-sectional diagram of an electromagnet including magnetic field lines, according to one embodiment.

FIG. 2A is a cross-sectional view of an electromagnet structure 200 that is part of a medical instrument 102, according to one embodiment. The medical instrument 102 in FIG. 2A is illustrated in dashed lines to represent a medical instrument 102 that may conform to any number of embodiments as discussed herein. For example, in some cases, the medical instrument 102 is, or includes, a structure having a hollowed portion wherein some or all of the electromagnetic structure 200 is placed, formed, embedded, or otherwise integrated. In other cases, the medical instrument or some portion of the medical instrument forms a core 204 on which the inductor coil 202 is arranged. In still other cases, the electromagnet structure 200 fully or partially surrounds the medical device 102.

In at least one embodiment, an electromagnet structure 200 is formed in a tube. The tube may be a pure material, a composition, or an alloy. The tube, or any other portion of the medical instrument 102, may comprise metal, rubber, plastic, epoxy, urethane, or some other material. In cases where the tube is pure metal or includes metal in any purity, a generated magnetic field such as shown in FIG. 2A may nevertheless be detectable by a sensor 104 (FIG. 1).

In the medical instrument 102 embodiment of FIG. 2A, the control circuit 108 (FIG. 1) has applied a voltage across the inductor coil 202, thereby causing a current to flow through the inductor coil 202. The illustration of FIG. 2A represents a point in time of the application of an excitation signal to the inductor coil 202. When a current passes through the inductor coil 202, the inductor coil 202 generates a magnetic field. The magnetic field has a polarity (i.e., direction) based on the direction of flow of the current through the inductor coil 202.

In FIG. 2A, current flows through the inductor coil 202 in a direction into the page at the top of the inductor coil 202 and out of the page at the bottom of the inductor coil 202. This direction of current flow generates a magnetic field as illustrated by the arrowed magnetic field lines 150. Each of the magnetic field lines 150 forms a loop that goes from the left side of the core 204 to the right side of the core 204 in accordance with the direction of the arrows on the magnetic field lines 150.

The strength of the magnetic field illustrated in FIG. 2A at any given location is representatively illustrated by the density of the magnetic field lines 150. In particular, where magnetic field lines 150 are closer together, the magnetic field is stronger. Where magnetic field lines 150 are further apart from each other, the magnetic field is weaker. The direction of the magnetic field is indicated by the direction of the arrows on the magnetic field lines 150 at any given location. As the direction of the current changes, which happens with an AC excitation signal, the magnetic field lines 150 will also change direction. Hence, as the excitation signal traverses its particular waveform over time, a magnetic field will correspondingly form, grow, and collapse.

The magnetic field generated by the electromagnet structure 200 enables generation of position information associated with the medical instrument 102 (FIG. 1) within the body of the patient. It is beneficial to be able to detect the position, orientation, and movement of the medical instrument 102 at any depth within the body of the patient. However, as the depth of the medical instrument 102 within the body of the patient increases, the difficulty in detecting the magnetic field generated by the electromagnet structure 200 of the medical instrument 102 also increases. This problem can be amplified with larger patients where the medical instrument 102 may need to be positioned very deep below the surface of the skin in order to perform a selected function. That is, as the electromagnet structure 200 travels further from the sensor 104 (FIG. 1), it is more difficult to detect the generated magnetic field and reliably determine position, orientation, and movement information associated with the medical instrument 102.

One way to improve the detectability of a generated magnetic field is to increase the strength of the magnetic field. However, the strength of the magnetic field may depend on many factors. These factors often include trade-offs such that improving one feature of the electromagnet structure 200 causes a detriment to another feature of the electromagnet structure 200.

One factor that affects the strength of a magnetic field generated by an electromagnet structure 200 is the magnitude of the current that flows through the inductor coil 202. A larger current produces a larger magnetic field.

The materials and the dimensions of the materials that make up the inductor coil 202 contribute to the magnitude of the current that the inductor coil 202 can safely pass without damaging the inductor coil 202 or otherwise reducing its effectiveness. In order to safely pass a large current through the inductor coil 202, the wire or other material that forms inductor coil 202 may be correspondingly thick. Yet it can also be problematic to increase the thickness of the inductor coil 202 at least in part because the electromagnet structure 200 will be introduced into the body of the patient. A larger inductor coil 202 will cause a correspondingly larger disruption of tissues or other biological matter that make up the body of the patient as the medical instrument 102 that bears the electromagnet structure 200 is introduced into the body of the patient. Thus, it can be detrimental to increase the size of the inductor coil 202.

Another factor that affects the strength of a magnetic field generated by the electromagnet structure 200 is the number and density of windings in the inductor coil 202. The number of windings corresponds to the number of times that the wire or other material of the inductor coil 202 wraps around the core 204 in an electromagnet structure 200. In order to increase the number of windings and/or density of windings of the inductor coil 202, the wire or other coil material can be wound around itself in multiple layers of windings. However, adding additional layers of windings to an inductor coil 202 increases the overall size of the electromagnet structure 200. For reasons described herein, increasing the overall size of the inductor coil 202 may lead to other drawbacks associated with introducing the electromagnet structure 200 into the body of the patient with the medical instrument 102.

Some other factors that individually and/or collectively affect the strength of a magnetic field generated by an electromagnet structure 200 are the elemental material, dimensions, and configuration of the core 204. In particular, if the core 204 includes a material that can become magnetized, then the magnetic field generated by passing a current through the inductor coil 202 will be amplified by the effect of magnetizing the core 204.

Among magnetic materials, some can be more strongly magnetized than others. Furthermore, a larger core 204 can at least in some cases (e.g., based on parameters of an excitation signal) produce a larger magnetic field. Alternatively, or in addition, a core 204 composed of two or more elements may also produce a stronger magnet.

Thus, in at least one embodiment, the core 204 includes a material that can become magnetized in the presence of the magnetic field generated by passing a current through the inductor coil 202. The core 204 can include a ferromagnetic material, a paramagnetic material, or another type of material that is susceptible to becoming magnetized in the presence of the magnetic field generated by passing a current through the inductor coil 202. In some cases, the core 204 may also be formed from a diamagnetic material such as copper, silver, or gold in order to control other properties of the purposefully induced electromagnetic field.

A ferromagnetic material includes a plurality of individual magnetic domains that, in the absence of an external magnetic field, each have a magnetic moment pointed in a random direction. The sum of these magnetic moments in the various random directions typically results in the ferromagnetic material having a net magnetization of zero in the absence of an external magnetic field. When the ferromagnetic material is subjected to an external magnetic field, the individual domains eventually align in the direction of the external magnetic field. As the individual domains align, the core 204 produces a magnetic field. The magnetization of the core 204 supplements the magnetic field generated by passing a current through the inductor coil 202.

If a direct current (DC) voltage is applied across the inductor coil 202, the inductor coil 202 will eventually reach a steady state in which a constant DC current flows through the inductor coil 202. The steady DC current generates a steady magnetic field that eventually causes magnetization of the entire core 204. However, as described herein and in other places, such a steady magnetic field leads to complications that make detecting the position, orientation, and motion of the medical instrument 102 within the body of the patient more difficult. In particular, the earth's magnetic field, electromagnetic interference from other medical and non-medical equipment that may be positioned in or near the patient's body, from electronic circuitry, and from the medical instrument 102 itself, can make it difficult to determine with acceptable accuracy the position or other location-based information associated with the medical instrument 102 within the body of the patient when a DC current is passed through the inductor coil 202.

Accordingly, in at least one embodiment, the control circuit 108 applies a low-frequency excitation signal across the inductor coil 202. In one example, the low frequency is less than 10,000 Hz. The excitation signal drives an alternating current (AC) signal through the inductor coil 202. The changing current in the inductor coil 202 results in a changing magnetic field. The changing magnetic field may not allow the entirety of the core 204 to become magnetized. In fact, as the current in the inductor coil 202 changes, only a portion of the core 204 may become magnetized. The portion of the core 204 that becomes magnetized depends on several factors including the magnitude of the driving current, the frequency of the excitation signal, the waveform of the excitation signal, the magnetic permeability of the core 204, and other factors.

Figure 2B:
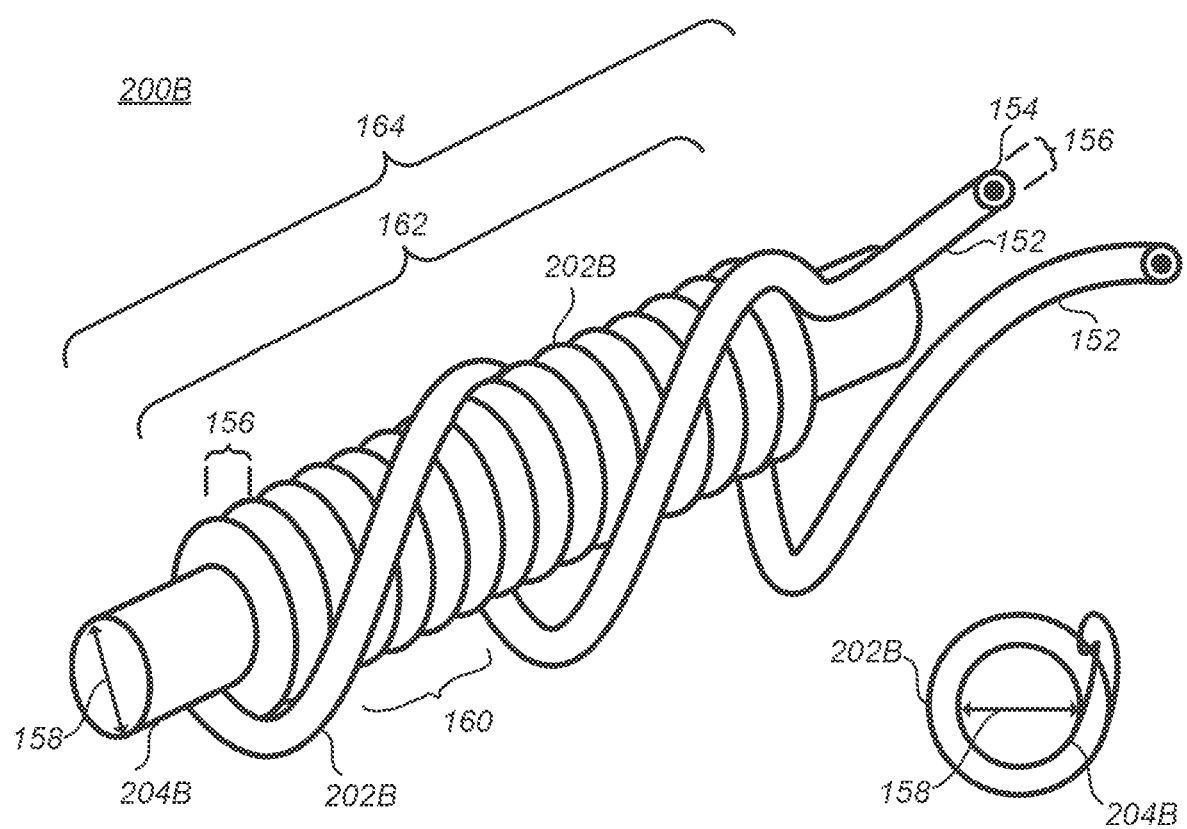
FIG. 2B illustrates an electromagnet, according to a first solid core embodiment.
Figure 2C:
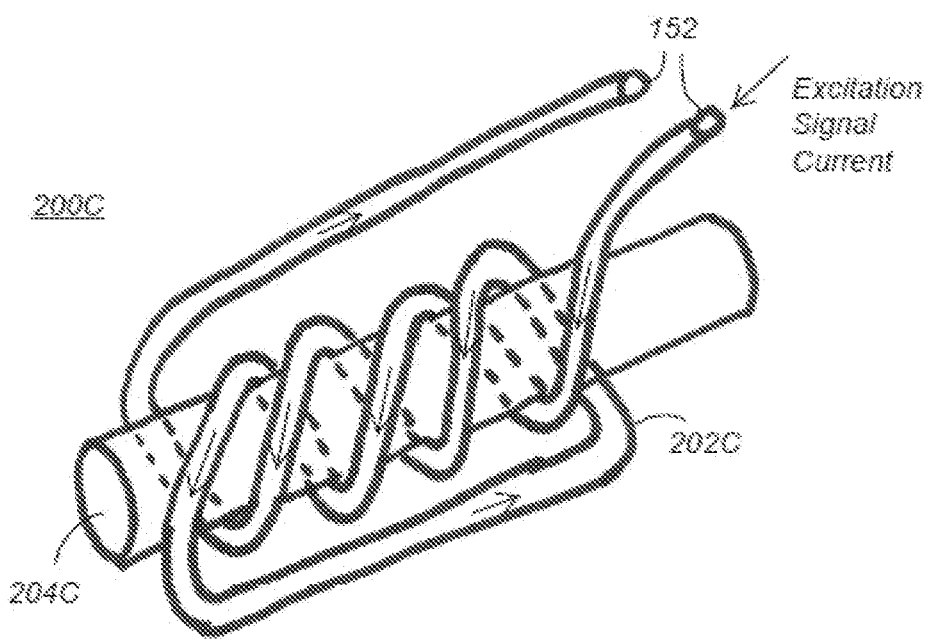
FIG. 2C illustrates an electromagnet, according to a second solid core embodiment.

In various ones of FIGS. 2B to 13 and the associated descriptions herein, electromagnet structure embodiments are shown and discussed. Particularly, FIG. 1 illustrates a representative electromagnet structure 200 comprising an inductor coil 202 and a core 204. Other embodiments sharing characteristics with the electromagnet structure 200 embodiment of FIG. 1 are shown and described elsewhere in present disclosure using distinguishing reference identifiers. For example, FIG. 2B illustrates an electromagnet structure 200B comprising an inductor coil 202B and a core 204B; FIG. 2C illustrates an electromagnet structure 200C comprising an inductor coil 202C and a core 204C; and so on.

It is understood by those of skill in the art that in order to simplify the present disclosure, any or all of the electromagnet structure embodiments may be referred to herein as electromagnet structure 200 comprising an inductor coil 202 and a core 204, and the various electromagnet structures, inductor coils, and cores along with their associated subcomponents, characteristics, and other properties may be used interchangeably amongst various embodiments. In cases where one or more distinguishing characteristics are clearly not at issue, the particular component or structure may use the reference number of any of the embodiments illustrated and described herein. In other cases, where such distinguishing characteristics are at issue or the context otherwise demands, the distinguishing characteristics will be identified and discussed.

For example, the electromagnet structure 200B of FIG. 2B is visually distinguishable from the electromagnet structure 200C of FIG. 2C. In cases where the coil winding density of a particular electromagnet structure under discussion is at issue, the particular inductor coil 202B or inductor coil 202C will be called out. In other cases where the coil winding density is not at issue, an inductor coil 202, an inductor coil 202B, or an inductor coil 202C may be identified, and the identified inductor coil represents any or all of the inductor coil embodiments illustrated in the figures and described in the text of the present disclosure and their reasonable equivalents. Accordingly, the substitution of one electromagnet structure or its associated features for another as disclosed herein is not limited to that which is expressly illustrated and described. Instead, such substitution is understood by those of ordinary skill in the art based on the context of use.

FIG. 2B is a low-frequency electromagnetic apparatus embodiment; i.e., an electromagnet structure 202B. The electromagnet structure 202B may be integrated with, or otherwise cooperatively arranged as part of, a medical instrument 102 (FIG. 1), according to one embodiment. The low-frequency electromagnetic apparatus embodiment (i.e., electromagnet structure 200B) substantially includes a core 204B and a conductive inductor coil 202B wound about the core 204B.

The inductor coil 202B includes a conductive wire or wire-like structure wound about the core 204B. The inductor coil 202B includes at least two inductor coil leads 152. The inductor coil 202B may be formed from an electrically conductive material such as copper. Other known materials to create an electromagnet may also be used. The control circuit 108 (FIG. 1) can apply an excitation signal to the inductor coil 202B by applying the excitation signal between the two inductor coil leads 152.

Inductor coil 202B in FIG. 2B is illustrated as a long, thin wire coated with a particular inductor coil insulating material 154. The inductor coil insulating material 154 that encapsulates the electrically conductive portion of inductor coil 202B may be an epoxy or another suitable insulating material. Inductor coil 202B may be laminated or unlaminated. That is, in some cases, the inductor coil insulating material 154 is optional.

Inductor coil 202B is illustrated as having a round cross-section with a particular inductor coil diameter 156. It is recognized that other forms and shapes for the inductor coil 202B are contemplated. For example, inductor coil 202B may be formed as a ribbon. Inductor coil 202B may have a rectangular cross-section, square cross section, or a cross-section having another shape. Inductor coil 202B may be segmented with different segments having different materials, different shapes, different sizes, or other different characteristics.

Core 204B is elongated relative to its diameter (inductor core diameter 158). Core 204B in FIG. 2B has a substantially circular cross-section with a particular inductor core diameter 158. A cross-sectional view of the electromagnet structure 200B is separately illustrated in FIG. 2B for ease in understanding the embodiment. It is recognized that other non-circular forms and shapes for an electromagnet core are contemplated, and some of these other embodiments are represented in the present disclosure. For example, in some cases, an electromagnet core may have a rectangular cross section, a square cross-section, a hexagonal cross section, or a cross-section with some other shape.

An electromagnet core may further include an optional laminate (not shown) or some other surface coating or the like. The surface coating may be an epoxy, a urethane, or another material. The surface coating may be materially, structurally, or materially and structurally arranged to increase adhesion of an inductor coil. For example, the surface coating may have a selected coefficient of friction, the surface coating may include ridges and valleys to receive an inductor coil, or the surface coating may have other properties along these lines.

The surface coating of an electromagnet core (not shown), like some or all other surfaces and materials of an electromagnet structure 200 that form an interface between part or all of the electromagnet structure 200 and biological tissue of a patient, may be arranged using bio-compatible materials. The bio-compatible materials may be selected to reduce or prevent irritation, inflammation, friction, bacterial growth, or other undesirable effects on a patient's body. In addition, or in contrast, the bio-compatible materials of a surface coating (not shown) of the electromagnet core, like some or all other surfaces and materials of an electromagnet structure 200, may be arranged to enhance desirable effects on a patient's body such as reduced diffusion, lubricity, abrasion and/or resistance, and the like. For example, one or more surface coatings of an electromagnet structure 200 may include a particular hydrophilic or hydrophobic polymer. The surface coatings of an electromagnet structure 200 in some cases are formed to be only a few nanometers thick and flexible to thereby reduce the instance of cracking or other failure, which may spread detrimental fragments inside the patient's body.

An electromagnet core may be solid, partially hollow, fully hollow (e.g., cylindrical; such as in a needle or stylet), or formed in some other way. In addition, an electromagnet core may be formed from a ferromagnetic material, a ferrimagnetic material, some other material having desirable magnetic characteristics. In some cases, an electromagnet core is formed from a generally non-physical material such as air, but it is has been learned that an air core device will generally require a much higher excitation frequency.

In FIG. 2B, the coils of inductor coil 202B are tightly wound around core 204B. The distance between the center of one coil and the center of an adjacent coil may be preferably controlled. In some cases, coils are tightly wound, and in other cases, coils are not tightly wound. The number of coils per unit measure 160 may be used to indicate how tightly wound the coils are in a particular embodiment of a low-frequency electromagnetic apparatus.

A conductor-wrapped-core length 162 may be controlled. The conductor-wrapped-core length 162 is generally the linear length of core 202B that is spanned by one or more coils of inductor coil 202B. The conductor-wrapped-core length 162 may determine particular electromagnetic properties of the electromagnet structure 200B.

An electromagnet structure length 164 may also contribute to particular electromagnetic properties of the low-frequency electromagnetic apparatus embodiment (i.e., electromagnet structure 200B). In addition, the electromagnet structure length 164 may also determine suitable applications for a particular trackable structure such as medical instrument 102 (FIG. 1).

Various electromagnet structure 200B embodiments have been constructed and tested in experiments. In some embodiments, the inductor coil diameter 156 is 0.001 inches. In some cases, the inductor coil diameter 156 is 0.0005 inches or less. Other diameters are contemplated, for example, the inductor coil diameter 156 may be between substantially about 0.00025 inches to 0.05 inches or some other range.

The inductor core diameter 158 in some experimental embodiments is about 0.010 inches. In other experimental embodiments, the inductor core diameter 158 is about 0.014 inches. The inductor core diameter 158 may be between substantially about 0.0005 inches and 0.250 inches. Different inductor core diameter 158 ranges are also contemplated. In many cases, the inductor core diameter 158 may be selected based on the particular application for the trackable structure (i.e., the electromagnet structure 202B of a particular medical instrument 102), the material used to form the core 204B, the material used to form the inductor coil 202B, and any combination of these and other factors. In some experimental embodiments, for example in the system 100 for detecting the position of a medical instrument within the body of a patient of FIG. 1, the inductor core diameter 158 (not to scale) is about 0.010 inches, the inductor coil diameter 156 (not to scale) is about 0.001 inches, the number of coils per unit measure 160 (e.g., the number of coils per inch) is about 1000, the conductor wrapped core length 162 is about two inches, and electromagnet structure length 164 is about three inches.

In other cases, for example, the electromagnet structure length 164 may be a different length. For example, in some cases, the core length 162 may be formed to be 20 inches long, 40 inches long, 60 inches long, or some other longer or shorter length. In these cases, one or more inductor coils 202B may be formed at any portion of the core. The one or more inductor coils 202B may be longer, shorter, or the same length as in any of cases described in the present disclosure. The one or more inductor coils 202B may be formed on a proximal end of the core 204B, the distal end of the core 204B, or some other portion of core 2046.

FIG. 2C illustrates an electromagnet, according to a second solid core embodiment. In the electromagnet structure 200C of FIG. 2C, a core 204C has a plurality of loosely wound coils formed as an inductor coil 202C, but one of skill in the art will recognize that in practice, inductor coils may be wound very tightly to overwrap very short linear lengths of core 204C or very long linear lengths of core 204C. The lengths, diameters, shapes, winding patterns, and other features of the electromagnet structure 200C may be formed to exhibit different electromagnetic properties from the electromagnet structure 200B of FIG. 2B or other electromagnet structures illustrated and described in the present disclosure.

In some cases, such as in the in electromagnet structure 200C of FIG. 2C, coils of inductor coil 202C may be over-wound, under-wound, knotted, knitted, entwined, woven, raveled, or otherwise formed in a self-binding arrangement. The self-binding arrangement may include particular knot structures such as a hitch (e.g., clove hitch, half hitch, and many others), a bowline, slip, figure-eight. In some cases, the self-binding structure may be sufficient to form the electromagnet structure 200C such that no adhesive or other binding agent is employed. In other cases, the self-binding structure may include an adhesive (e.g., glue, epoxy) over some or all of the inductor coil 202C. In at least one case, a single point of a binding agent is used to affix the inductor coil 202C to the core 204C. In these cases, the binding agent may be used to restrict movement of the inductor coil 202C, to act as a strain relief (e.g., at an inductor coil lead), or for some other reason.

The electromagnet structure 202C illustrates one technique of enhancing a magnetic field. In the structure of FIG. 2C, an excitation signal current will enter one of the inductor coil leads 152 as indicated by an arrow. The excitation signal current will travel through the inductor coil 202C in a certain direction indicated by arrows. Because the excitation signal current is traveling in the same direction in each coil winding, the magnetic field produced will be enhanced.

Figure 2D:
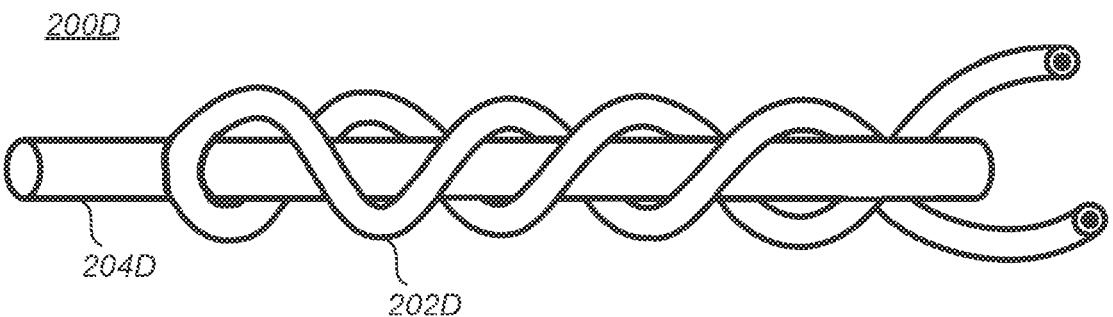
FIG. 2D illustrates an electromagnet, according to a third solid core embodiment.

FIG. 2D illustrates an electromagnet, according to a third solid core embodiment. In the electromagnet structure 200D of FIG. 2D, a core 204D has a differently wound set of coils formed from an inductor coil 202D. The magnetic field produced in the electromagnet structure 200D of FIG. 2D is presented in contrast to the electromagnet structure 200C of FIG. 2C. Rather than an enhanced magnetic field, the electromagnet structure 200D of FIG. 2D produces a canceling magnetic field because in adjacent windings of the inductor coil 202D, excitation signal current will flow in opposite directions. The two contrasting embodiments (i.e., enhancing electromagnet structure 200C and canceling electromagnet structure 200D) illustrate that one of skill in the art may design and electromagnet that produces a desired magnet strength. In this way, medical devices bearing one or more electromagnet structures may be formed with distinguishable properties (e.g., distinguishable signatures), distinguishable magnetic strengths, or other distinguishable characteristics.

The inductor coil 202D may be formed in a helical pattern, a double helical pattern, or some other non-imbricating pattern wherein the conductor of the inductor coil 202D does not overlap itself. Lengths, diameters, shapes, winding patterns, and other features of the electromagnet structure 200D of FIG. 2D may be formed to exhibit different electromagnetic properties from other low-frequency electromagnetic apparatus embodiments in the present disclosure.

In yet other embodiments electromagnet structures along the lines of electromagnet structure 200C and electromagnet structure 200D, conductors of the inductor coil 202C, 202D may overlap if fed in from the same direction, may not overlap if fed in from opposite directions, or may include another arrangement. For example, in some cases, the core 204C, 204D may also be used as a conductor. In this way, a first conductor lead may begin an inductor coil at a proximal end of the core and wrapped in a selected number of turns toward a distal end of the core. After completing the selected number of turns, the distal end of the conductor lead may be electrically coupled to the core itself, which in this case is formed from an electrically conductive material. In this case, a second conductor lead is electrically coupled to the proximal end of the electrically conductive core.

Figure 2E:
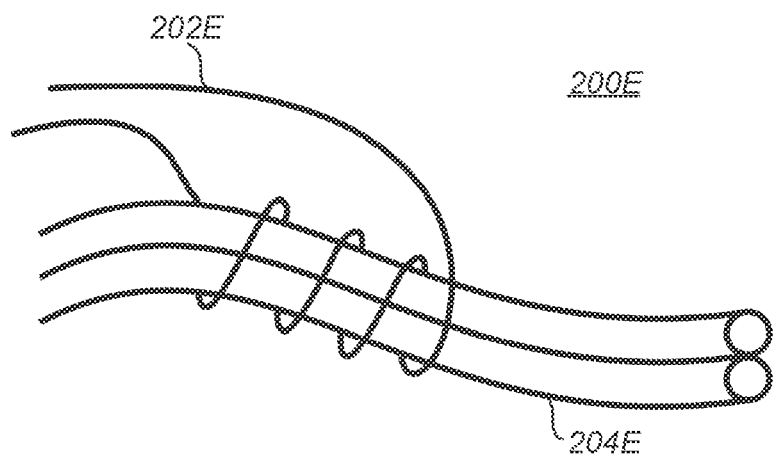
FIG. 2E illustrates an electromagnet, according to a multicore embodiment.

FIG. 2E illustrates an electromagnet, according to a multicore embodiment. The electromagnet structure 200E in FIG. 2E is a different low-frequency electromagnetic apparatus embodiment. In the embodiment of FIG. 2E, a core 204E is formed from a plurality of core segments having an inductor coil 202E wound about the core 204E. In the embodiment, two portions of core 204E are formed in parallel. Such an arrangement may permit a bias for bending in one plane while also resisting bending in a different plane.

In other embodiments, the core 204E of electromagnet structure 200E may include more than two portions. The multiple portions of the core 204E may each have the same structural characteristics, or in other cases, some or all of the portions may have different structural characteristics. For example, each portion may be formed having a substantially circular cross-section as illustrated in FIG. 2E. In other cases, one or more portions of core 204E have different cross-section shapes than one or more other portions.

Figure 2F:
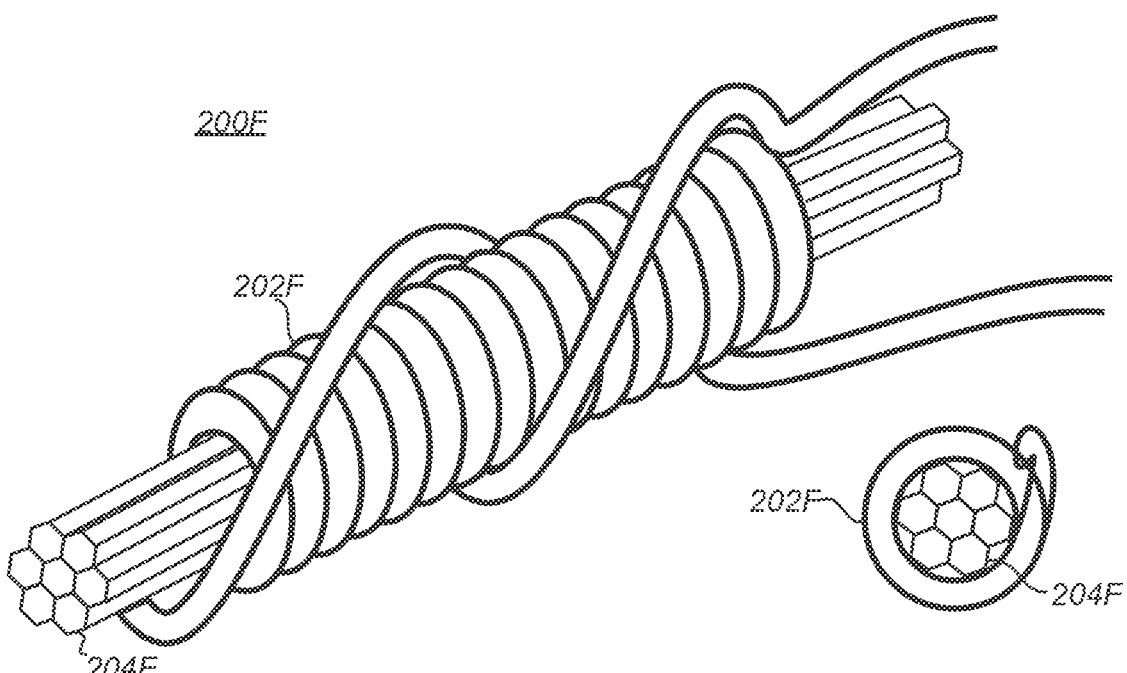
FIG. 2F illustrates an electromagnet, according to a sundered core embodiment.

FIG. 2F illustrates an electromagnet, according to a sundered core embodiment. The electromagnet structure 200F in FIG. 2F is another electromagnet embodiment that may also be interchangeably used in the medical instruments 102 or other apparatus described herein. In the embodiment, a core 204F is composed of a plurality of separate and distinct elements. The separate elements may be core wires, threads, bars, or any other linear form. An embodiment of the cross-section of the core 204F is also shown in FIG. 2F. Individual elements and the entire core 204F may be formed substantially as one or more of a circle, a square, a hexagon, or any other cross-sectional shape. In some cases, each element is insulated from other elements, for example using a coating, lamination, or the like. Forming a core 204F increases the surface area over which magnetic flux may be developed by improving the available area that electromagnetic energy from the coil windings may penetrate. Forming a core 204F may have other desirable properties including strength, rigidity, pliability, manufacturability, and other properties.

Inductor coil 202F may be formed in a desirable way as described in the present disclosure. For example, the inductor coil 202F is illustrated if FIG. 2F as a long, thin wire. The long thin wire may include an insulating material that fully or partially encapsulates the electrically conductive portion of the wire. The insulating material may be an epoxy or another suitable insulating material formed in a layer, a plurality of layers, or another suitable arrangement. The wire that makes up the inductor coil 202F is illustrated as having a round cross-section with a particular inductor coil diameter 156 (FIG. 2B). It is recognized that other forms and shapes for inductor coil 202F are contemplated. For example, the inductor coil 202F may be formed from a ribbon. The conductor that makes up the inductor coil 202F may have a rectangular cross-section, square cross section, or a cross-section having another shape. A particular shape may be chosen for ease in manufacturability, cost savings, increasing or decreasing surface area, or for other reasons.

The conductor of the inductor coil 202F may be laminated or unlaminated. The conductor may be segmented with different segments having different materials, different shapes, different sizes, or other different characteristics. The inductor coil 202F can be made from a conductor other than a wire, for example a thin film, a conductive ink, a conductive paint, or some other conductive material formed with a process not expressly described here for the sake of brevity.

Figure 2G:
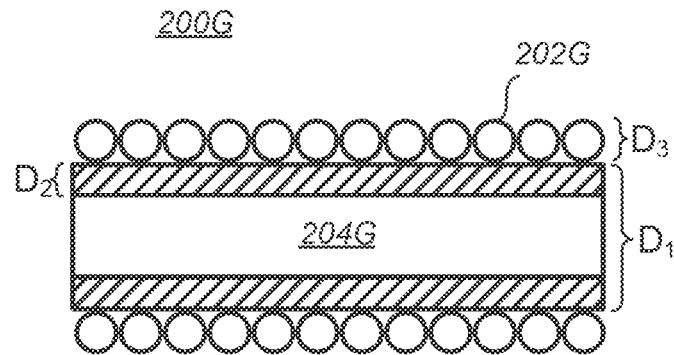
FIG. 2G is a cross-sectional diagram of an electromagnet illustrating the skin effect of magnetization of the core of the electromagnet, according to one embodiment.

FIG. 2G is a cross-sectional diagram of an electromagnet structure 200G illustrating the skin effect of magnetization of the core 204G of the electromagnet, according to one embodiment. In FIG. 2G, only a portion of the core 204G becomes magnetized. The magnetic field lines are not shown in FIG. 2G, but they are along the lines of those illustrated in FIG. 2A. In FIG. 2G, the core 204G has a diameter $D_1$. The magnetized portion of the core 204G has a diameter $D_2$, accentuated by crosshatching. The inductor coil 202G is formed of wire, and the wire of inductor coil 202G has a diameter $D_3$.

In FIG. 2G, the magnetization of only a portion of the core 204G adjacent to the surface of the core 204G is known as the skin effect. The depth to which the core 204G becomes magnetized is referred to as the skin depth. The skin depth $D_2$ increases with the magnitude of the driving current. The skin depth $D_2$ decreases with increasing frequency of the excitation signal. A deeper skin depth may be manifested as a stronger magnetic field, as a magnetic field that persists for a longer duration after the driving current (e.g., excitation signal) is removed, and in other ways.

A stronger magnetic field may be achieved by increasing magnetization of the core 204G. Full magnetization of the core can be achieved by appropriately selecting an inductor coil drive current, a driving frequency, an excitation signal waveform, dimensions, materials, and configuration of both the inductor coil 202G and the core 204G along with any laminations, coatings, and other such products of manufacturing. By carefully selecting these parameters, an increase of the magnetization of the core 204G, even to a point where the core 204G is considered to be fully magnetized, can be achieved.

In at least one embodiment, the inductor coil 202G includes a wire having a diameter less than 0.005". The wire can include a conductive material such as copper, aluminum, gold, alloys of one or more of these materials, or other conductive materials or alloys of other conductive materials. The wire can be coated in an insulating material. In at least one embodiment, the total diameter of the wire and its exterior coating is about 0.002". In other embodiments, for example in a peripherally inserted central catheter (PICC) embodiment, the total diameter of the wire and exterior coating is about 0.001".

In at least one embodiment, the core 204G includes a ferrous material such as steel, steel 1080, steel 1006, steel 1008, stainless steel, stainless steel 304V, iron, other alloys of iron, Permendur, Mu metal, ferrite or other ferrous materials. The core 204G can include other non-ferrous materials capable becoming magnetized. Alternatively, the core 204G can include a nonmagnetic material such as plastic, rubber, air, or other nonmagnetic materials.

In at least one embodiment, the core 204G is a wire. Thus, the electromagnet structure 200G can include a first wire acting as a core 204G, and a second wire wound about the core 204G acting as the inductor coil 202G. In at least one embodiment, the core 204G has a diameter less than 0.020" (e.g., 0.010"). In at least one embodiment, the core 204G has a diameter of about 0.005". Thus, in an example in which the inductor coil 202G includes a wire having a diameter of 0.002" and the core 204G includes a wire having a diameter of about 0.005", the total diameter of the electromagnet structure 200G is about 0.009".

In an electromagnet structure 200G, for example, the material that comprises the core 204G, along with the size, shape, and configuration of core 204G, are selected to have a particular relative permeability p within the electromagnet structure 200G. In some cases, the selected material will have a relative permeability p of 10,000 or higher. In addition to the parameters selected for core 204G, the parameters associated with inductor coil 202G are also selected to provide determined magnetic properties. The combination of the core 204G parameters and inductor coil 202G parameters will, in part, determine the strength, predictability, or other properties of the magnetic field (i.e., magnetic flux density B) along with the electrical parameters of the excitation signal.

For example, more current passed through the inductor coil 202G may increase the strength of the magnetic field, at least until the core 204G reaches saturation, but more current passed through inductor coil 202G may also generate additional, undesirable heat and possibly thermal breakdown of the conductor itself. In addition, reducing the cross-sectional area of the wire or other material that makes up the inductor coil 202G will also increase the resistance of the wire or other material that makes up the inductor coil 202G. Accordingly, as the electromagnet is reduced in size, more voltage may be required to overcome the increased resistance, and maintain an acceptable level of magnetic flux density B, though increasing voltage too much may cause the device to fail.

It has been learned in experimentation with certain embodiments discussed herein that by lowering the excitation frequency and choosing an appropriate core structure, the magnetic flux density B may be increased while the particular size of the low-frequency electromagnetic apparatus is reduced. The lower frequency excitation signal penetrates the appropriate core material more deeply, thereby producing an appreciable magnetic flux gain of tens, hundreds, or thousands of times higher than similar devices formed with an air core.

Accordingly, while known electromagnetic devices stimulated with an alternating current generally employ a higher frequency, the low-frequency employed by some embodiments in accordance with the present disclosure provide sufficient time for the generated magnetic field to more deeply penetrate the core material and increase the magnetic flux density B. In this way, the trackable structures discussed herein may be tracked more accurately and at greater distances with a magnetic field sensing device than previously known.

In the electromagnet structure 200G in FIG. 2G, and in other figures of the present disclosure, only a few windings of the inductor coil 202G around the core 204 are illustrated. In practice, however, inductor coil 202G and other inductor coils can include many more windings (e.g., tens, hundreds, thousands), and inductor coil 202G and other inductor coils can include multiple layers of windings. Those of skill in the art will recognize, in light of the present disclosure, that the inductor coil 202G and other inductor coils can include many other configurations than are shown in FIG. 2G, only some of which are described in the present disclosure. All such other configurations fall within the scope of the present disclosure.

FIGS. 2H to 2M are electromagnet structure embodiments 200H to 200M having various characteristics.

Figure 2H:
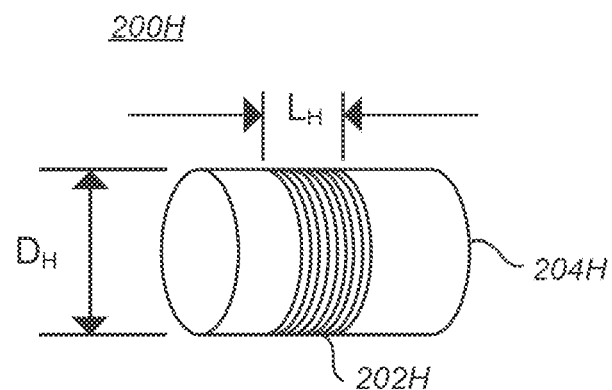
FIGS. 2H to 2M illustrate electromagnet embodiments having various characteristics.

In FIG. 2H, a core $204_H$ of an electromagnet structure 200H has a particular diameter $D_H$ and a particular set of inductor coil windings in its inductor coil $202_H$, which extend over a particular length $L_H$.

Figure 2I:
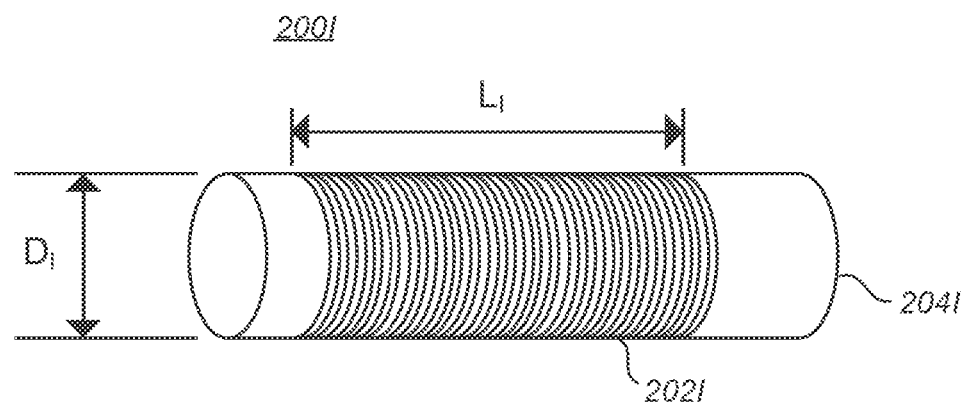

In FIG. 2I, an electromagnet structure 200I has a longer core $204_I$ (e.g., three or more inches), which has about the same diameter $D_I$ as in the electromagnet structure 200H embodiment of FIG. 2H, and includes more coil windings in inductor core coil 202, that extend over a longer distance $L_I$. The electromagnet structure 200I of embodiment of FIG. 2I may provide a stronger magnet or larger trackable magnet than the electromagnet structure 200H embodiment of FIG. 2H. Such an embodiment may be used with a very flexible medical instrument 102 (FIG. 1) embodiment that moves sharply around corners, with a medical instrument 102 that may otherwise be partially obstructed, or for other reasons.

Figure 2J:
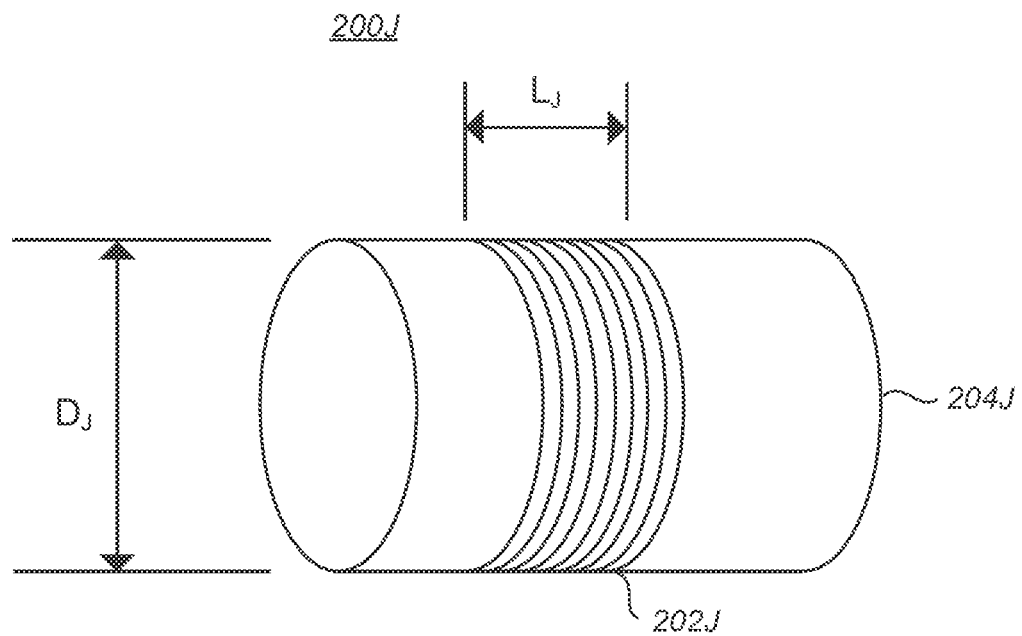

In FIG. 2J, a core $204_J$ of an electromagnet structure 200J has a large diameter $D_J 204_H$ (e.g., 0.25 inches or more). The electromagnet structure 200J embodiment of FIG. 2J also has a particular coil structure in an inductor coil $202_J$ that extends a particular length $L_J$ (e.g., 0.10 inches, 0.25 inches, one inch, or some other length). The electromagnet structure 200J embodiment of FIG. 2J may be used in large medical instruments, for example, those introduced orally and not venously.

Figure 2K:
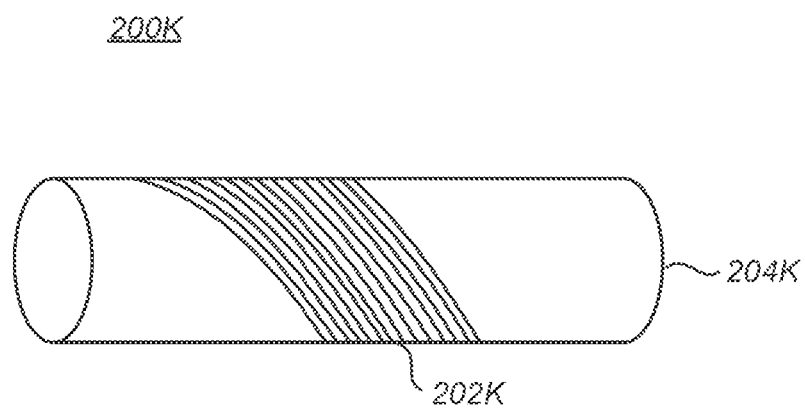
Figure 2L:
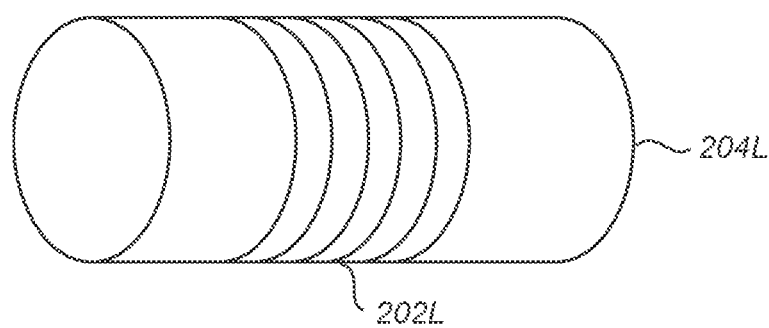
Figure 2M:
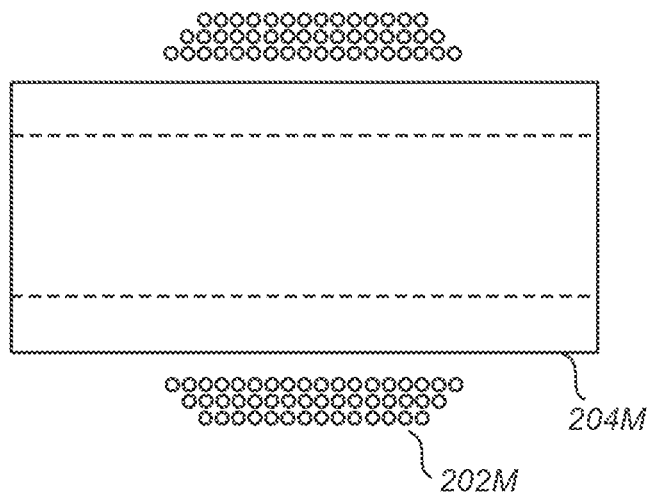

FIGS. 2K, 2L, and 2M illustrate still other electromagnet embodiments 200K, 200L, and 200M.

In FIG. 2K, an electromagnet structure 200K has a core $204_K$ that includes an inductor coil $202_K$ having very steeply oriented windings (e.g., 40°, 50°, 70°, or another angle), and in FIG. 2L, an electromagnet structure 200L has a core $204_L$ that includes an inductor coil $202_L$ having widely separated coil windings (e.g., coils separated by 0.002 inches, 0.010 inches, 0.05 inches, or some other distance).

In FIG. 2M, a cross-section of a core $204_M$ of an electromagnet structure 200M illustrates a multi-layered coil winding in an inductor coil $202_M$. Such embodiments may be provided for manufacturability, size, to create a particularly detectable electromagnetic signature, or for any other reason.

Figure 2N:
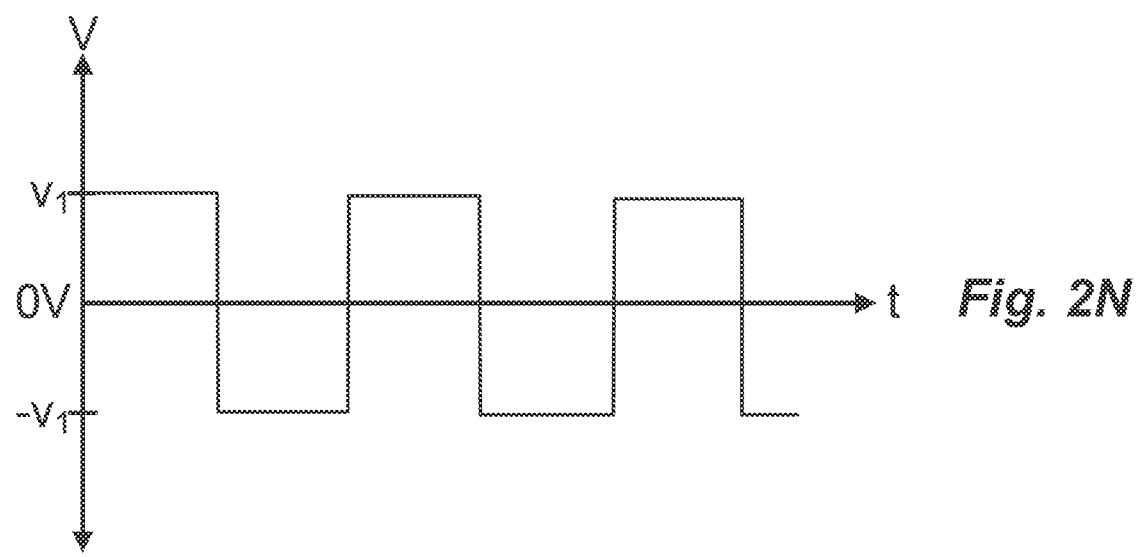
FIG. 2N is a graph of a square wave excitation signal that can be applied to an electromagnet, according to one embodiment.
Figure 2O:
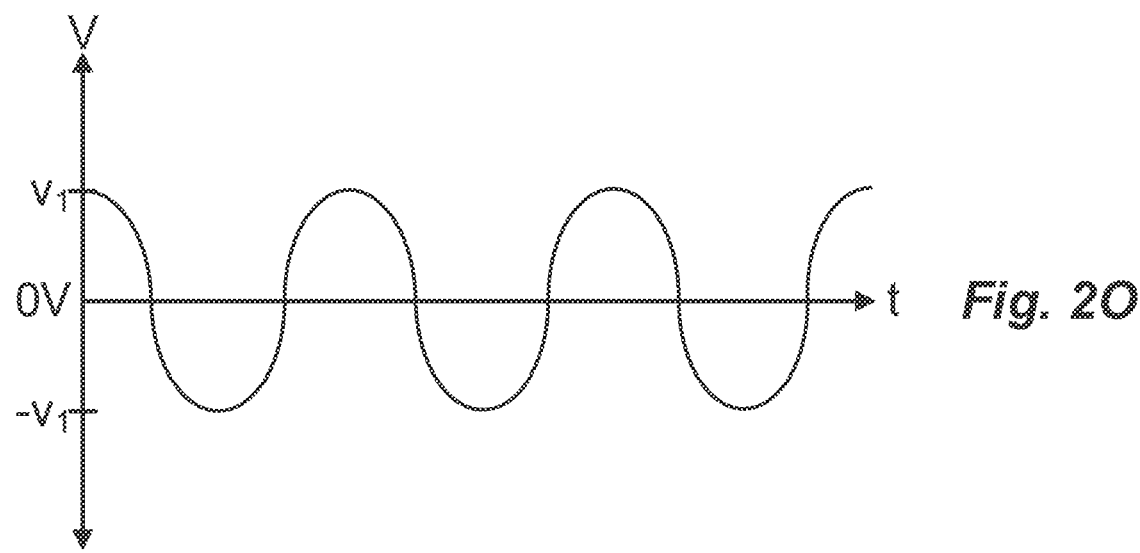
FIG. 2O is a graph of a sine wave excitation signal that can be applied to an electromagnet, according to one embodiment.
Figure 2P:
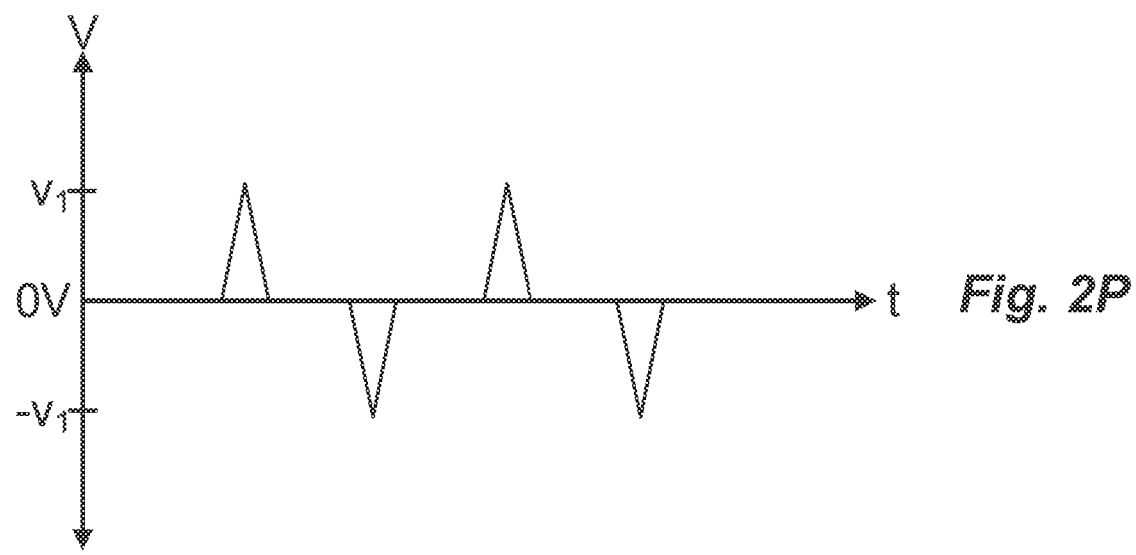
FIG. 2P is a graph of another excitation signal that can be applied to an electromagnet, according to one embodiment.

FIGS. 2N to 2P are several graphs illustrating several waveform embodiments of an excitation signal that can be applied, for example, to inductor coil leads 152 (FIG. 2B) of an inductor coil 202 (FIG. 2B). FIG. 2N is a graph of a square wave excitation signal that can be applied to an electromagnet structure 200, according to at least one embodiment. FIG. 2O is a graph of a sine wave excitation signal that can be applied to an electromagnet structure 200, according to at least one embodiment. FIG. 2P is a graph of another excitation signal that can be applied to an electromagnet structure 200, according to at least one embodiment.

In FIG. 2N, the excitation signal is a square wave that oscillates between $V_1$ and $-V_1$. In the graph of FIG. 2O, the excitation signal is a sinusoidal voltage that oscillates between $V_1$ and $-V_1$. In the graph of FIG. 2P, the represented excitation signal includes sharp voltage spikes that occur periodically and have peaks between $V_1$ and $-V_1$. In some cases, $V_1$ is a voltage of 2.5 volts, 5 volts, or another value. In some cases, $-V_1$ is a voltage of −2.5 volts, −5 volts, or another value. In FIGS. 2N to 2P, the reference voltage between $V_1$ and $-V_1$ is represented as zero volts, 0V. It is recognized, however, that the reference voltage of other embodiments may be above zero volts or below zero volts. In addition, it is further recognized that the absolute value of $V_1$ and $-V_1$ may be a different value. That is, in some embodiments, $V_1$ may be three volts and $-V_1$ may be minus two volts. Other different voltage values are also contemplated.

The excitation signals of FIGS. 2N to 2P are low-frequency excitation signal embodiments, which may be applied to opposing ends of a conductor of an inductor coil 202. The excitation signals of FIGS. 2N to 2P may have a frequency of about 300 Hz, 330 Hz, 500 Hz, or another frequency below 10,000 Hz.

In some cases, the excitation signals of FIGS. 2N to 2P are pulses in a particular pattern, for example an excitation signal identifier code, as opposed to a constant frequency. Pulses of the excitation signal in these embodiments may be phase shifted to modulate an identifiable code through a generated magnetic field. One excitation signal may have a different duty cycle than another excitation signal. For example, the excitation signal illustrated in FIG. 2O has a lower duty cycle than the excitation signal illustrated in FIG. 2N. Reducing a duty cycle may lower the operating temperature of a particular electromagnet structure 200 or provide other beneficial characteristics.

Different excitation signals for various low-frequency electromagnetic apparatus embodiments are also contemplated. The excitation signals may cycle at different frequencies, and the excitation signals may have different voltages. In some cases, the excitation signals cycle entirely above a ground plane, or entirely below a ground plane. In this way, it is recognized that the properties of an excitation signal generally include a reference voltage, a higher-going first signal portion rising to a first potential above the reference voltage, and a lower-going second signal portion falling to a second potential. In some cases, the reference voltage is zero volts. In other cases, the reference voltage is more than zero volts or less than zero volts.

When an excitation signal, for example one of the excitation signal embodiments of FIGS. 2N to 2P, is applied to an inductor coil 202 of a low-frequency electromagnetic apparatus (i.e., electromagnet structure 200), the electric current of the excitation signal produces a magnetic field about the low-frequency electromagnetic apparatus having particular properties. When the excitation signal rises toward the first potential above the reference voltage, the magnetic field forms with a first polarity; and when the excitation signal falls toward the second potential below the reference voltage, the magnetic field forms with a second polarity; the second polarity being opposite the first polarity. Accordingly, the magnetic field about the low-frequency electromagnetic apparatus will cycle between the first polarity and the second polarity, generally at the frequency or pattern of the excitation signal.

In some cases, the excitation signal is entirely positive or entirely negative. That is, in these cases, the reference voltage may not necessarily be centered at or around zero volts. For example, in some cases, an excitation signal may be formed between zero and ten volts wherein the reference potential is about five volts.

The excitation signals represented in FIGS. 2N and 2O may be better suited for a magnetically soft core structures, which can be magnetized easily but tend to lose their magnetic properties quickly. The excitation signal represented in FIG. 2P may be better suited for magnetically hard structures, which may also be magnetized easily and which may also tend to retain their magnetic properties for longer periods of time than soft magnetic materials. In cases where magnetically hard materials are used along with the excitation signal represented in FIG. 2P, a signal is applied and removed quickly, and in this way, the structure may be sensed with more assurance that the sensor is detecting the electromagnet structure 200 and not detecting any lead lines, which could exhibit magnetic properties when energized.

Figure 2Q:
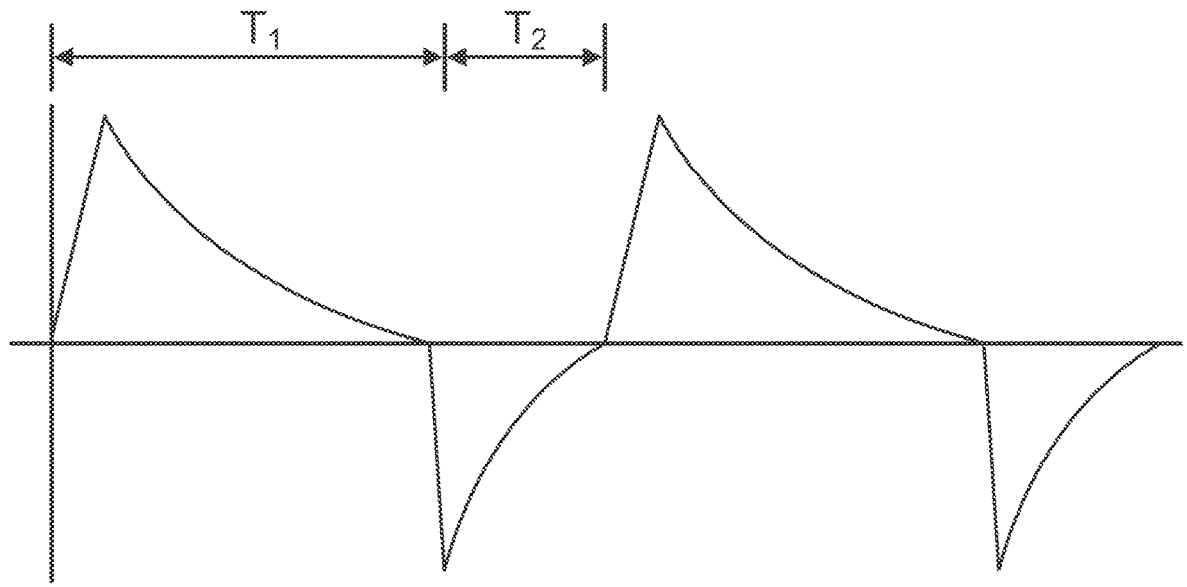
FIGS. 2Q and 2R are graphs of excitation signals having a plurality of different frequencies that can be applied to an electromagnet, according to other embodiments.
Figure 2R:
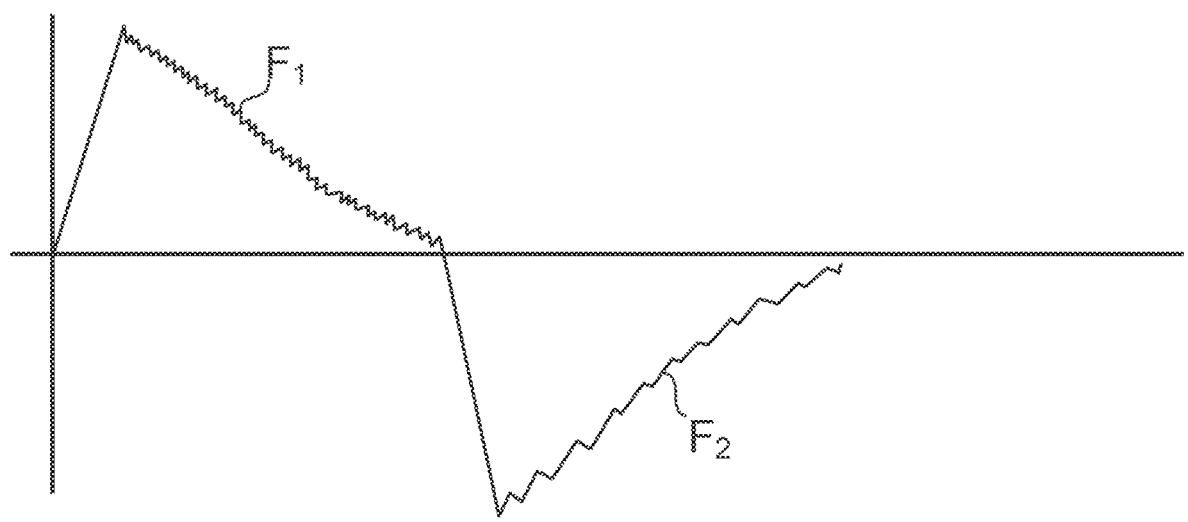

FIGS. 2Q and 2R are graphs of excitation signals having a plurality of different frequencies that can be applied to an inductor coil 202 of electromagnet structure 200, according to other embodiments such as embodiments that wirelessly excite the inductor coil 202 of an electromagnet structure 200. The excitation signals in these and other embodiments may be generated, for example, by a control circuit 108 (FIG. 1). In the embodiment of FIG. 2Q, the represented excitation signal has particular properties that permit a positive-going signal portion to have a first duration $T_1$ and a negative-going signal portion to have a second different duration $T_2$. The signal portions in FIG. 2Q may be formed by two different signals of different frequencies superimposed on each other, or the signal portions may be formed as a composite signal with the properties illustrated.

In the embodiment of FIG. 2R, a different type of composite signal is formed wherein a first signal portion, similarly shaped to the first signal portion of FIG. 2Q has a particular signal superimposed thereon having a first frequency $F_1$. The composite signal in FIG. 2R has a second signal portion similarly shaped to the second signal portion of FIG. 2Q, and another particular signal having a second frequency $F_2$ is superimposed on the second signal portion. The embodiment of FIG. 2R may be considered to conform to a particular frequency shift keying protocol. Information associated with one or both frequencies $F_1$ and $F_2$ may be used to convey an identification code, to better discern the generated magnetic field during a detection process or a tracking process, or for other reasons. For example, in some embodiments of FIGS. 2Q and 2R, each of the different signal portions used to energize the coil of an electromagnet may be used to distinguish one sensed electromagnet from another, may be used to distinguish a direction of motion, or may be used to distinguish other properties and characteristics. In some cases, sensed samples are stored, accumulated, and otherwise processed, and particular probability analysis is applied to the collected and determined sense data.

Figure 2S:
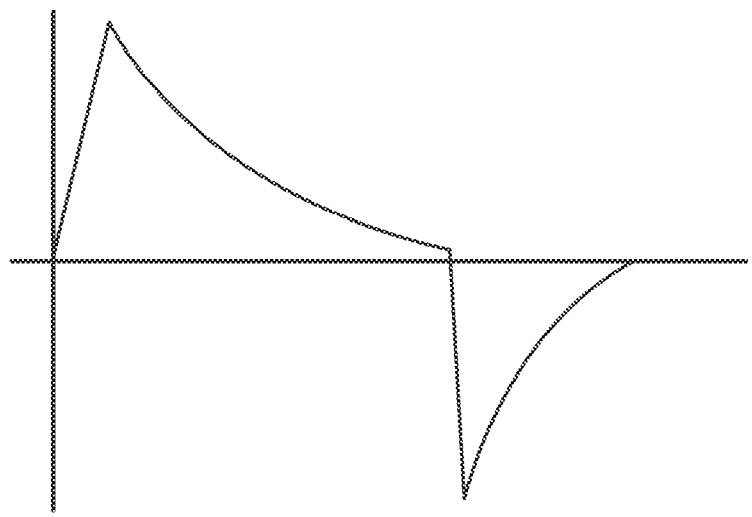
FIGS. 2S and 2T are graphs of an excitation signal and a correspondingly produced electromagnetic waveform.
Figure 2T:
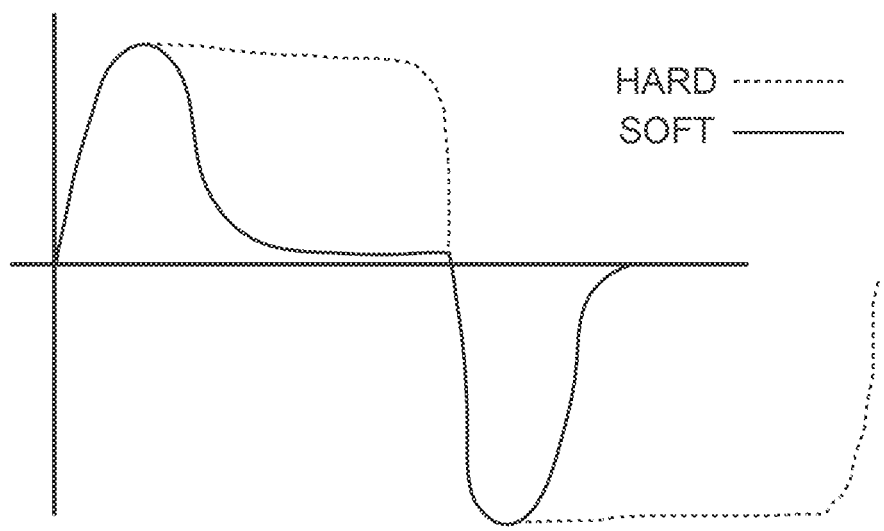

FIGS. 2S and 2T are graphs representing an excitation signal and a correspondingly produced electromagnetic waveform. The signal represented in FIG. 2S is arranged to rise sharply and to drift back toward its nominal value, and then drop sharply and drift back toward its nominal value. In the graph of FIG. 2S, the vertical axis represents voltage generated and the horizontal axis represents time. In the embodiment, a capacitor in a control circuit 108 (FIG. 1) is arranged in series with a signal line that sources the inductor coil 202 of an electromagnet structure 200. As a result of the capacitor, the signal actually applied to the inductor coil 202 as represented in FIG. 2S shows current sharply rising, or sharply falling as the case may be, and more slowly returning (e.g., drifting) back toward a nominal value.

In FIG. 2T, magnetic field information corresponding to the excitation signal of FIG. 2S is shown. The solid line in FIG. 2T represents an electromagnet structure having a core that does not hold a magnetic field for a very long time. For example, the core may have a very small diameter, or the core may be formed from a magnetically soft material. Conversely, the dashed line in FIG. 2T, represents a magnetic field that grows in strength an peaks at or about the same way that a small diameter or soft magnetic material core will, but when the core is formed from a magnetically hard material, the magnetic field will be sustained for a much longer time. The pattern of the magnetic field may appear as a square wave as in FIG. 2T, which generally collapses with a polarity shift in the excitation signal (FIG. 2S). Alternatively, the pattern of the magnetic field may drift lower or drop off in a different pattern.

In FIGS. 2S and 2T, it is recognized that the materials used to form the core of an electromagnet structure may be selected to produce a desirable magnetic field. For example, in some cases, the core is formed from a magnetically hard material such as stainless steel 1080. The stainless steel 1080 may be selected for many reasons. For example, stainless steel 1080 in the form of "piano wire" may be readily available in desirable commercial quantities, may be readily available at a commercially favorable price, may be reasonably shapeable for its selected diameter, may be sterilized and medically inert, and for other reasons.

Those of skill in the art will recognize, in light of the present disclosure, that other waveforms are possible for the excitation signal. For example, the excitation signal waveform can include a triangle wave, a sawtooth wave, DC offsets, variable frequencies and many other kinds of variations.

The form of the excitation signal affects the form of the AC current that flows through the inductor coil 202. The form of the AC current that flows through the inductor coil 202 affects the form of the magnetic field generated by the electromagnet structure 200.

In one embodiment, the alternating form of the magnetic field generated by the electromagnet structure 200 allows for increased ability to distinguish the magnetic field from various types of noise and electromagnetic interference. For example, if the control circuit 108 (FIG. 1) drives the inductor coil 202 with a particular excitation signal waveform, the control circuit 108 can more easily analyze the sensor signals generated by the sensor 104 (FIG. 1) to detect, identify, and track the expected varying form of the magnetic field generated by the electromagnet structure 200. These properties of the excitation signal, which improve the distinguishability of a generated magnetic field from undesirable interference or obfuscation, may also be used to distinguish one electromagnet from another. For example, in cases where two or more medical instruments 102 (FIG. 1) are deployed, each medical instrument 102 may be distinguished from each other medical instrument 102. In cases where an articulated, multi-part, or otherwise formed medical instrument 102 is used, different portions of the medical instrument 102 may have arranged therewith a separate electromagnet structure 200. In these cases, each portion of the medical instrument 102 may be separately distinguished from other portions during detection procedures, tracking procedures, and other location-based information procedures.

Figure 2U:
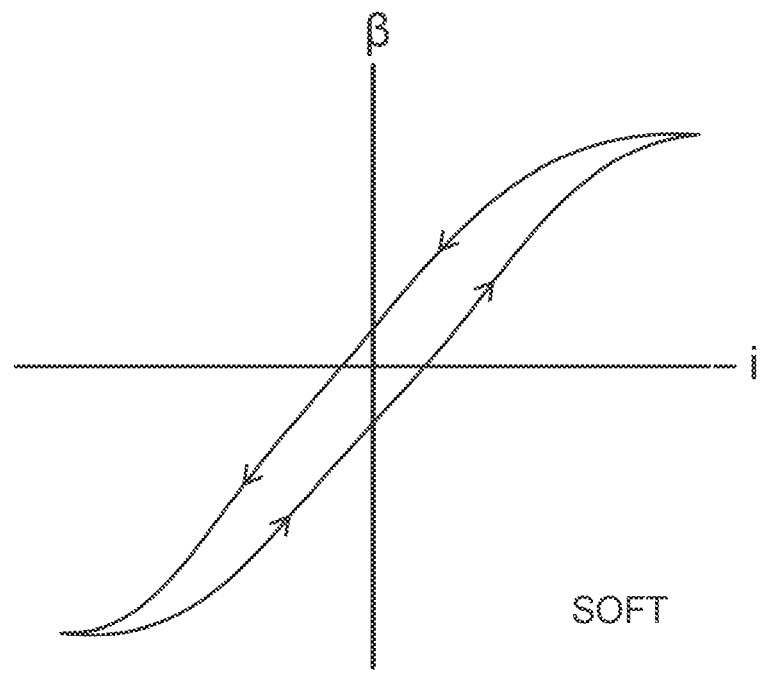
FIGS. 2U and 2V are graphs of magnetic flux density during one period of an excitation signal driving an electromagnet, according to particular embodiments.
Figure 2V:
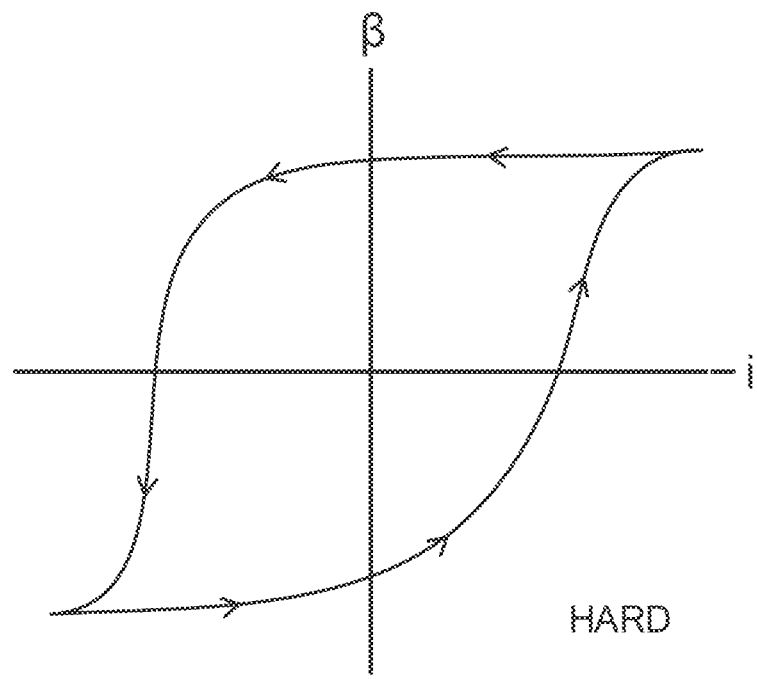

FIGS. 2U and 2V are graphs of magnetic flux density B, which may be used herein as a representative indication of magnetic field strength, during one period of an electromagnet embodiment being driven by a particular excitation signal. In FIG. 2U, the electromagnet structure 200 embodiment is characterized having soft magnetic properties, and in FIG. 2V, the electromagnet structure 200 embodiment is characterized having hard magnetic properties. Arrows on the graphs indicate the direction of time flow.

In the lower left corner of the graphs of FIGS. 2U and 2V, the excitation signal rises toward a first, upper voltage (e.g., $V_1$), causing current to also increase. As a result of the rising current, magnetic flux density B correspondingly rises in the direction of the arrows driving the core 204 of the electromagnet structure 200 toward saturation. The high point of magnetic flux density, which may be saturation, is indicated by the flat the top of each of the graphs in FIGS. 2U and 2V.

At the upper right corner of the respective graphs of FIGS. 2U and 2V, the excitation signal changes through a second, lower point (e.g., $-V_1$), causing the current to change direction and magnitude. The magnetic flux density B also decreases in the direction of the arrows until a particular value is reached, which may be a complete absence of magnetic flux or otherwise also called a negative saturation. The graphs of FIGS. 2U and 2V illustrate a certain hysteresis inherent in driving an electromagnet structure 200 with an oscillating excitation signal.

FIG. 3A is a low-frequency electromagnetic tracking system 100A. The low-frequency electromagnetic tracking system 100A may include components substantially along the lines of the system 100 for detecting the position of a medical instrument 102 within the body of a patient in FIG. 1. A patient 110 is undergoing a medical procedure. The patient may be a human patient or a non-human patient.

A medical practitioner (not shown) is administering the procedure. The medical practitioner has placed a trackable structure 102A, which may be embodied as a medical instrument, into the body of the patient 110. The trackable structure 102A may be a stylet, a catheter such as a Peripherally Inserted Central Catheter (PICC), a medical tube, a tracheal tube, a needle, a cannula, or some other structure. In some cases, the trackable structure 102A is a hollow tube-like device. In some cases, the trackable structure 102A is an elongated solid member. In some cases, the trackable structure 102A takes another form.

In FIG. 3A, the trackable structure 102A may be placed through the mouth of the patient 110 or through another of the patient's orifices. Alternatively, the trackable structure 102A may be placed through a surgical incision made by a medical practitioner at some location on the body of the patient 110. The trackable structure 102A may be placed and moved in other ways.

The trackable structure 102A has associated therewith a low-frequency electromagnetic apparatus such as an electromagnet structure 200. In some cases, the low-frequency electromagnetic apparatus is integrated with the trackable structure 102A. For example, when the trackable structure 102A is a stylet, the low-frequency electromagnetic apparatus may be formed as part of the stylet. In other cases, the low-frequency electromagnetic apparatus is fixedly or removably coupled to the trackable structure 102A.

A magnetic field sensing device 104A along the lines of sensor 104 (FIG. 1) is operated by a medical practitioner proximal to the body of the patient 110. In some cases, the medical practitioner places the magnetic field sensing device 104A directly in contact with the body of the patient 110. Generally speaking, the medical practitioner will attempt to place the magnetic field sensing device 104A adjacent to the portion of the body where the trackable structure 102A is believed to be.

A presentation system 106A, which may be along the lines of the input/output device 106 (FIG. 1) includes one or more of a video display, an audio input/output system, a tactile feedback system, or some other presentation mechanism. The presentation system 106A may further include one or more user input interfaces for keyboards, mice, touch screens, buttons, dials, and other like controls. The presentation system 106A provides input information to the magnetic field sensing device 104A and receives output information from the magnetic field sensing device 104A. Embodiments of the presentation system 106A are used to present information representing the position and orientation of a trackable structure 102A by receiving and processing magnetic field information provided by a low-frequency electromagnetic apparatus.

In some embodiments, the magnetic field sensing device 104A includes an electrical conduit 112A. The electrical conduit 112A may be used to pass power signals, control signals, data signals, or some other type of electrical signals. In the embodiment of FIG. 3A, the electrical conduit 112A is arranged to pass electrical signaling information to the low-frequency electromagnet structure 200. The electrical conduit 112A may pass electrical signals in a point-to-point arrangement, serial arrangement, parallel arrangement, networked arrangement, and alternatively, in some other arrangement.

The electrical conduit 112A may be used to pass signaling information between the magnetic field sensing device 104A and the presentation system 106A. The electrical conduit 112A may in addition or, in the alternative, pass signaling information between the magnetic field sensing device 104A and the low-frequency electromagnet structure 200. The signaling information may include power signals, control signals, data signals, or other signals.

In some embodiments, the magnetic field sensing device 104A may include one or more wireless transceivers arranged to communicate data between the magnetic field sensing device 104A and the presentation system 106A. In these and other embodiments, the magnetic field sensing device 104A may include one or more wireless transceivers arranged to wirelessly communicate information (e.g., information to generate a particular excitation signal) between the magnetic field sensing device 104A and the low-frequency electromagnet structure 200.

FIG. 3B illustrates a medical environment including a system 100B for detecting the position of a medical instrument within the body of a patient, according to at least one embodiment. In FIG. 3B, the system 100B is a low-frequency electromagnetic tracking system. A patient 110 is positioned on a bed (not shown) and receiving medical treatment. The medical instrument 102B is positioned within the body of the patient 110. A sensor 104B, which is along the lines of sensor 104 (FIG. 1) is positioned in proximity to (e.g., above) the patient 110. The sensor 104B includes an electrical conduit 112B by which the sensor 104B is electrically coupled to the medical instrument 102B and a display 106B. The display 106B may be along the lines of the input/output device 106 of FIG. 1.

The sensor 104B includes a control circuit 108 (FIG. 1) that generates an excitation signal, which is applied to an electromagnet structure (not shown) disposed on the medical instrument 102B. The excitation signal causes a current to flow through an inductor coil (not shown) of the electromagnet structure. The current causes the electromagnet structure to generate a magnetic field. The magnetic field varies in accordance with the waveform of the excitation signal.

Figure 4:
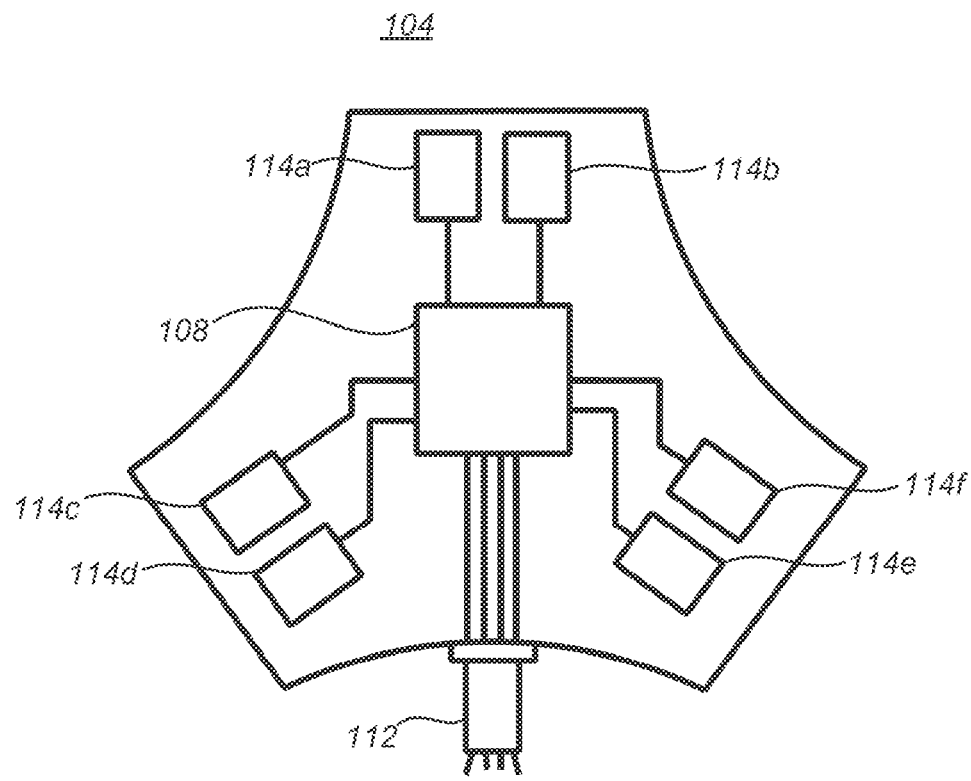
FIG. 4 illustrates a sensor housing including sensors and a control circuit, according to one embodiment.

The sensor 104B includes one or more magnetic sensors 114a-114f (FIG. 4). The one or more magnetic sensors 114a-114f are configured to detect the generated magnetic field and to output one or more corresponding sensor signals to the control circuit 108 (FIG. 1). The control circuit 108 analyzes the sensor signals from the one or more magnetic sensors 114a-114f and determines location-based information such as the position, orientation, and motion of the medical instrument 102B within the body of the patient 110. The determination of the location-based information is based on the sensor signals and the known characteristics of the excitation signal applied to the electromagnet structure.

In at least one embodiment, the control circuit 108 outputs a video signal to the display 106B. The display 106B receives the video signal and displays a representation of the position of the medical instrument 102B within the body of the patient 110. The video signal can include position data indicating position coordinates of the medical instrument 102B within the body of the patient 110. The display 106B displays the position data so that a medical practitioner, medical personnel, or other technicians can view the position data and the representation of the position of the medical instrument 102B in order to appropriately proceed with the medical procedure.

In at least one embodiment, the system 100B is operated by a medical practitioner. During operation, the medical practitioner positions the sensor 104B adjacent to, in direct contact with, or otherwise in proximity of the body of the patient 110. In some embodiments, the medical practitioner will attempt to place the sensor 104B adjacent to a region of the body where the medical instrument 102B is believed to be.

In at least one embodiment, the display 106B includes one or more of a video display, an audio input/output system, a tactile feedback system, signal lights, or some other presentation mechanism. Though not pictured in FIG. 3B, the system 100B can further include one or more user input systems configured to receive user input via keyboards, mice, touchscreens, buttons, dials, and other like controls.

In at least one embodiment, the control circuit 108 can output position data to one or more computing systems (e.g., an ultrasound device, a robotic surgical system) that control or manage aspects of the medical procedure. The one or more computing systems can adjust medical equipment in accordance with the position data. Additionally or alternatively, the computing system can output an alert indicating to medical personnel that there is a potential problem with the position of the medical instrument 102B within the body of the patient.

In some embodiments, the electrical conduit 112B may be used to pass power signals, control signals, data signals, or other types of electrical signals. The electrical conduit 112B may be arranged to pass electrical signaling information to the electromagnet structure disposed with the medical instrument 102B. The electrical conduit 112B may pass electrical signals in a point-to-point arrangement, a serial arrangement, a parallel arrangement, a network arrangement, and/or in some other suitable arrangement. In some cases, the electrical conduit 112B is comprised of wired means such as solid or stranded copper-based wire, wireless means such as a point-to-point or other wireless transceiver, or a combination of wired and wireless means.

The electrical conduit 112B may be used to pass signaling information between the sensor 104B and the display 106B. Additionally or alternatively, the electrical conduit 112B may pass information between the sensor 104B and the medical instrument 102B. The signaling information may include power signals, control signals, data signals, or other signals.

In one or more embodiments, the sensor 104B may include one or more wireless transceivers arranged to communicate data between various components of the electromagnetic systems described herein. For example, data or other signals may be wirelessly communicated between any or all of the sensor 104B, the display 106B, the control circuit 108, the medical instrument 102B, and other electronic systems that cooperate with these devices such as monitoring equipment, medical diagnostic equipment, and the like. In these and other embodiments, the sensor 104B may include one or more wireless transceivers arranged to communicate data between the components including the sensor 104B and the medical instrument 102B.

FIG. 4 illustrates a sensor 104. The sensor 104 is arranged in a housing with a plurality of magnetic sensors 114a-114f and a control circuit 108, according to at least one embodiment. The sensor 104 includes sensor portions comprising a plurality of magnetic sensors 114a-114f, a control circuit 108, and an electrical conduit 112. The control circuit 112 is coupled to the sensor portions and to the electrical conduit 112.

In at least one embodiment, the control circuit 108 outputs an excitation signal to an inductor coil 202 of an electromagnet structure 200 coupled to a medical instrument 102. The excitation signal causes the electromagnet structure 200 to generate a magnetic field as described in the present disclosure.

In the embodiment of FIG. 4, the sensor 104 includes six sensor portions, each sensor portion having at least one magnetic sensor 114a-114f. The six sensor portions are configured to collectively sense parameters of the generated magnetic field and other magnetic energy. The six sensor portions also generate sensor signals relative to the parameters of the generated magnetic field. Each of the sensor portions passes at least one sensor signal to the control circuit 108. The control circuit 108 analyzes the sensor signals and calculates position information associated with the medical instrument 102 based on the sensor signals. The calculated position information may include a position of the medical instrument 102 in three-dimensional space, a position of the medical instrument represented in two-dimensional space, an orientation of the medical instrument 102, motion of the medical instrument 102, and other position information. The sensor signals are indicative of the parameters of the magnetic field generated by the electromagnet structure 200 coupled to the medical instrument 102.

In some embodiments, in addition to the computing resources provided in the control circuit 108, additional and different computing resources are employed. For example, the control circuit 108 may provide preliminary collection, aggregation, or other processing of sensor data, and the control circuit 108 may communicate certain data (e.g., some or all of the collected, aggregated, and processed sensor data) to a remote computing device (not shown) such as a laptop computer, a cloud computing device, an ultrasound or other imaging medical equipment, or some other computing device. The remote computing device may provide additional processing to generate position data, video data, audio data, tactile data, image or other signal processing, and the like.

While FIG. 4 shows six sensor portions, the sensor 104 can include more or fewer individual sensor portions than shown in FIG. 4. Accordingly, the sensor 104 may also include more or fewer magnetic sensors 114a-114f and shown in FIG. 4.

In at least one embodiment, the magnetic sensors 114a-114f are configured to sense the magnitude of the generated magnetic field in all three spatial dimensions. For example, magnetic sensors 114a, 114b are configured to sense a magnitude of certain components the generated magnetic field along a first axis. Magnetic sensors 114c, 114d are configured to sense the magnitude of certain components of the generated magnetic field along a second axis orthogonal to the first axis. And magnetic sensors 114e, 114f are configured to sense a magnitude of certain components of the generated magnetic field along a third axis orthogonal to the first axis and the second axis.

In at least one embodiment, each pair of sensor portions provide a differential sensor signal in order to enhance accurate detection of the generated magnetic field along each of the three axes. For example, magnetic sensors 114a, 114b output sensor signals having opposite polarities. Magnetic sensors 114c, 114d output sensor signals having opposite polarities. And magnetic sensors 114e, 114f output sensor signals having opposite polarities. In this way, the six sensor portions enable accurate detection of parameters of the generated magnetic field in three spatial dimensions.

In at least one embodiment, the magnetic sensors 114a-114f include magnetoresistive sensors. The magnetoresistive sensors include materials whose electrical resistance varies in accordance with a magnetic field proximal to and sensed by the magnetoresistive sensors. In some cases, for example, magnetic sensors 114a-114f provide sufficiently accurate sense data to the control circuit 108 to detect and track with acceptable accuracy a medical instrument 102 that is in the body of a patient 110 when the sensor 104 is within 25 centimeters (cm) of the medical instrument 102. In some cases, magnetic sensors 114a-114f provide sufficiently accurate sense data to the control circuit 108 to detect and track with acceptable accuracy a medical instrument 102 that is in the body of a patient 110 when the sensor 104 is within 10 cm, 25 cm, 30 cm, 50 cm, 65 cm or some other even greater distance of the medical instrument 102. Such detection, tracking, and the determination of other position information is possible when the medical instrument 102 is arranged with an associated magnetic structure 200 and stimulated with an appropriate excitation signal as discussed in the present disclosure.

Each of the sensor portions can be configured to be sensitive to magnetic fields along a particular axis. The magnetic sensors 114a, 114b can be sensitive to magnetic fields along a first axis. The magnetic sensors 114c, 114d can be sensitive to magnetic fields along a second axis orthogonal to the first axis. The magnetic sensors 114e, 114f can be sensitive to magnetic fields along a third axis orthogonal to the first axis and the second axis. Thus, the three pairs of sensor portions are each configured to produce an electrical resistance that changes based on the strength of the targeted magnetic field in a particular direction.

In one embodiment, the magnetic sensors 114a-114f can include giant magnetoresistive (GMR) sensors. Additionally or alternatively, the magnetic sensors 114a-114f can include anisotropic magnetoresistance sensors, some other type of magnetoresistance sensors, or magnetic sensors based on another type of magnetic field measurement architecture.

In at least one embodiment, the sensor portions of FIG. 4 include one or more inductor coils. The inductor coils can be positioned and oriented to be sensitive to magnetic field components in respective spatial directions. The signal to noise ratio (SNR) scales according to Formula (1), $$(n^{(1/2)} * d^{(3/2)}) * (f * Bo) * (BW^{(-1/2)}) \quad (1)$$

wherein the particular parameters (e.g., size, diameter) of wire used to make the sensing coils is fixed. In Formula (1), the first two parameters are linked to the geometry of the sensing coil: "n" is the number of turns, "d" is the diameter of the coil. Also in Formula (1), the second two parameters are directly limited by the characteristics of the electromagnet structure 200: "f" is the frequency of oscillation, "Bo" is the field that the electromagnet structure 200 can support. Further still in Formula (1), BW is the filtered bandwidth, for example, an update rate of 3-30 Hz.

Still considering Formula (1), if the sensing coil is grown to 1 cm diameter then a factor of 2× improvement in SNR (200 turns) (+26% range) may be realized. Increasing the wire gauge or number of turns could further improve SNR (albeit slowly, 10× more turns=+47% range) assuming that environmental noise and coil resonance doesn't limit the sensitivity. In one embodiment, the circuitry in the sensor 104 can allow detection and generation of position information of the medical instrument 102 up to 65 cm away from the sensor 104 with acceptable accuracy.

An additional consideration in the sensor 104 that includes the sensor portions and the control circuit 108 is the limited space available within the housing of the sensor 104. The limited space within the housing may dictate that relatively small inductor coils be used in magnetic sensors 114a-114f. If the size of the sensor housing is increased, such as if very large inductor coils are used, for example, then there can be complications due to parasitic capacitance of the coils. This can possibly result in a natural resonant frequency and the potential to generate excessively large signals to later be filtered off. In at least one embodiment, the sensor portions can include a magnetic gain medium (e.g., ferromagnetic cores within the sensor coils). A magnetic gain medium can help to improve the SNR of the magnetic sensors 114a-114f. Furthermore, the size of gain media can be a limiting factor. For example, increasing the size of the sensor coils and the gain media may lead to increasing interference between adjacent sensing coils. In this way, the sensor 104 may provide a balanced geometry, which is a geometry that considers sizes, materials, distances between, orientations, and other such parameters of components of the sensor portions.

In at least one embodiment, the sensor portions include permanent magnets.

The sensor portions of FIG. 4 that include magnetic sensors 114a-114f are arranged to pass sensor signals to the control circuit 108. The control circuit 108 receives the sensor signals and analyzes the sensor signals. The control circuit 108 determines location-based information associated with the medical instrument 102 within the body of the patient 110 based on the sensor signals. The control circuit 108 can output any or all of a video signal, an audio signal, a tactile signal, or any other user or machine-perceptible signal indicative of or otherwise representing some or all of the location-based information. The location-based information may represent position data indicating the position of the medical instrument 102 within the body of the patient 110, an orientation of the medical instrument 102 relative to one or more reference points (e.g., a structure in or about the patient's body, a point on the sensor housing, and the like), actual or relative movement of the medical instrument 102, a historical track of previous positions of the medical instrument 102, a predicted track of the future position of the medical instrument 102, a velocity or other rate of motion information, and other like information associated with the medical instrument 102. In some cases, at least some of the location-based information is represented by a time-varying signal such as an audio signal of varying frequency to represent speed, distance, proximity to another structure, or the like. In some cases, at least some of the location-based information is represented by color or grayscale (e.g., lighter colors representing further distance and bolder colors representing closer distance). Many other representations are also contemplated.

In one embodiment, the sensor 104 can output data signals, control signals, excitation signals, power signals, or other types of signals via the electrical conduit 112. In particular, the sensor 104 can output signals to the electromagnet structure 200 of the medical instrument 102 and/or to an input/output device 106. The sensor 104 can also receive signals from the electromagnet structure 200, the input/output device 106, and/or additional electronic equipment via the electrical conduit 112.

In at least one embodiment, the sensor 104 includes one or more wireless transmitters and/or receivers (not shown). Sensor 104 can transmit, receive, or transmit and receive wireless signals from one or more wireless transmitters and/or receivers. In particular, wireless transmitters and receivers (e.g., transceivers) can transmit and receive signals to and from the electromagnet structure 200 and the input/output device 106.

Figure 5:
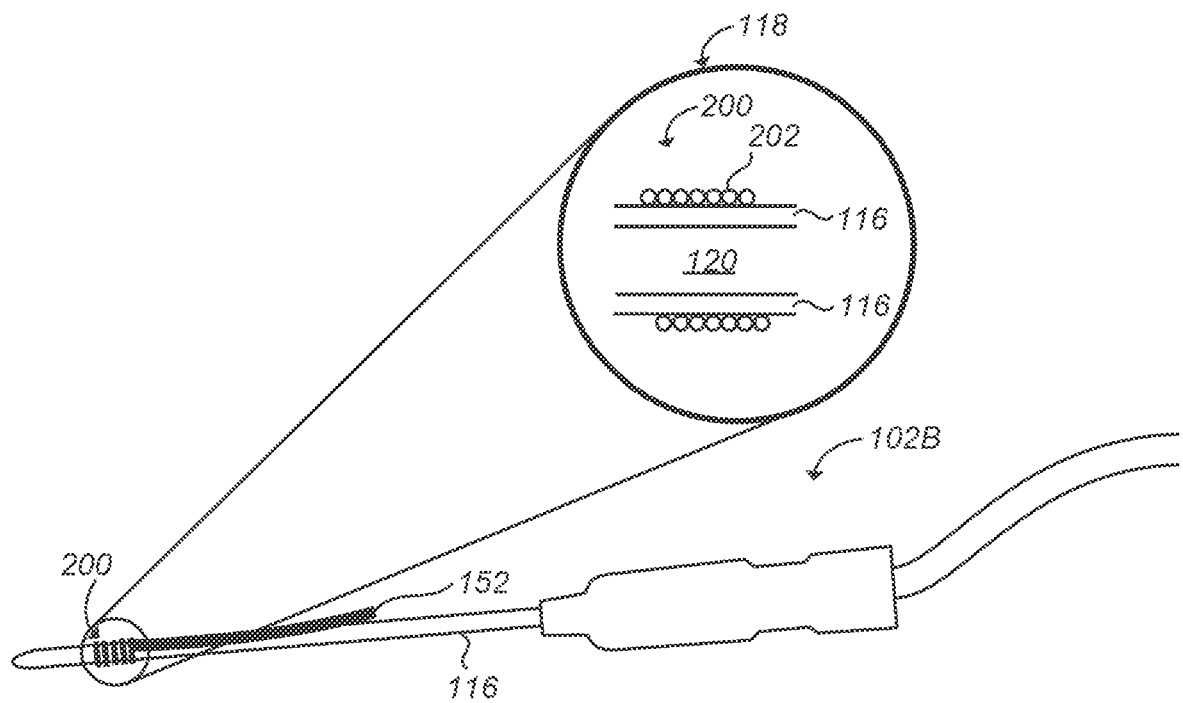
FIG. 5 illustrates a medical instrument including an intravenous needle, according to one embodiment.

FIG. 5 is an illustration of a medical instrument 102B, according to one embodiment. The medical instrument 102B of FIG. 5 is integrated with an intravenous fluid delivery apparatus configured to deliver a fluid to a patient.

The intravenous fluid delivery apparatus includes a needle 116. The tip of the needle 116 is configured to be introduced into the body of the patient. The tip of the needle 116 includes a sharp point suitable for penetrating the skin and other tissue of the body of the patient 110 in order to deliver a fluid to a selected area of the body.

An electromagnet structure 200 is positioned near the tip of the needle 116. The electromagnet structure 200 includes an inductor coil 202 wound about a core 204. One, two, or more inductor coil leads 152 are connected to the inductor coil 202. The inductor coil leads 152 enable a low-frequency excitation signal to be applied to the inductor coil 202 of the electromagnet structure 200.

FIG. 5 includes an enlarged cross-sectional diagram 118 of the electromagnet structure 200 of the medical instrument 102B. The inductor coil 202 includes a wire that is wound multiple times around a portion of the needle 116. As indicated in the enlarged cross-sectional diagram, a portion of the needle 116 is used as the core 202 of the electromagnet structure 200. That is, the portion of the needle 116 having conductive wire wound there-around corresponds to the core 204 of the electromagnet structure 200. Because the needle 116 is generally formed as a tube that delivers a fluid to the body of the patient 110, a fluid channel 120 is positioned within the core 204.

In one embodiment, the control circuit 108 (FIGS. 1, 4) or a voltage source or a current source controlled by the control circuit 108 is configured to apply a low-frequency excitation signal across the inductor coil 202 via the inductor coil leads 152. The excitation signal causes current to flow through the inductor coil 202 that is wound around the core 204. As the current flows through the windings of the inductor coil 202, a magnetic field is generated in and about the electromagnet structure 200.

In one embodiment, the magnetic field generated by the electromagnet structure 200 enables tracking of the position of the tip of the intravenous needle 116 within the body of the patient 110. In particular, a sensor 104 (FIG. 1) positioned external to the body of the patient 110 can detect certain parameters of the generated magnetic field, and the sensor 104 can generate sensor signals indicative of the position of the electromagnet structure 200 (e.g., the tip) of the needle 116 within the body of the patient. In one embodiment, the electromagnet structure 200 is positioned adjacent to the tip of the needle 116. In particular, the electromagnet structure 200 is positioned a known distance from the tip of the needle 116 so that the position of the tip of the needle 116 can be calculated based on the position of the electromagnet structure 200 or position information associated with the electromagnet structure 200.

In one embodiment, the inductor coil 202 of the electromagnet structure 200 includes dozens or hundreds of windings along a 5 cm length of the needle 116. The portion of the needle 116 covered by windings of the inductor coil 202 can be selected based on the desired sensing parameters and/or constraints based on the patient-tolerable intrusiveness of the electromagnet structure 200 on the medical instrument 102. The inductor coil 202 can include a single layer of windings or multiple layers of windings.

Figure 6:
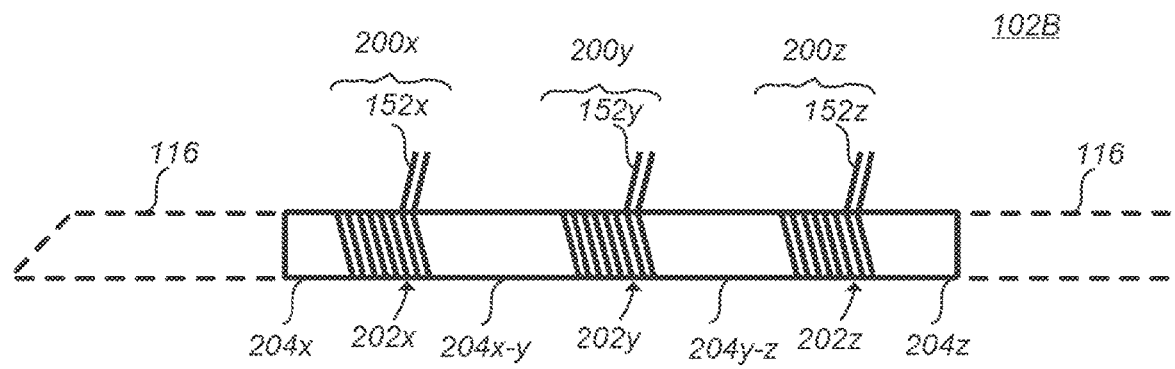
FIG. 6 illustrates a portion of a medical instrument including multiple electromagnets, according to one embodiment.

FIG. 6 is an illustration of a portion of a medical instrument 102b including multiple electromagnet structures 200x to 200z, according to at least one embodiment. Each electromagnet structure 200x to 200z includes a respective inductor coil 202x, 202y, 202z wound around a portion of a needle 116 or stylet. For ease in understanding the illustration, the portion of the needle 116 between 204x and 204x-y form a core for the first electromagnet structure 200x, the portion of the needle 116 between 204x-y and 204y-z form a core for the second electromagnet structure 200y, and the portion of the needle 116 between 204y-z and 204z form a core for the third electromagnet structure 200z.

Each of the inductor coils 202x, 202y, and 202z can be driven by the control circuit 108 with a low-frequency excitation signal passed through respective sets of conductive leads 152x, 152y, 152z. The control circuit 108 can drive each electromagnet structure 200x, 200y, 200z with the same excitation signal. Alternatively, the control circuit 108 can drive each electromagnet structure 200x, 200y, 200z with an excitation signal that is different and distinct by way of frequency, phase, pattern, or some other parameter or parameters. For example, each of the excitation signals can be identical but mutually out of phase with each other. Driving multiple electromagnet structures 200x, 200y, 200z in this manner can improve the ability of the sensor 104 and the control circuit 108 to detect each magnetic field and calculate the position of one or more medical instruments 102 with acceptable accuracy within the body of the patient 110.

In at least one embodiment, one or more of the electromagnet structures 200x, 200y, 200z are positioned on the medical instrument 102B such that the one or more electromagnet structures 200x, 200y, 200z are internal to the body of the patient 110 during a medical procedure. Additionally, one or more of the electromagnet structures 200x, 200y, 200z are positioned on the medical instrument 102B such that the one or more electromagnet structures 200x, 200y, 200z are positioned external to the body of the patient 110 during a medical procedure.

In the embodiment of FIG. 6, a needle 116 or stylet has a plurality of inductor coils 202x, 202y, 202z formed thereon. The needle 116 or stylet may be formed as a single common core, or a core may be formed from two or more portions of core material as discussed herein. Each portion of the core may be formed from the same material or from different material. In one embodiment, a core may be formed from a plurality of core segments.

Figure 7:
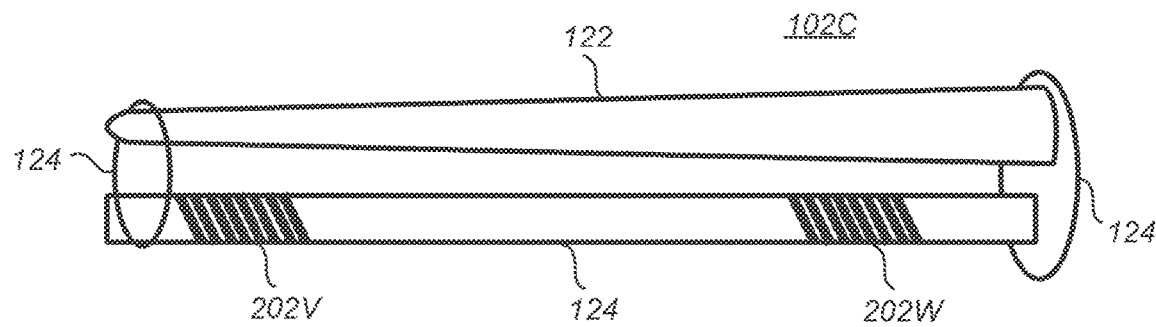
FIG. 7 illustrates a medical instrument including a medical implant, according to one embodiment.

FIG. 7 is an illustration of a medical instrument 102C, according to at least one embodiment. The medical instrument 102C includes a medical implant 122 configured to be implanted within the body of the patient 110. The medical instrument 102C also includes a stiffener structure 124 coupled to the medical implant 122 by connectors 124 and configured to assist in delivering the medical implant 122 to a selected position within the body of the patient 110.

In one embodiment, the stiffener structure 124 includes electromagnet structures 200V, 200W. The electromagnet structures 200V, 200W include, respectively, an inductor coil 202V, 202W wound about particular portions of the stiffener structure 124. In this case, the stiffener structure 124 is arranged with material suitable for forming a core of the electromagnet structures 200V, 200W. The electromagnet structures 200V, 200W are configured to be driven with a low-frequency excitation signal by a control circuit 108 as described herein. The electromagnet structures 200V, 200W each generate a magnetic field when driven with the low-frequency excitation signal.

In at least one embodiment, as the medical instrument 102C is introduced into the body of the patient 110, a sensor 104 detects each generated magnetic field and generates commensurate sensor signals. The control circuit 108 receives the sensor signals and calculates the position of the medical instrument 102C within the body of the patient 110 based on the sensor signals. When the medical instrument 102C is at the selected position within the body of the patient 110, the stiffener structure 124 can be unbound from the medical implant 122 and the medical implant 122 is implanted within the body of the patient 110 at the selected position.

In one embodiment, the medical implant 122 is a cochlear implant configured to be implanted into the cochlea of an ear of the patient 110. The medical implant 122 is a pre-stressed implant such that when the medical implant 122 is liberated from the stiffener structure 124 at the proper location, the cochlear implant coils within the cochlea in accordance with the shape of the cochlea. The stiffener structure 124 is withdrawn from the patient's ear and the cochlear implant remains positioned within the cochlea the human ear.

The medical implant 122 can include a heart rate monitor, a pacemaker, a diagnostic tool, a stent, a screw, a plate, a breast implant, or any other type of medical device (e.g., medical instrument) that can be implanted in the body of a patient 110 as part of a medical procedure. Those of skill in the art will recognize, in light of the present disclosure, that the medical implant 122 can include many other kinds of medical devices (e.g., medical instruments 102).

Figure 8:
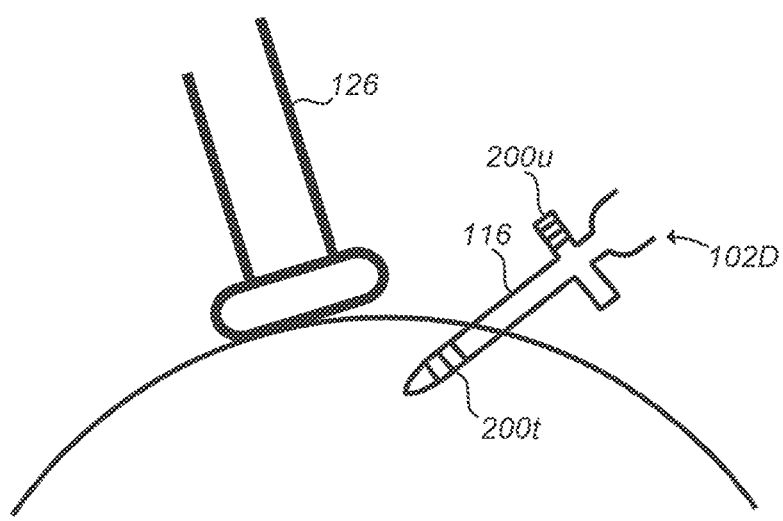
FIG. 8 illustrates a medical procedure including ultrasound imaging and the insertion of a medical instrument into the body of a patient, according to one embodiment.

FIG. 8 illustrates a medical procedure including ultrasound imaging and the insertion of a medical instrument 102D into the body of a patient 110, according to at least one embodiment. FIG. 8 is an illustration of a medical environment in which a pregnant patient is receiving a medical procedure. An ultrasound device 126 performs ultrasound imaging on the patient 110 in an area relating to the uterus where the fetus is growing. A medical instrument 102D (e.g., an amniocentesis needle) is delivering treatment to the uterus and/or the fetus. Due to the extreme sensitivity of such a procedure, which may for example damage the fetus if improperly conducted, it is very advantageous to know the position of the medical instrument 102D with acceptable accuracy in relation to the fetus.

Accordingly, the medical instrument 102D includes a first electromagnet structure 200t near the tip of a needle 116 of the medical instrument 102D. The medical instrument 102D also includes a second electromagnet structure 200u positioned in a direction orthogonal to the first electromagnet structure 200t. The electromagnet structures 200t, 200u are driven by the control circuit 108 in order to produce magnetic fields. Sensor 104 and the control circuit 108 cooperate to collectively detect the magnetic fields generated by the electromagnet structures 200t, 200u and calculate the position of the medical instrument 102D within the body of the patient 110. Selectively positioning two orthogonal electromagnet structures 200t, 200u in this way may in some cases improve the accuracy of sensing motion and rotation of the medical instrument 102D.

In at least one embodiment, the control circuit 108 can cause the input/output device 106 to display the ultrasound image as well as the position of the medical instrument 102D superimposed on the ultrasound image. The medical instrument 102D is partially or fully undetectable by the ultrasound imaging device 126. However, because the control circuit 108 can calculate a position of the medical instrument 102D within the body of the patient 110, the control circuit 108 can output a video signal to the input/output device 106 causing the input/output device 106 to present (e.g., display) the ultrasound image with the position of the medical instrument 102D superimposed thereon so that a medical practitioner can see the exact position of the medical instrument 102D with acceptable accuracy within the patient 110 and avoid damaging the fetus or sensitive areas of the body of the patient 110.

Figure 9A:
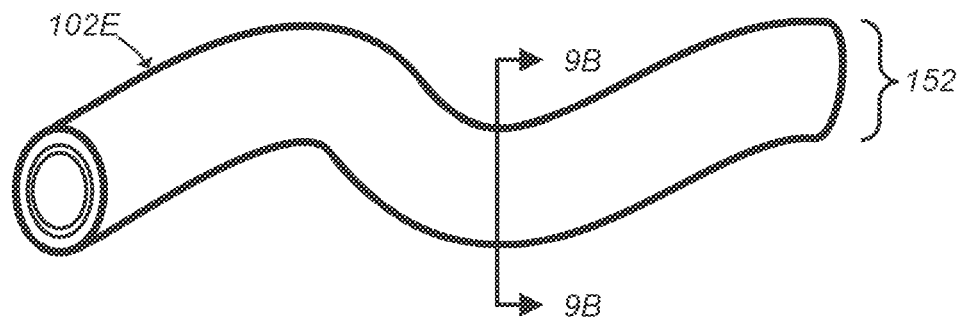
FIG. 9A illustrates a flexible medical instrument configured to be introduced into the body of a patient, according to one embodiment.

FIG. 9A is an illustration of a flexible medical instrument 102E configured to be positioned within the body of a patient 110, according to at least one embodiment. In at least one embodiment, the medical instrument 102E of FIG. 9A is a catheter configured to remove fluid from the body of the patient. Alternatively, the medical instrument 102E can be a feeding tube or some other type of tube configured to deliver or remove fluid from the body of the patient 110.

Figure 9B:
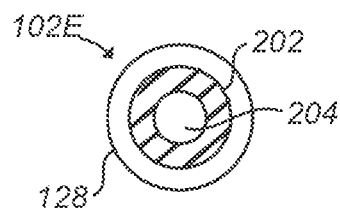
FIG. 9B is a cross-sectional diagram of the flexible medical instrument of FIG. 9A, according to one embodiment.

FIG. 9B is a cross-sectional diagram of the flexible medical instrument 102E of FIG. 9A, according to at least one embodiment. The cross-sectional diagram of the medical instrument 102E in FIG. 9B is taken along cross-sectional lines 9B. The medical instrument 102E includes an inductor coil 202 wound about a core 204. A protective outer coating 128 surrounds the inductor coil 202. The control circuit 108 can apply the low-frequency excitation signal across the inductor coil 202 via the inductor coil leads 152. The core 204 can include a shell defining a fluid channel or lumen (not shown). In these cases, the medical instrument 102E is hollow, which permits a medical practitioner to introduce fluids, tools, or other therapeutic agents and devices to a known site in the patient's body. Sensors 104 and a control circuit 108 can collectively and cooperatively detect and calculate position information of the medical instrument 102E within the body of the patient 110. In at least one embodiment, the core 204 is flexible. Alternatively, the core 204 can be stiff while other portions of the medical instrument 102E are flexible.

Figure 10:
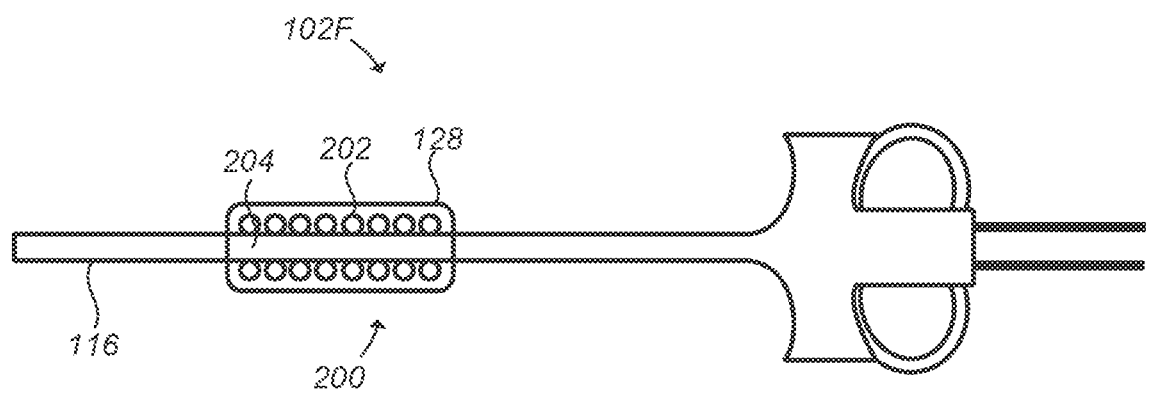
FIG. 10 illustrates a medical instrument including an electromagnet covered by a biocompatible insulating material, according to one embodiment.

FIG. 10 illustrates a medical instrument 102F including an electromagnet structure 200 covered by a biocompatible insulating material 128, according to one embodiment. In FIG. 10, the medical instrument 102F is configured to be positioned within the body of a patient, according to at least one embodiment. The medical instrument 102F includes an electromagnet structure 200 positioned on a needle 116. The electromagnet structure 200 includes a core 204 and an inductor coil 202 wound about the core 204. The electromagnet structure 200 further includes a biocompatible insulating material 128 covering the inductor coil 202. The biocompatible insulating material 128 is selected to be harmless to internal body tissues and to shield the body tissues from the inductor coil 202. In at least one embodiment, the biocompatible insulating material 128 includes a polymer material such as polyamide. In the embodiment of FIG. 10, the electromagnet structure 200 is positioned near the middle of the medical instrument 102F. In other embodiments, one or more electromagnet structures 200 may be placed anywhere along the medical instrument 102F or otherwise in proximity thereto. As the one or more electromagnet structures 200 are tracked, the position of any portion of the medical instrument 102F (e.g., proximal end, distal end, or elsewhere) can be algorithmically (e.g., mathematically) determined.

Figure 11:
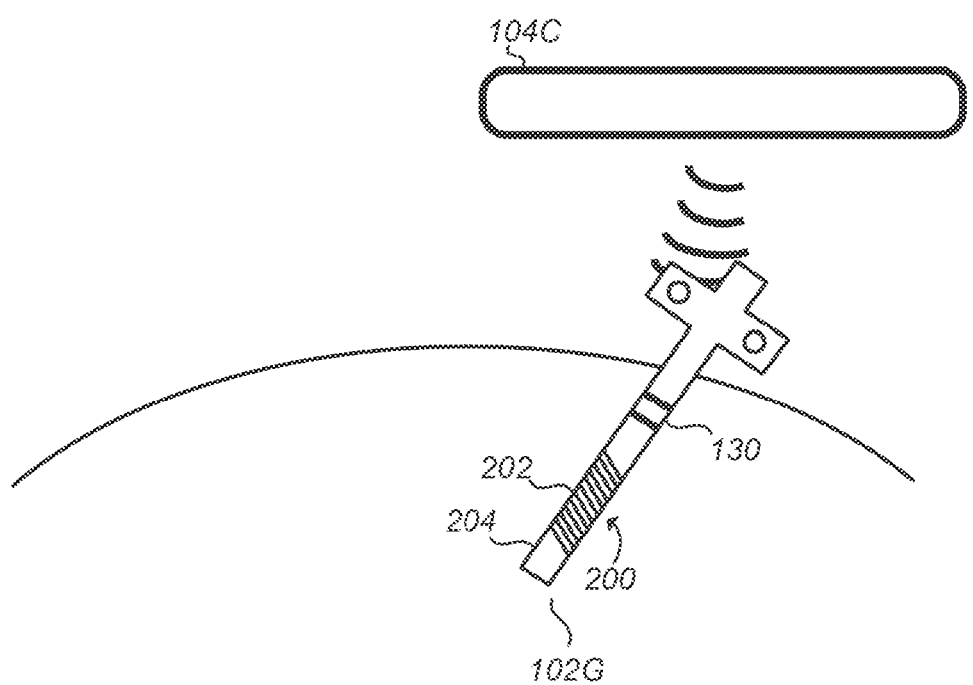
FIG. 11 illustrates a medical instrument configured to be positioned within the body of the patient and including an energy harvesting and storage module, according to one embodiment.

FIG. 11 is an illustration of a medical instrument 102G including an electromagnet structure 200 and an energy harvesting and storage device 130, according to at least one embodiment. The electromagnet structure 200 includes an inductor coil 202 wound about the core 204. The energy harvesting and storage device 130 is coupled to the inductor coil 202, for example by inductor coil leads 152.

The energy harvesting and storage module 130 harvests energy, generates a low-frequency excitation signal, and applies the low-frequency excitation signal across the inductor coil 202 in order to generate a magnetic field as described previously. Inductor coil leads 152 are contained within the medical instrument 102G and not called out in FIG. 11. Thus, there are no inductor leads 152 extending from outside of the body of the patient 110 to the inductor coil 202 inside the body of the patient 202. The energy harvesting and storage module 130 powers the electromagnet structure 200 and generates the excitation signal for the electromagnet structure 200.

In at least one embodiment, the sensor 104C includes a wireless transmitter configured to transmit RF radiation or radiation in another frequency band other than RF. At least some of the energy transmitted by the sensor 104C is collected by the energy harvesting and storage module 130. The energy harvesting and storage module 130 includes internal circuitry that receives the RF radiation, stores energy captured therefrom, generates the excitation signal, and applies the excitation signal to the inductor coil 202. In this way, the energy harvesting and storage module 130 can power the electromagnet structure 200 without a wired connection external to the body of the patient 110. In an alternative embodiment, a transmitter external to the sensor 104C transmits wireless energy to the energy harvesting and storage module 130.

In at least one embodiment, the energy harvesting and storage module 130 harvests energy from a source other than wireless radiation. For example, the energy harvesting and storage module 130 can harvest energy via a thermocouple device from the body heat of the patient. Additionally or alternatively, the energy harvesting and storage module 130 can harvest energy from sound. Additionally or alternatively, the energy harvesting and storage module 130 can also harvest energy from sound or from the movement of the body of the patient.

In at least one embodiment, the energy harvesting and storage module 130 includes piezoelectric energy harvesting circuitry. Piezoelectric energy harvesting can be accomplished by including piezoelectric material within specific circuit structures. The piezoelectric material generates a voltage when a physical stress is applied thereto. This voltage can be used to harvest and store energy as the piezoelectric material is stressed, moved, or jostled in a way such that the voltage is generated.

FIGS. 12A to 12G are a series of cross-sectional diagrams of an electromagnet structure 200 illustrating a process for forming an inductor coil on a medical instrument, according to one embodiment. FIGS. 12A-12G illustrate a process for defining an inductor coil 202 of an electromagnet on a medical instrument 102, according to at least one embodiment.

Figure 12A:
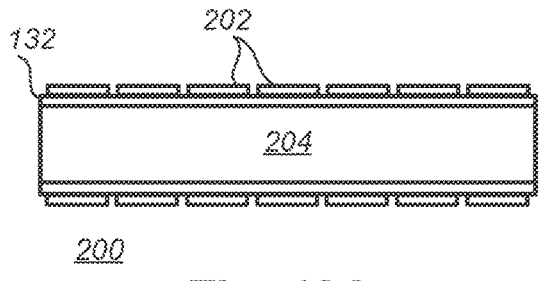
FIGS. 12A to 12G are a series of cross-sectional diagrams of an electromagnet illustrating a process for forming an inductor coil on a medical instrument, according to one embodiment.

In FIG. 12A, the electromagnet structure 200 is in a completed form. The electromagnet structure 200 includes a core 204 and an electrically insulating material 132 positioned around the core 204. An inductor coil 202 is formed on the insulating material 132. The inductor coil 202 can be formed from a conductive ink, paint, or other type of conductive material that can be deposited on the insulating material 132.

Figure 12B:

FIG. 12B illustrates the core 204 of the electromagnet structure 200 before the inductor coil 202 has been formed thereon.

Figure 12C:
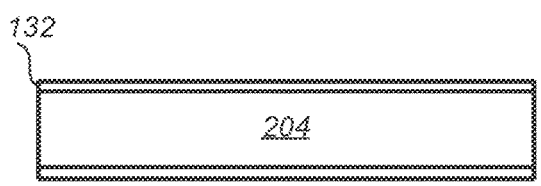

In FIG. 12C, the layer of insulating material 132 has been deposited on the core 204. The insulating material 132 can be deposited by chemical vapor deposition, physical vapor deposition, in the form of a tape wrapped around the core 204, or in any other suitable manner.

Figure 12D:
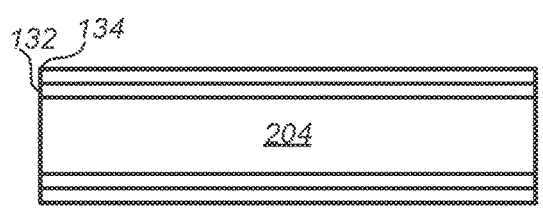

In FIG. 12D, a conductive material 134 has been deposited on the insulating material 132. The conductive material 134 can include a conductive ink or paint that is spread or painted on the insulating material 132. Alternatively, the electromagnet structure 200 can be dipped into a conductive paint in order to coat the insulating layer 132 in the conductive material 134. The conductive material 134 can also be deposited by chemical vapor deposition, physical vapor deposition, thin-film deposition processes, or some other process.

Figure 12E:
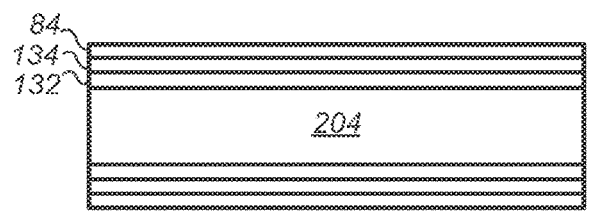

In FIG. 12E, a mask layer 136 has been deposited on the conductive material 134. The mask material can include photoresist, a dielectric material such as silicon dioxide or silicon nitride, or any other suitable material for masking at least a portion of the conductive material 134.

Figure 12F:
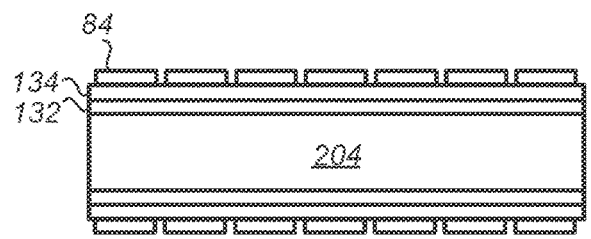

In FIG. 12F, the mask layer 136 has been patterned to define gaps therein exposing portions of the conductive material 134. The mask material 136 can be patterned using photolithography techniques, chemical-etching techniques, or other techniques.

Figure 12G:
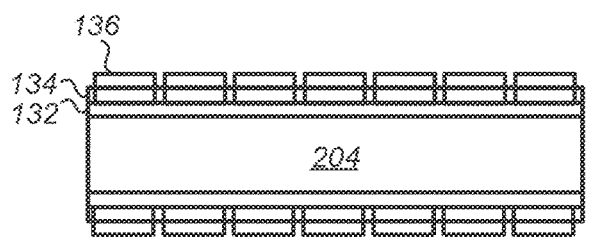

In FIG. 12G the exposed portions of the conductive material 134 have been removed, thereby defining an inductor coil 202 as shown in FIG. 12A. The exposed portions of the conductive material 134 can be removed via a chemical etch such as a wet etch or dry etch. The etchant selectively etches the conductive material 134 with respect to the electrically insulating material 132.

After the conductive material 134 has been etched, the mask layer 136 is entirely removed, leaving the inductor coil 202 structure shown in FIG. 12A.

Because the core 204 may be cylindrical in shape, the process of patterning the photoresist may include rotating the electromagnet structure 200 in a controlled manner while concurrently translating the core along the central axis in order to define a winding pattern in the photoresist. Those of skill in the art will recognize, in light of the present disclosure, that there are other ways to define an inductor coil 202 on a surface that is not flat. All such other ways of defining an inductor coil 202 fall within the scope of the present disclosure.

Figure 13:
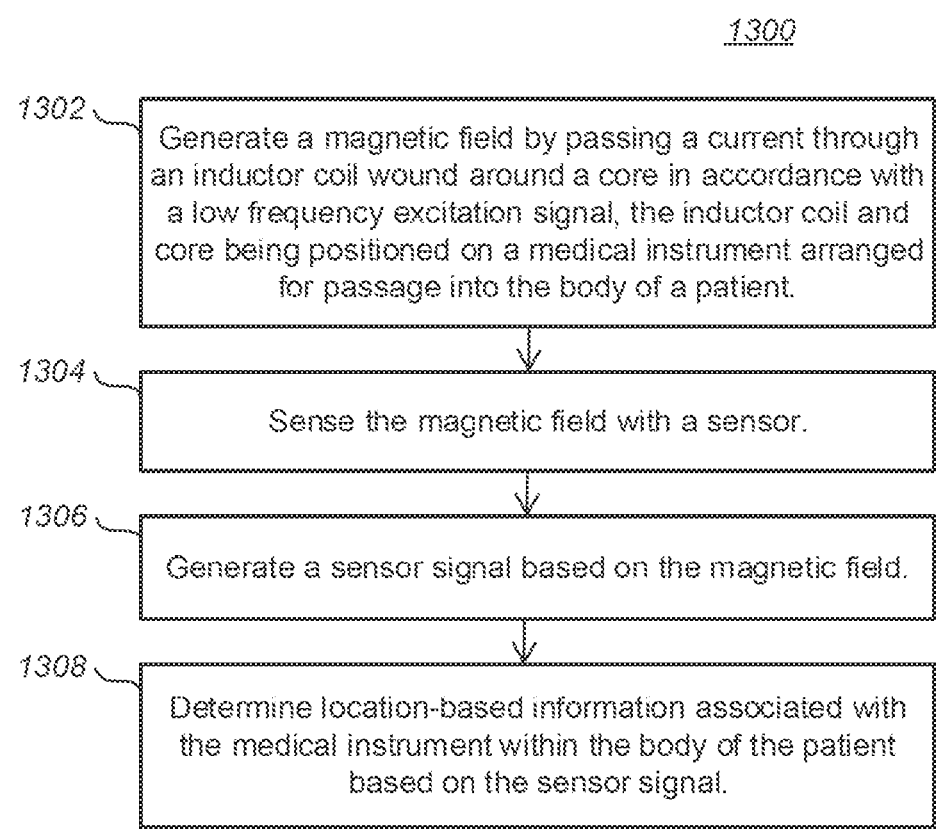
FIG. 13 is a flow diagram of a process for determining one or more of the position, orientation, and motion of a medical instrument within a body of a patient, according to one embodiment.

FIG. 13 is a flow diagram of a process 1300 for detecting the position of a medical instrument 102 within the body of a patient 110, according to at least one embodiment. At 1302, a magnetic field is generated by passing a current through the inductor coil 202 wound around a core 204 in accordance with a low-frequency excitation signal. The inductor coil 202 and the core 204 are positioned on the medical instrument 102 that is moved within the body of the patient.

At 1304, a sensor 104 senses the magnetic field.

At 1306, the sensor 104 generates a sensor signal based on the magnetic field.

At 1308, the control circuit 108 calculates the position of the medical instrument 102 within the body of the patient 110 based on the sensor signal.

One embodiment includes a system and method to track one or more low-frequency electromagnetic trackable structures. The method includes the acts of advancing a medical device into the body of a patient, wherein the medical device has a low-frequency electromagnetic apparatus affixed thereto. The low-frequency electromagnetic apparatus includes at least one ferromagnetic core and at least one conductor. The at least one conductor has a first portion arranged as a plurality of coils wound around a ferromagnetic core and a second portion arranged as a set of conductive leads. The method further includes the acts of applying a low-frequency excitation signal to the set of conductive leads and detecting in real time, from outside the patient's body, at least one magnetic field produced by the low-frequency electromagnetic apparatus. Visual information is presented to track the motion of the medical device inside the body of the patient based on the detected magnetic field.

A first system embodiment includes a medical instrument configured to be inserted within a body of a patient. The instrument includes a first core and a first inductor coil wrapped around the first core. The system further includes a control circuit configured to pass a current through the first inductor coil by applying an excitation signal to the first inductor coil with a frequency below 10,000 Hz. The first inductor coil is configured to generate a magnetic field based on the current. The system also includes a sensor configured to sense the magnetic field and to output to the control circuit a sensor signal based on the magnetic field. The control circuit is configured to calculate a position of the medical instrument within the body of the patient based on the sensor signal.

In some cases of the first system embodiment, the frequency is less than 500 Hz. In some cases of the first system embodiment, the frequency is a harmonic of a second frequency of a municipal power source. In some cases of the first system embodiment, the frequency is about 330 Hz.

In some cases of the first system embodiment, the medical instrument includes a tube. In some of these cases of the first system embodiment, the first core includes a first portion of the tube. In some of these cases, the first coil is wound around the tube. In some of these cases, the tube is a needle. In some of these cases, the tube is a catheter. In some of these cases, the tube is a feeding tube. In some of these cases, the tube is flexible.

In some cases of the first system embodiment, the medical instrument includes a probe. In some cases of the first system embodiment, the medical instrument includes a medical implant configured to be permanently implanted within the patient, and in some of these cases, the control circuit includes an implant portion configured to be permanently implanted with the medical instrument.

In some cases of the first system embodiment, the medical instrument includes an energy harvesting and storage module coupled to the first inductor coil. In some of these cases, the energy harvesting and storage module is configured to harvest energy from wireless signals and to generate the excitation signal from the energy harvested from the wireless signals. In some of these cases, the control circuit is configured to transmit the wireless signals to the implant portion. In some of these cases, the energy harvesting and storage module is configured to harvest energy via a thermocouple and to generate the excitation signal from the energy harvested via the thermocouple. In some of these cases, the energy harvesting and storage module is configured to harvest energy from sound and to generate the excitation signal from the energy harvested from sound. In some of these cases, the energy harvesting and storage module is configured to harvest energy from motion of the body of the patient and to generate the excitation signal from the energy harvested from the motion of the body of the patient.

In some cases of the first system embodiment, the medical instrument is a medical implant delivery device configured to assist in implanting a medical implant within the body of the patient.

In some cases of the first system embodiment, the system also includes a sensor body that houses the sensor. In some of these cases, the control circuit is configured to calculate the position of the medical instrument relative to the sensor body. In some of these cases, the control circuit is configured to generate a video signal and to output the video signal to a display, the video signal including a representation of the position of the medical instrument relative to the sensor body. In some of these cases, the video signal includes both a graphical representation of the sensor body and a graphical representation of the medical instrument. In some of these cases, the sensor includes three or more sensor portions all housed within the sensor body, each sensor portion being configured to sense the magnetic field. In some of these cases, the sensor portions are positioned and oriented to enable collective detection of components of the magnetic field along each of three orthogonal axes. In some of these cases, at least one of sensor portions includes a respective permanent magnet. In some of these cases, the sensor portions include a respective second inductor coil. In some of these cases, at least one of the sensor portions includes a magnetoresistive material. In some of these cases, the magnetoresistive material includes a giant magnetoresistive material. In some of these cases, the magnetoresistive material includes an anisotropic magnetoresistive material. In some of these cases, a first portion of the control circuit is housed within the sensor housing. In some of these cases, a second portion of the control circuit is positioned external to the sensor housing. In some of these cases, the control circuit is housed within the sensor housing.

In some cases of the first system embodiment, the first inductor coil includes a wire coated in a first insulator and wound about the first core. In some of these cases, the wire includes a first terminal and a second terminal. In some of these cases, the control circuit is configured to apply the excitation signal between the first and second terminals. In some of these cases, the first inductor coil is covered in an electrically insulating sheath. In some of these cases, the insulating sheath includes a biocompatible material. In some of these cases, the first core includes an outer shell defining a hollow fluid channel, the first inductor coil being wound around the outer shell.

In some cases of the first system embodiment, the first core has a thickness less than 0.020 inches. In some of these cases, the first core has a thickness less than 10 mils. In some cases of the first system embodiment, the outer shell has a thickness less than 2 mils. In some cases of the first system embodiment, the first core includes steel. In some cases of the first system embodiment, the first core includes steel 1080. In some cases of the first system embodiment, the first core includes a wire. In some cases of the first system embodiment, the excitation signal and frequency are selected to magnetize only a portion of the first core. In some cases of the first system embodiment, the medical instrument includes a second core and a second inductor coil wound around the second core.

In some cases of the first system embodiment, the control circuit is configured to drive the second inductor coil with a second excitation signal having a second frequency less than 10,000 Hz. In some of these cases, at least one of the second excitation signal and the second frequency are different than the first excitation signal and the first frequency. In some of these cases, the second inductor coil generates a second magnetic field that is orthogonal to the first magnetic field. In some of these cases, the first core includes a ferromagnetic material. In some of these cases, the first core includes ferrimagnetic material. In some of these cases, the first core includes a paramagnetic material. In some of these cases, the system further includes a layer of insulating material positioned between the first core and first inductor coil. In some of these cases, the first inductor coil includes a conductive ink. In some of these cases, the first core includes a flexible material.

In some cases of the first system embodiment, the excitation signal includes an AC voltage signal. In some of these cases, the AC voltage signal includes a square wave. In some of these cases, the AC voltage signal includes a sine wave. In some of these cases, the AC voltage has a peak to peak magnitude of less than 40 V.

In a second system embodiment, a method includes generating a magnetic field by passing a first current through a first inductor coil wound around a first core by applying a first excitation signal to the first inductor coil, the first excitation signal having a first frequency less than 10,000 Hz, the first inductor coil and the first core being disposed on a medical instrument positioned in a body of a patient, sensing the magnetic field with a sensor; generating, with the sensor, a sensor signal based on the magnetic field; and calculating a position of the medical instrument within the body of the patient based on the sensor signal.

In some cases of the second first system embodiment, sensing the magnetic field with a sensor includes sensing a plurality of orthogonal components of the magnetic field with a plurality of sensor portions. In some of these cases, generating a sensor signal includes generating plurality of sensor signals based on the plurality of orthogonal components. In some of these cases, the method includes calculating the position of the medical instrument based on the plurality of sensor signals.

In some cases of the second system embodiment, the method includes outputting position data indicating the position of the medical instrument within the body of the patient. In some of these cases, the position data indicates the position of the medical instrument with respect to a sensor housing that houses the sensor. In some of these cases, the method includes outputting a video signal to a display, the video signal including a visual indication of the position of the medical instrument within the body of the patient. In some of these cases, the method includes generating a second current in a second inductor coil wound around a second core by applying a second excitation signal to the second inductor coil, the second excitation signal having a second frequency less than 10,000 Hz, the second inductor coil and the second core being disposed on the medical instrument; generating a second magnetic field in the second core based on the second current; sensing the second magnetic field with the sensor; generating a second sensor signal based on the second magnetic field; and calculating the position of the medical instrument within the body of the patient based on the second sensor signal. In some of these cases, the first inductor coil is positioned within the body of the patient and the second inductor coil is positioned external to the body of the patient.

In a third system embodiment, a method includes applying an excitation signal to an inductor coil disposed on a medical instrument positioned within a body of a patient; receiving a sensor signal from a sensor, the sensor signal based on a magnetic field from the first inductor coil and the core; calculating a position of the medical instrument within the body of the patient based on the sensor signal; and outputting position data indicating the position of the medical instrument. In some of these cases, outputting position data includes outputting a video signal to a display, the video signal configured to cause the display to display a graphical representation of the position of the medical instrument within the body of the patient. In some of these cases, applying an excitation signal to an inductor coil includes applying the excitation signal across two terminals of the inductor coil.

In a fourth system embodiment, a method includes depositing an electrically insulating film on a first portion of a medical instrument configured to be introduced into the body of a patient; depositing a conductive material on the electrically insulating film; defining an inductor coil from the conductive material by removing selected portions of the conductive material, the inductor coil being wound around the first portion of the medical instrument; and defining a first terminal and a second terminal suitable for applying a voltage across the inductor coil, the conductive portion configured to amplify a magnetic field generated by passing a current through the inductor coil.

In some cases of the fourth system embodiment, the depositing a conductive material includes depositing a conductive ink on the electrically insulating film. In some of these cases, defining the inductor coil includes depositing a mask layer on the conductive material, and exposing the selected portions of the conductive material by patterning the mask layer, wherein removing the selected portions includes etching the selected portions by exposing the selected portions to an agent corrosive to the conductive material. In some of these cases, patterning the mask layer includes photolithographically patterning the mask layer. In some of these cases, patterning the mask includes rotating the first portion of the medical instrument.

In a fifth system embodiment, a method includes generating a first current in a first inductor coil wound around a first core by applying a first excitation signal to the first inductor coil, the first excitation signal having a first frequency less than 10,000 Hz. The first inductor coil and the first core are disposed on a medical instrument positioned in a body of a patient. The method further includes generating a magnetic field in the first core based on the first current, sensing the magnetic field with a sensor, generating a sensor signal based on the magnetic field, and calculating a position of the medical instrument within the body of the patient based on the sensor signal.

In a sixth system embodiment, a method includes applying an excitation signal to an inductor coil disposed on a medical instrument positioned within a body of a patient and receiving a sensor signal from a sensor, the sensor signal based on a magnetic field from the first inductor coil and the core. The method also includes calculating a position of the medical instrument within the body of the patient based on the sensor signal and outputting position data indicating the position of the medical instrument.

In a seventh system embodiment, a method includes depositing an electrically insulating film on a first portion of a medical instrument configured to be introduced into the body of a patient and depositing a conductive material on the electrically insulating film. The method also includes defining an inductor coil from the conductive material by removing selected portions of the conductive material. The inductor coil is wound around the first portion of the medical instrument. The method further includes defining a first terminal and a second terminal suitable for applying a voltage across the inductor coil. The conductive material is configured to become magnetized when a current is passed through the inductor coil.

In eighth system embodiment, a device includes a sensor housing and a plurality of sensors disposed within the sensor housing. The plurality of sensors are configured to collectively sense three orthogonal components of a magnetic field generated by an electromagnet disposed on a medical instrument positioned within a body of a patient and driven by an excitation signal having a frequency less than 10,000 Hz. The sensors are configured to output a plurality of respective sensor signals based on the magnetic field. The sensors signals are collectively indicative of a position of the medical instrument within the body of the patient.

In some cases of the eighth system embodiment, the device includes a control circuit disposed within the sensor housing and configured to receive the sensor signals and to calculate the position of the medical instrument within the body of the patient based on the sensor signals. In some of these cases, the control circuit is configured to apply the excitation signal across the electromagnet. In some of these cases, the control circuit is configured to output position data indicating the position of the medical instrument within the body of the patient relative to the sensor housing. In some of these cases, the device includes output circuitry configured to output one or more of the sensor signals to a control circuit external to the sensor housing. In some of these cases, the sensor signals are analog signals. In some of these cases, the sensor signals are digital signals.

In a ninth system embodiment, a system includes at least one processor and at least one memory coupled to the at least one processor. The at least one memory has stored therein instructions which, when executed by any set of the one or more processors, perform a process. The process includes applying an excitation signal across an inductor coil disposed on a medical instrument positioned within a body of a patient, the excitation signal having a frequency less than 10,000 Hz. The process further includes receiving a sensor signal from a sensor, the sensor signal based on a magnetic field from the inductor coil and the core and calculating a position of the medical instrument within the body of the patient based on the sensor signal. The process further includes outputting position data indicating the position of the medical instrument.

In some cases of the ninth system embodiment, outputting position data includes outputting a video signal to a display, the video signal configured to cause the display to display a graphical representation of the position of the medical instrument within the body of the patient. In some of these cases, applying an excitation signal across an inductor coil includes applying the excitation signal across two terminals of the inductor coil. In some of these cases, the frequency is less than 500 Hz. In some of these cases, the frequency is about 330 Hz. In some of these cases, the system further includes outputting position data indicating the position of the medical instrument within the body of the patient. In some of these cases, applying an excitation signal to an inductor coil includes applying a low-frequency AC voltage across the inductor coil. In some of these cases, the low-frequency AC voltage includes a square wave.

Referring to the embodiments described in the present disclosure, the selection of various parameters in a low-frequency electromagnetic tracking system is generally directed by the environment where the trackable structure will be placed and the environment where a magnetic field sensing device will be operated. The various parameters include the material composition of the physical parts to be tracked (i.e., the core, the conductor, the trackable structure, and the like), the size and shape of the physical parts to be tracked, the configuration and relative positions of the physical parts to be tracked, the excitation voltage, the excitation current, the excitation frequency, and other such parameters.

Low-frequency excitation signals described in the present disclosure provide benefits with respect to real-time tracking of a medical device having an associated electromagnet structure. Since the excitation signal forces the low-frequency electromagnetic apparatus to change polarity at a trackable, predictable frequency or pattern, the tracking system is more immune to magnetic interference such as those generated from the earth's magnetic field, electronic devices, nearby metallic objects, and other generally interference-causing sources.

In the embodiments discussed herein, sensors such as magnetic field sensing devices generate and provide or otherwise direct the generation and provision of an excitation signal to the inductor coil of a low-frequency electromagnetic apparatus. The sensor (e.g., magnetic field sensing device) can thereby synchronize detected magnetic field measurements and predictive magnetic field calculations with the known polarity and expected magnetic flux density B produced when the excitation signal is provided to the low-frequency electromagnetic apparatus.

Producing the excitation signal using the sensor (e.g., magnetic field sensing device), or producing the excitation signal with some other source in association with the operations of the sensor provides additional benefits. For example, in some cases, a plurality of low-frequency electromagnetic apparatuses can all be concurrently tracked. A separate excitation signal may be applied to each different apparatus, and each different apparatus may be separately detected. The excitation signals may be multiplexed, they may be provided using a time division multiple access (TDMA) scheme, a frequency shift keying scheme, or they may be provided in some other way.

The low-frequency excitation signals in the embodiments described herein may be around 300 Hz (e.g., 330 Hz). Other embodiments may apply excitation signals to electromagnetic apparatus embodiments at frequencies between about 50 Hz and about 10,000 Hz. Different frequencies and ranges of frequencies are also contemplated. In some embodiments, a plurality of electromagnetic apparatus embodiments located in the same general vicinity of each other may be cooperatively operated using excitation signals having different frequencies, phases, signatures, or other different characteristics. In this way, each different electromagnetic apparatus will generate a different magnetic profile (e.g., "signature") when detected and tracked by a sensor (e.g., magnetic field sensing device). In some embodiments, the number of concurrently trackable electromagnetic apparatuses is limited by the processing speed of the sensor, the refresh rate of the sensor, the selected excitation frequencies, or other such parameters.

In some cases, the lower end of the acceptable frequency range for an exemplary electromagnetic apparatus is determined by electronics noise, update rate, and other factors. In some cases, the upper end of the acceptable frequency range for an exemplary electromagnetic apparatus is based at least in part on the size of the core. For example, a smaller core may permit a higher frequency. At least one other factor that may contribute to an acceptable frequency range is a size, shape, and placement of a ground plane in the sensor (e.g., magnetic field sensing device).

A trackable structure, as the term is used herein (e.g., medical instrument 102), is a medical device arranged to bear, carry, or otherwise include an integrated or coupled low-frequency electromagnetic apparatus (e.g., electromagnet structure 200). A medical device (e.g., medical instrument) refers to an instrument, apparatus, constructed element or composition, machine, implement, or similar or related article that can be utilized to diagnose, prevent, treat or manage a disease or other condition(s). The medical devices provided herein may, depending on the device and the embodiment, be implanted within a patient, utilized to deliver a device to a patient, or utilized externally on a patient. In many embodiments the medical devices provided herein are sterile and subject to regulatory requirements relating to their sale and use.

In the present disclosure, the tracking of medical instruments or portions thereof (e.g., electromagnet structures) is performed to an acceptable accuracy. As used in the present disclosure, "acceptable accuracy" is any level of accuracy determined to be acceptable by a medical practitioner performing a respective medical procedure. For example, in the placement of a cardiovascular medical instrument, acceptable accuracy may be within one centimeter (1 cm), within one millimeter (1 mm), within 100 microns, or within some other measurement. In other medical procedures, for example in the placement of a feeding tube (e.g., a percutaneous endoscopic gastrostomy (PEG) tube), the acceptable accuracy may be within five centimeters (5 cm), within two centimeters (2 cm), or within some other measurement. In some cases, acceptable accuracy is determined linearly within two dimensions. In other cases, acceptable accuracy is determined in three dimensions. In some cases, acceptable accuracy includes a time parameter such that information associated with distance and positional tracking of a medical instrument is associated with a measure of time. For example, acceptable accuracy in some cases may include a first position of a medical instrument at a first time and a second position of the medical instrument at a second time. Time parameters, when associated with an acceptable accuracy, may include linear time, rate, rate of change, or any other such time parameter.

Certain words and phrases used in the specification are set forth as follows. The terms "include" and "comprise," as well as derivatives thereof, mean inclusion without limitation. The term "or," is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation, such a device may be implemented in hardware, firmware, or software, or some combination of at least two of the same. The functionality associated with any particular controller may be centralized or distributed, whether locally or remotely. Other definitions of certain words and phrases may be provided within this patent document. Those of ordinary skill in the art will understand that in many, if not most instances, such definitions apply to prior as well as future uses of such defined words and phrases.

A processor (i.e., a processing unit), as used in the present disclosure, refers to one or more processing units individually, shared, or in a group, having one or more processing cores (e.g., execution units), including central processing units (CPUs), digital signal processors (DSPs), microprocessors, micro controllers, state machines, and the like that execute instructions. In the present disclosure, memory may be used in one configuration or another. The memory may be configured to store data. In the alternative or in addition, the memory may be a non-transitory computer readable medium (CRM) wherein the CRM is configured to store instructions executable by a processor. The instructions may be stored individually or as groups of instructions in files.

The files may include functions, services, libraries, and the like. The files may include one or more computer programs or may be part of a larger computer program. Alternatively, or in addition, each file may include data or other computational support material useful to carry out the computing functions of the systems, methods, and apparatus described in the present disclosure. Some or all of the stored contents of a memory may include software instructions executable by a processing device to carry out one or more particular acts.

In the present disclosure, certain features may be implemented with one or more computing devices. For brevity, the computing devices are not shown in detail in the present figures because one of skill in the art will recognize that a computing device includes a plurality of computing circuits such as at least one processor communicatively coupled to at least one memory and arranged to execute instructions that are stored in the memory to implement various features (e.g., FIG. 13) of a system for detecting the position of a medical instrument within the body of a patient. The control circuit 108 (FIG. 1), for example, may include one or more computing devices that direct the generation of excitation signals, that direct the detection and capture of magnetic field signals, that produce position information, that present the position information through an input/output device, and that perform other tasks. Resources of such computing devices may be shared to implement one or more of the features, or the resources of such computing devices may be dedicated to implementing certain ones of the features. Resources of such computing devices are in some cases located exclusively in the control circuit 108. In other cases, however, portions of computing resources may be located in a sensor, an input/output device, a medical device, a hand-held device, a network-connected remote device, or some other device.

The terms "real-time" or "real time," as used herein and in the claims that follow, are not intended to imply instantaneous processing, transmission, reception, or otherwise as the case may be. Instead, the terms, "real-time" and "real time" imply that the activity occurs over an acceptably short period of time (e.g., over a period of microseconds or milliseconds), and that the activity may be performed on an ongoing basis. An example of an activity that is not real-time is one that occurs over an extended period of time (e.g., hours or days) or that occurs based on intervention or direction by a person or other activity, such as each magnetic sense measurement occurring at the press of a button. In the foregoing description, certain specific details are set forth to provide a thorough understanding of various disclosed embodiments. However, one skilled in the relevant art will recognize that embodiments may be practiced without one or more of these specific details, or with other methods, components, materials, etc. In other instances, well-known structures associated with electronic and computing systems including client and server computing systems, as well as networks have not been shown or described in detail to avoid unnecessarily obscuring descriptions of the embodiments. Unless the context requires otherwise, throughout the specification and claims which follow, the word "comprise" and variations thereof, such as "comprises" and "comprising," are to be construed in an open, inclusive sense, e.g., "including, but not limited to."

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. As used in this specification and the appended claims, the singular forms "a," "an," and "the" include plural referents unless the content and context clearly dictates otherwise. It should also be noted that the conjunctive terms, "and" and "or" are generally employed in the broadest sense to include "and/or" unless the content and context clearly dictates inclusivity or exclusivity as the case may be. In addition, the composition of "and" and "or" when recited herein as "and/or" is intended to encompass an embodiment that includes all of the associated items or ideas and one or more other alternative embodiments that include fewer than all of the associated items or ideas.

The headings and Abstract of the Disclosure provided herein are for convenience only and do not limit or interpret the scope or meaning of the embodiments.

The various embodiments described above can be combined to provide further embodiments. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system, comprising:
a medical instrument configured to be inserted in a body of a patient, the medical instrument including:
a core, the core including a ferromagnetic material; and
an inductor coil wound around the core;
a control circuit configured to drive the inductor coil with an alternating current excitation signal having a low-frequency, the alternating current excitation signal causing a current having current pulses of alternate polarity to pass through the inductor coil, the alternating current excitation signal having the low-frequency below 10,000 Hz, the core being configured to be magnetically saturated for a period of time for each current pulse of each respective polarity, the inductor coil and the saturated core being configured to generate a magnetic field based in part on a waveform of the current pulses of the alternating current excitation signal, wherein the generated magnetic field includes alternate magnetic directions of the magnetic core for each polarity reversal of the current pulses that configure the core as a polarity reversible permanent magnet that is magnetically saturated for a period of time for each current pulse of each respective polarity during operation of the control circuit; and
a sensor configured to sense the magnetic field and to output to the control circuit a sensor signal including parameters based on the magnetic field, wherein the control circuit is further configured to calculate position information associated with the medical instrument within the body of the patient based on the parameters of the sensor signal.

2. The system of claim 1, wherein the frequency is less than 500 Hz.

3. The system of claim 2, wherein the frequency is about 330 Hz.

4. The system of claim 1, wherein the medical instrument includes a tube.

5. The system of claim 4, wherein the tube is a catheter.

6. The system of claim 1, wherein the medical instrument includes a medical implant configured to be permanently implanted within the patient.

7. The system of claim 1, wherein the position information includes information representing a three-dimensional position of the medical instrument, an orientation of the medical instrument, and motion of the medical instrument.

8. The system of claim 7, wherein the control circuit is further configured to generate a video signal and to output the video signal to a display, the video signal including a representation of the position information.

9. The system of claim 1, wherein the inductor coil includes a wire coated in an insulator material.

10. The system of claim 1, wherein the core has a thickness less than 0.020 inches.

11. A low-frequency electromagnetic trackable structure, comprising:
a medical instrument having a core formed on a distal end of the medical instrument, wherein at least the distal end of the medical instrument is arranged for insertion into a body of a patient, the core including a ferromagnetic material; and
an inductor coil wound around the core, wherein the inductor coil is configured to receive an alternating current excitation signal having a frequency below 10,000 Hz, the alternating current excitation signal causing a current having current pulses of alternate polarity to pass through the inductor coil,
wherein, in operation, the core is configured to be magnetically saturated for a period of time for each current pulse of each respective polarity, the low-frequency electromagnetic trackable structure arranged to generate a trackable magnetic field based in part on a waveform of the current pulses of the alternating current excitation signal, wherein the generated trackable magnetic field includes alternate magnetic directions of the magnetic core for each polarity reversal of the current pulses that configure the core of the medical instrument as a polarity reversible permanent magnet that is magnetically saturated for a period of time for each current pulse of each respective polarity during the operation.

12. The low-frequency electromagnetic trackable structure of claim 11, wherein the frequency of the alternating current excitation signal is about 330 Hz.

13. The low-frequency electromagnetic trackable structure of claim 11, wherein the medical instrument is a peripherally inserted central catheter (PICC).

14. The low-frequency electromagnetic trackable structure of claim 11, comprising:
a surface coating arranged on at least part of the low-frequency electromagnetic trackable structure, the surface coating including a bio-compatible material.

15. A low-frequency electromagnetic trackable structure, comprising:
a medical instrument having a core formed on a distal end of the medical instrument, wherein at least the distal end of the medical instrument is arranged for insertion into a body of a patient; and
an inductor coil wound around the core, wherein the inductor coil is arranged to receive an excitation signal having a frequency below 10,000 Hz, the low-frequency electromagnetic trackable structure arranged to generate a trackable magnetic field when the excitation signal is received, wherein the medical instrument is arranged as a needle having a first portion of a first material and a second portion of a second material, the first material and the second material having different elemental compositions, wherein the core is integrated in the first portion of the needle, and wherein the first material is a ferromagnetic material.

16. A method to track a low-frequency electromagnetic trackable structure, comprising:

advancing a medical device into a body of a patient, the medical device having a low-frequency electromagnetic apparatus affixed thereto, the low-frequency electromagnetic apparatus including:

at least one ferromagnetic core that is configured as a polarity reversible permanent magnet; and at least one conductor having a first portion and a second portion, the first portion arranged as a plurality of coils wound around the at least one ferromagnetic core and the second portion arranged as a set of first and second conductive leads;

applying a low-frequency excitation signal having pulses of alternate polarity to the set of first and second conductive leads;

saturating the at least one ferromagnetic core based in part on a waveform of the pulses of the low-frequency excitation signal having alternate polarity;

generating a magnetic field including alternate magnetic directions during a period between each polarity reversal of the pulses;

detecting in real time, from outside the body of the patient, at least one magnetic field produced by the low-frequency electromagnetic apparatus; and presenting visual information that tracks motion of the medical device inside the body of the patient based on the detection of the at least one magnetic field.

17. The method of claim 16, wherein the low-frequency excitation signal is below 500 Hz.

18. The method of claim 16, wherein the at least one ferromagnetic core has a cross-section diameter of between about 0.005 inches and 0.250 inches.

19. The method of claim 16, wherein the at least one ferromagnetic core has a cross-section diameter of between about 0.00025 inches and 0.05 inches.

* * * * *

UNITED STATES PATENT AND TRADEMARK OFFICE
CERTIFICATE OF CORRECTION

| | |
|---|---|
| PATENT NO. | : 11,022,421 B2 |
| APPLICATION NO. | : 16/071891 |
| DATED | : June 1, 2021 |
| INVENTOR(S) | : Samuel Peter Andreason et al. |

It is certified that error appears in the above-identified patent and that said Letters Patent is hereby corrected as shown below:

On the Title Page

Page 2, Item (56) References Cited/Foreign Patent Documents:
"EP 0 555 131 A2 8/1993" should read: --EP 0 555 031 A2 8/1993--

Signed and Sealed this
Nineteenth Day of April, 2022

Katherine Kelly Vidal
*Director of the United States Patent and Trademark Office*